US008204241B2

(12) United States Patent
Asada et al.

(10) Patent No.: US 8,204,241 B2
(45) Date of Patent: Jun. 19, 2012

(54) SOUND OUTPUTTING APPARATUS, SOUND OUTPUTTING METHOD, SOUND OUTPUT PROCESSING PROGRAM AND SOUND OUTPUTTING SYSTEM

(75) Inventors: Kohei Asada, Kanagawa (JP); Goro Shiraishi, Tokyo (JP)

(73) Assignee: Sony Corporation, Tokyo (JP)

( * ) Notice: Subject to any disclaimer, the term of this patent is extended or adjusted under 35 U.S.C. 154(b) by 1170 days.

(21) Appl. No.: 11/952,468

(22) Filed: Dec. 7, 2007

(65) Prior Publication Data

US 2008/0159568 A1 Jul. 3, 2008

(30) Foreign Application Priority Data

Dec. 27, 2006 (JP) ................................ 2006-350962

(51) Int. Cl.
*A61F 11/06* (2006.01)
*G10K 11/16* (2006.01)
*H03B 29/00* (2006.01)

(52) U.S. Cl. .................. 381/71.1; 381/71.6; 381/71.11; 381/150

(58) Field of Classification Search ................. 381/71.1, 381/71.6, 71.11, 150, 370
See application file for complete search history.

(56) References Cited

U.S. PATENT DOCUMENTS

| | | | | |
|---|---|---|---|---|
| 5,452,361 A * | 9/1995 | Jones | ........................... | 381/71.6 |
| 2003/0228019 A1* | 12/2003 | Eichler et al. | ................ | 381/71.8 |
| 2006/0013408 A1* | 1/2006 | Lee | .............................. | 381/71.6 |
| 2007/0036367 A1* | 2/2007 | Ko | .............................. | 381/71.1 |
| 2009/0034748 A1* | 2/2009 | Sibbald | ........................ | 381/71.6 |

FOREIGN PATENT DOCUMENTS

| | | |
|---|---|---|
| JP | 2-231900 | 9/1990 |
| JP | 6-70391 | 3/1994 |
| JP | 8-79873 | 3/1996 |
| JP | 2003-143683 | 5/2003 |
| JP | 3114245 | 9/2005 |

OTHER PUBLICATIONS

U.S. Appl. No. 11/936,894, filed Nov. 8, 2007, Asada, et al.
U.S. Appl. No. 11/865,419, filed Oct. 1, 2007, Asada, et al.
U.S. Appl. No. 11/865,354, filed Oct. 1, 2007, Asada.
U.S. Appl. No. 11/868,815, filed Oct. 8, 2007, Itabashi, et al.
U.S. Appl. No. 11/875,374, filed Oct. 19, 2007, Asada.
U.S. Appl. No. 11/936,882, filed Nov. 8, 2007, Asada, et al.
U.S. Appl. No. 11/936,876, filed Nov. 8, 2007, Asada, et al.
U.S. Appl. No. 11/966,168, filed Dec. 28, 2007, Ohkuri, et al.
U.S. Appl. No. 11/966,452, filed Dec. 28, 2007, Itabashi, et al.
U.S. Appl. No. 12/015,824, filed Jan. 17, 2008, Asada, et al.
Japanese Office Action dated Jan. 24, 2012 in corresponding Japanese application No. 2006-350962, filed on Dec. 27, 2006.

* cited by examiner

*Primary Examiner* — Phat X Cao
(74) *Attorney, Agent, or Firm* — Oblon, Spivak, McClelland, Maier & Neustadt, L.L.P.

(57) ABSTRACT

The present invention provides a sound outputting apparatus, including: a housing; an electro-acoustic conversion section provided in the housing and configured to acoustically reproduce and output a sound signal; an acousto-electric conversion section provided at a position of the housing at which sound acoustically reproduced by the electro-acoustic conversion section can be collected; a removing section configured to remove a component of the sound signal from an output signal to be outputted from the acousto-electric conversion section based on an acoustic transfer function between the electro-acoustic conversion section and the acousto-electric conversion section; a decision section configured to decide whether or not a predetermined operation is performed for the housing based on an output signal from the removing section; and a control section configured to control so that a predetermined process is performed based on a result of the decision by the decision section.

15 Claims, 45 Drawing Sheets

FIG. 4

$$P = \frac{1}{1 + ADHfbM\beta} N + \frac{AHfbD}{1 + ADHfbM\beta} ES$$ ··· EXPRESSION 1

$$\left| \frac{1}{1 + ADHfbM\beta} \right| < 1$$ ··· EXPRESSION 2

$$E = (1 + ADHfbM\beta)$$ ··· EXPRESSION 3

$$P = \frac{1}{1 + ADHfbM\beta} N + ADHfbS$$ ··· EXPRESSION 4

$$P = -F' ADHM\alpha N + FN + ADHfbS$$ ··· EXPRESSION 5

$$P = -F' ADHM\alpha$$ ··· EXPRESSION 6

$$P = ADHS$$ ··· EXPRESSION 7

SOUND OUTPUTTING APPARATUS, SOUND OUTPUTTING METHOD, SOUND OUTPUT PROCESSING PROGRAM AND SOUND OUTPUTTING SYSTEM

CROSS REFERENCES TO RELATED APPLICATIONS

The present invention contains subject matter related to Japanese Patent Application JP 2006-350962 filed in the Japan Patent Office on Dec. 27, 2006, the entire contents of which being incorporated herein by reference.

BACKGROUND OF THE INVENTION

1. Field of the Invention

This invention relates to a sound outputting apparatus such as, for example, a headphone apparatus and a portable telephone terminal and also to a sound outputting method and a sound output processing program for use with the apparatus as well as a sound outputting system which includes a headphone apparatus and a sound outputting apparatus.

2. Description of the Related Art

In order to acoustically reproduce a reproduction sound signal of a portable audio player and listen to the sound, usually a headphone apparatus or an earphone apparatus is used. In this instance, sound volume adjustment or sound quality adjustment is performed by operation by a user of an operation button or an operation knob provided on the body of the audio player.

However, it is cumbersome to operate the operation button or the operation knob on the portable audio player while the user listens to music or the like using the headphone apparatus or earphone apparatus. Particularly where the portable player is accommodated in a pocket of clothes or in a bag, the user may have to perform a cumbersome action of intentionally taking out and operating the portable player.

Meanwhile, a headphone apparatus or an earphone apparatus is sometimes provided with an adjustment section including an operation button or an operation knob. In this instance, the adjustment section is provided intermediately of a connection cable of the headphone apparatus or earphone apparatus to a portable audio player. Thus, the adjustment section sometimes hangs down in front of the breast of the user and makes an obstacle to the user.

Meanwhile, a command inputting apparatus such as an earphone microphone for a potable telephone set has been proposed and is disclosed in Japanese Patent Laid-Open No. 2003-143683 (hereinafter referred to as Patent Document 1) wherein, when an apparatus body is beaten, an oscillation of the apparatus body is detected by an oscillation detection element and the detected oscillation is inputted as a command. Where the command inputting apparatus of Patent Document 1 is used, a command can be inputted without such a cumbersome action as described above.

SUMMARY OF THE INVENTION

However, in the command inputting apparatus disclosed in Patent Document 1, in order to detect a command input from an oscillation, an acceleration sensor must be provided, and this gives rise to a problem that the cost increases as much. Therefore, it is a possible idea to collect sound using a microphone provided originally in the apparatus body and detect from the collected sound signal that the apparatus body is beaten.

However, in a headphone apparatus used in a music player or a like apparatus, sound collected by a microphone includes also sound acoustically reproduced by a headphone driver. Therefore, it is difficult to detect accurately that the apparatus body is beaten. It is to be noted that, in the present specification, the term "beating" is used to represent that a housing is beaten, tapped or struck once or a plural number of times by a finger or the like.

Therefore, it is desirable to provide a sound outputting apparatus, a sound outputting method, a sound output processing program and a sound outputting system which solve the problem described above.

According to the present invention, there is provided a sound outputting apparatus comprising a housing, an electro-acoustic conversion section provided in the housing and configured to acoustically reproduce and output a sound signal, an acousto-electric conversion section provided at a position of the housing at which sound acoustically reproduced by the electro-acoustic conversion section can be collected, a removing section configured to remove a component of the sound signal from an output signal to be outputted from the acousto-electric conversion section based on an acoustic transfer function between the electro-acoustic conversion section and the acousto-electric conversion section, a decision section configured to decide whether or not a predetermined operation is performed for the housing based on an output signal from the removing section, and a control section configured to control so that a predetermined process determined in advance is performed based on a result of the decision by the decision section.

In the sound outputting apparatus, the removing section removes, from a signal from the acousto-electric conversion section such as, for example, a microphone, a component of the sound signal acoustically reproduced by the electro-acoustic conversion section taking the acoustic transfer function between the electro-optical conversion section such as, for example, a headphone driver and the acousto-electric conversion section into consideration.

Then, based on the signal from the removing section, it is decided by the decision section whether or not the predetermined operation is performed for the housing. Then, the control section performs the predetermined process determined in advance when it is decided that the predetermined operation is performed for the housing.

With the sound outputting apparatus, since the decision section decides whether or not the predetermined operation is performed for the housing after the sound signal component acoustically reproduced by the electro-acoustic conversion section is removed from the signal from the acousto-electric conversion section, it can be decided accurately whether or not the predetermined operation is performed for the housing.

BRIEF DESCRIPTION OF THE DRAWINGS

FIGS. 4 and 5 are views illustrating the noise reduction apparatus section in the sound outputting apparatus according to the first embodiment of the present invention;

DETAILED DESCRIPTION OF THE PREFERRED EMBODIMENTS

Figure 1:
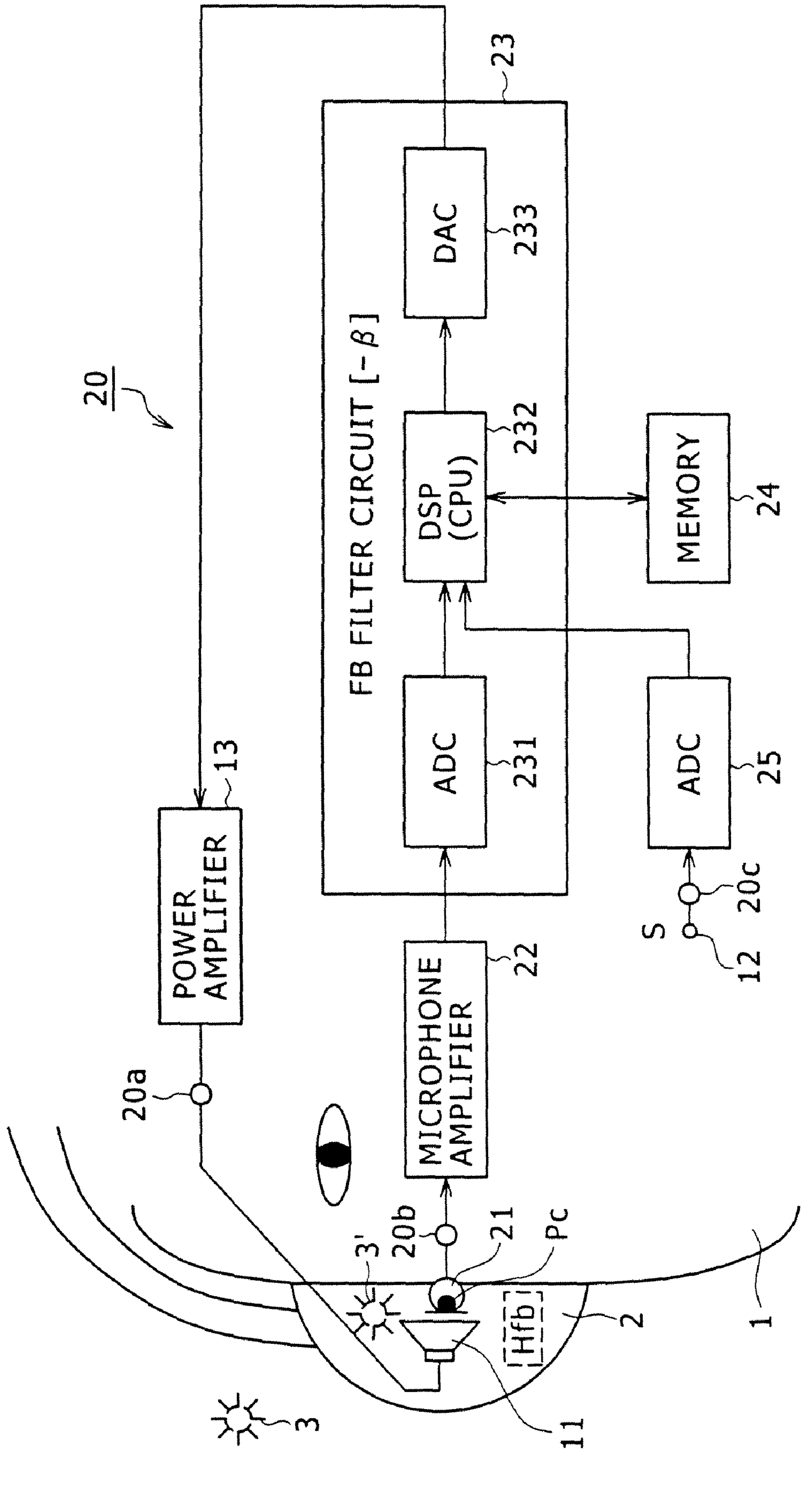
FIG. 1 is a block diagram showing an example of a headphone apparatus to which a sound outputting apparatus according to a first embodiment of the present invention is applied.

In the following, several embodiments of the present invention wherein the present invention is applied to a sound outputting apparatus are described with reference to the accompanying drawings. More particularly, in the embodiments described below, the present invention is applied to headphone apparatus which include a noise reproduction apparatus. The invention is applied also to a novel noise reduction method.

Together with popularization of portable audio players, also a noise reduction system begins to be popularized which is applied to a headphone or an earphone for a portable audio player and reduces noise of an external environment thereby to provide a good reproduction music space in which the external noise is reduced to a listener.

An example of a noise reduction system of the type described is a noise reduction system of the active type which carries out active noise reduction. An active noise reduction system basically has the following configuration. In particular, a microphone serving as an acousto-electrical conversion section collects external noise. Then, from a sound signal of the collected noise, a noise reduction sound signal having an acoustic phase opposite to that of the noise is generated. The thus generated noise reduction sound signal is acoustically reproduced by a speaker or a headphone driver serving as an electro-acoustic conversion section and is acoustically synthesized with the noise to reduce the noise.

In the active noise reduction system, a portion for generating the noise reduction sound signal is formed from an analog circuit (analog filter) in the past, and a fixed filter circuit is used which can reduce, in any noise environment, the noise in its own way.

Incidentally, a noise environment characteristic generally differs greatly depending upon the environment of the site such as an airport, a platform of a train station or a factory even where it is observed as a frequency characteristic. Accordingly, in order to reduce noise, it is originally desirable to use an optimum filter characteristic conforming to each environment characteristic.

However, as described above, in the active noise reduction system in the past, the filter circuit is fixed to that of a single filter characteristic which can achieve, in any noise environment, noise reduction in its own way. Therefore, the active noise reduction system in the past has a problem in that it does not carry out noise reduction conforming to a noise environment characteristic of the site at which the noise reduction is to be carried out.

Therefore, a noise reduction apparatus section adopted in the headphone apparatus of the embodiments of the present invention is configured such that it does not use a filter circuit of a single filter characteristic but includes a plurality of filter circuits having different filter characteristics such that a filter circuit conforming to the noise environment characteristic of the site is selectively used.

At this time, the listener would listen to the sound and confirm which one of the filter circuits selectively used exhibits an optimum noise reduction effect or an optimum noise cancel effect. However, if the filter characteristic is changed over in a state wherein a noise reduction filter effect is applied, then there is a problem that it is not easy to confirm the noise reduction effect regarding each filter characteristic. Therefore, the embodiments described below solve or moderate the problem just described.

In the headphone apparatus as sound outputting apparatus according to the embodiments of the present invention described below, the noise reduction apparatus section has a digital processing circuit configuration using a digital filter such that, by switchably altering the filter coefficient, a suitable noise reduction characteristic is selectively applied in conformity with any of a plurality of different noise environments. In the embodiments described below, selective changeover of the noise reduction characteristic can be performed by beating of a headphone housing.

It is to be noted that, while the noise reduction apparatus may have a configuration of an analog processing circuit, in this instance, it is necessary to provide filter circuits corresponding to a plurality of noise environments as individual hardware circuits and selectively use one of the filter circuits. However, if the noise reduction apparatus is configured such that a plurality of filter circuits are provided and one of the filter circuits is selectively used in this manner, then this gives rise to a problem that the hardware configuration becomes large in scale and an increased cost is required. Therefore, it is not practical to apply the analog processing circuit configuration to a noise reduction system to be used for portable apparatus. Therefore, the embodiments described below adopts a digital processing circuit configuration.

First Embodiment

Noise Reduction Apparatus of the Feedback Type

A noise reduction apparatus for a headphone apparatus as a sound outputting apparatus according to a first embodiment of the present invention is described first. The noise reduction apparatus has a system configuration which achieves active noise reduction. Active noise reduction systems are divided into two types including a feedback system (feedback type) and a feedforward system (feedforward type). The present invention can be applied to noise reduction systems of both types.

Figure 2:
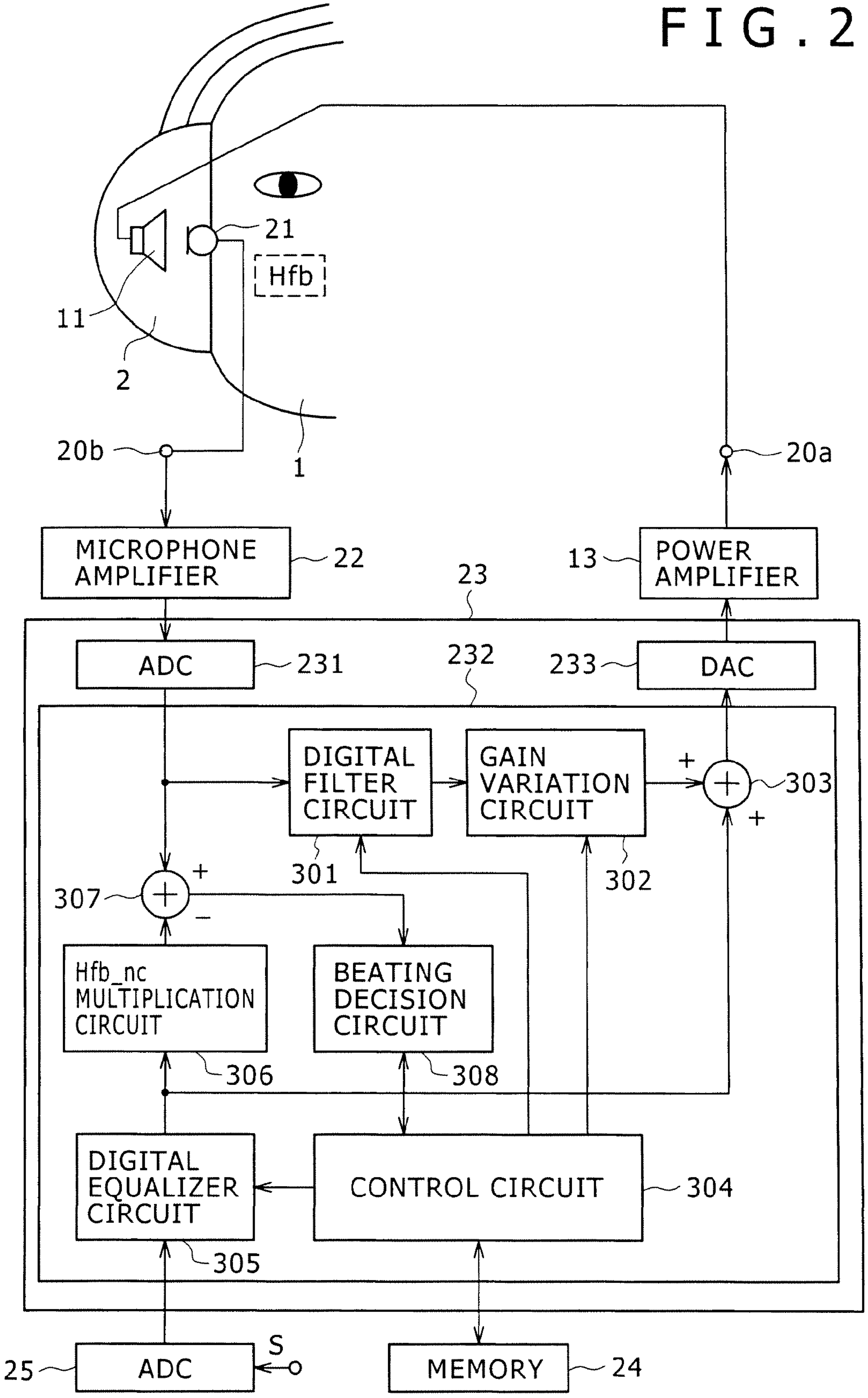
FIG. 2 is a block diagram showing an example of a detailed configuration of an FB filter circuit shown in FIG. 1.

First, a noise reduction apparatus section of a headphone apparatus as a sound outputting apparatus according to the first embodiment of the present invention to which a noise reduction system of the feedback type is applied is described. FIG. 1 shows an example of a configuration of the headphone apparatus, and FIG. 2 shows an example of a detailed configuration of a filter circuit shown in FIG. 1.

In FIG. 1, a configuration only of a portion of the headphone apparatus for the right ear side of a listener 1 is shown for simplified illustration. This similarly applies to the other embodiments hereinafter described. Naturally, also the other portion of the headphone apparatus for the left ear side of the listener 1 is configured similarly.

Referring first to FIG. 1, the headphone apparatus is mounted on the listener 1 such that the right ear of the listener 1 is covered with a headphone housing (housing section) 2 for the right ear. A headphone driver unit (hereinafter referred to simply as driver) 11 is provided on the inner side of the headphone housing 2 and serves as an electroacoustic conversion section for reproducing a sound signal in the form of an electric signal into an acoustic signal.

A sound signal input terminal 12 receives a sound signal S of an object of listening. The sound signal input terminal 12 is formed from a headphone plug for being inserted into a headphone jack of a portable music reproduction apparatus. A noise reduction apparatus section 20 is interposed in a sound signal transmission line between the sound signal input terminal 12 and the driver 11 for the left and right ears. The noise reduction apparatus section 20 includes a power amplifier 13, a microphone 21 serving as a sound collection section and an acousto-electric conversion section described later, a microphone amplifier 22, a FB filter circuit 23 for noise reduction, a memory 24, and the like.

Though not shown, the noise reduction apparatus section 20 is connected to the driver 11, microphone 21 and headphone plug which forms the sound signal input terminal 12 by a connection cable. The connection cable has connection terminal portions 20*a*, 20*b* and 20*c* at which the connection cable is connected to the noise reduction apparatus section 20.

In the present first embodiment of FIG. 1, in a music listening environment of the listener 1, noise entering from a noise source 3 outside the headphone housing 2 to a music listening position of the listener 1 inside the headphone housing 2 is reduced by the feedback system so that the listener 1 can enjoy music in a good environment.

In the noise reduction system of the feedback type, noise at an acoustic synthesis position or noise cancel point Pc at which the noise and acoustic reproduction sound of a noise reduction sound signal are synthesized and which is the sound listening position of the listener 1 is collected by a microphone.

Accordingly, in the present first embodiment, the microphone 21 for noise collection is provided at the noise cancel point Pc which is on the inner side of the headphone housing 2 as seen in FIG. 1. Since the position of the microphone 21 serves as a control point, the noise cancel point Pc is usually set to a position in the proximity of the ear, that is, the front face of a diaphragm of the driver 11 taking a noise reduction effect into consideration. Thus, the microphone 21 is provided at this position.

Then, a reversed phase component to noise collected by the microphone 21 is generated as a noise reduction sound signal by a noise reduction sound signal generation section. Then, the generated noise reduction sound signal is supplied to and acoustically reproduced by the driver 11 to reduce the noise entering the headphone housing 2 from the outside.

Here, the noise at the noise source 3 and the noise 3' entering the headphone housing 2 do not have the same characteristic. However, in the noise reproduction system of the feedback type, the noise 3' entering the headphone housing 2, that is, the noise 3' of an object of reduction, is collected by the microphone 21.

Accordingly, in the feedback system, the noise reduction sound signal generation section should generate a reversed phase component to the noise 3' collected at the noise cancel point Pc by the microphone 21 so that the noise 3' may be canceled.

In the present embodiment, the digital FB filter circuit 23 is used as the noise reduction sound signal generation section of the feedback type. In the present embodiment, since a noise reduction signal is generated by the feedback system, the digital filter circuit 23 is hereinafter referred to as FB filter circuit 23.

The FB filter circuit 23 includes a digital signal processor (DSP) 232, an A/D conversion circuit 231 provided at the preceding stage to the DSP 232, and a D/A conversion circuit 233 provided at the succeeding stage to the DSP 232.

Referring now to FIG. 2, the DSP 232 includes a digital filter circuit 301, a gain variation circuit 302, an addition circuit 303, a control circuit 304, a digital equalizer circuit 305, a transfer function Hfb multiplication circuit 306, a subtraction circuit 307 serving as a removal circuit, and a beating decision circuit 308.

An analog sound signal obtained by collection by the microphone 21 is supplied through the microphone amplifier 22 to the FB filter circuit 23, in which it is converted into a digital sound signal by the A/D conversion circuit 231. Then, the digital sound signal is supplied to the digital filter circuit 301 of the DSP 232.

The digital filter circuit 301 of the DSP 232 is provided to generate a digital noise reduction sound signal by the feedback system. The digital filter circuit 301 generates, from a digital sound signal inputted thereto, a digital noise reduction sound signal of a property according to a filter coefficient as a parameter set in the digital sound signal. The filter coefficient to be set to the digital filter circuit 301 is read out from the memory 24 by the control circuit 304 and supplied to the digital filter circuit 301 in the present embodiment.

In the present embodiment, such a plurality of filter coefficients or a plurality of sets of filter coefficients as parameters as hereinafter described are stored in the memory 24 so that noise in a plurality of various different noise environments can be reduced with a noise reduction sound signal by the feedback system generated by the digital filter circuit 301 of the DSP 232.

The control circuit 304 reads out a particular one filter coefficient or a particular one set of filter coefficients from among the filter coefficients stored in the memory 24 and sets the filter coefficient or coefficients to the digital filter circuit 301.

In the present embodiment, a beating decision signal from the beating decision circuit 308 is supplied to the control circuit 304. When the control circuit 304 decides based on the beating signal from the beating decision circuit 308 that the headphone housing 2 is beaten by the user, the control circuit 304 changes the predetermined one filter coefficient or predetermined one set of filter coefficients to be read out from the memory 24 and sets the changed filter coefficient or filter coefficients to the digital filter circuit 301.

It is to be noted that, in the present embodiment, when a filter coefficient set according to a noise environment is set to the digital filter circuit 301, noise canceling filters (hereinafter referred to as an NC filter) according to the filter coefficients are formed and a corresponding noise reduction sound signal is produced. Therefore, in the following description, a state wherein an NC filter according to a noise environment is formed in the digital filter circuit 301 is referred to as noise mode, and a name according to a noise environment is applied to a noise mode as hereinafter described. Accordingly, changeover alteration of a filter coefficient corresponds to alteration of the noise mode (hereinafter referred to sometimes as mode).

In the present embodiment, every time beating of the headphone housing 2 by the user is decided by the beating decision circuit 308, the control circuit 304 alters the filter coefficients to be read out from the memory 24 to change over the noise mode. Accordingly, in the present embodiment, every time the user beats the headphone housing 2, the noise mode is cyclically altered to a noise mode according to the filter coefficients stored in the memory 24.

Then, the digital filter circuit 301 of the DSP 232 generates a digital noise reduction sound signal according to a filter coefficient selectively read out from the memory 24 through the control circuit 304 and set in such a manner as described above.

Then, the digital noise reduction sound signal generated by the digital filter circuit 301 is supplied to the addition circuit 303 through the gain variation circuit 302 as seen in FIG. 2. In the present embodiment, the gain variation circuit 302 controls the gain upon changeover alteration of the noise mode under the control of the control circuit 304 as hereinafter described.

On the other hand, a sound signal S such as, for example, a music signal of an object of listening received through the sound signal input terminal 12 is converted into a digital sound signal by an A/D conversion circuit 25 and then supplied to the digital equalizer circuit 305 of the DSP 232. The sound signal S undergoes sound quality correction such as amplitude-frequency characteristic correction or phase-frequency characteristic correction or both of them by the digital equalizer circuit 305.

In the case of the noise reduction apparatus of the feedback type, when the filter coefficient of the digital filter circuit 301 is altered to alter the noise reduction curve or noise reduction characteristic, the sound signal S of the object of listening inputted from the outside is subject to the influence corresponding to the frequency curve or the frequency characteristic of the noise reduction effect. Therefore, it is necessary to alter the equalizer characteristic in response to alteration of the filter coefficients of the digital filter circuit 301.

Therefore, in the present first embodiment, parameters for altering the equalizer characteristic of the digital equalizer circuit 305 in a corresponding relationship to each of a plurality of filter coefficients set to the digital filter circuit 301 are stored in the memory 24. Then, the control circuit 304 supplies a parameter according to alteration of a filter coefficient to the digital equalizer circuit 305 to alter the equalizer characteristic.

Further, as hereinafter described, in the present embodiment, an instruction to alter the equalizer characteristic of the digital equalizer circuit 305 can be issued by the user. Therefore, in the present embodiment, when the headphone housing 2 is beaten once, it is decided that the single beating is an alteration input command of the noise mode, but when the headphone housing 2 is beaten twice, it is decided that this is an alteration instruction command of the equalizer characteristic.

An output sound signal of the digital equalizer circuit 305 is supplied to the addition circuit 303, by which it is added to a noise reduction sound signal from the gain variation circuit 302. Then, the sum signal is supplied as an output of the DSP 232 to the D/A conversion circuit 233, by which it is converted into an analog sound signal. Then, the analog sound signal is supplied as an output signal of the FB filter circuit 23 to the power amplifier 13. Then, the sound signal from the power amplifier 13 is supplied to the driver 11, by which it is reproduced acoustically so that the reproduction sound is radiated to the two ears (in FIGS. 1 and 2, only the right ear is shown) of the listener 1.

The sound radiated by the acoustic reproduction from the driver 11 includes an acoustic reproduction component originating from the noise reproduction sound signal generated by the FB filter circuit 23. The acoustic reproduction component originating from the noise reduction sound signal from within the sound radiated by the acoustic reproduction by the driver 11 is acoustically synthesized with the noise 3' so that the noise 3' is reduced or cancelled at the noise cancel point Pc.

Figure 3:
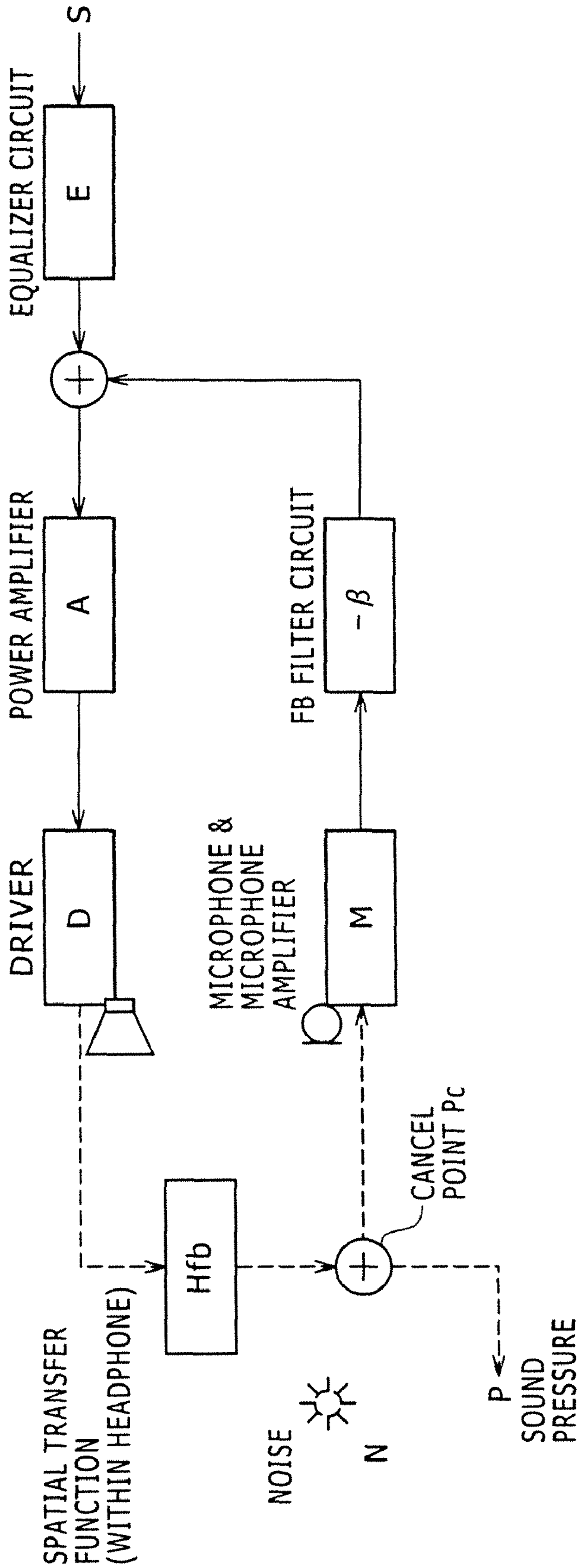
FIG. 3 is a block diagram showing a configuration of a noise reduction apparatus section in the sound outputting apparatus according to the first embodiment of the present invention using a transfer function.

A noise reduction operation of the noise reduction apparatus section 20 of the feedback type described above is described using a transfer function with reference to FIG. 3.

FIG. 3 shows a block diagram wherein different components of the noise reduction apparatus section 20 shown in FIG. 1 are represented using their transfer functions. Referring to FIG. 3, reference character A denotes the transfer function of the power amplifier 13; D the transfer function of the driver 11; M the transfer function of the microphone 21 and the microphone amplifier 22; $-\beta$ the transfer function of a filter (digital filter circuit 301) defined for feedback; Hfb the transfer function of the space from the driver 11 to the microphone 21; and E the transfer function of the digital equalizer circuit 305 applied to the sound signal S of the listening object. It is to be noted that the transfer functions given above are represented in complex representations.

Further, in FIG. 3, reference character N denotes noise entering a location at or around the position of the microphone 21 in the headphone housing 2 from an external noise source, and P a sound pressure arriving at the ear of the listener 1. It is to be noted that the cause of the fact that external noise is transmitted to the inside of the headphone housing 2 is that, for example, the noise leaks as a sound pressure through a gap at an ear pad portion or, as a result of vibration of the headphone housing 2 caused by a sound pressure, sound is transmitted to the inside of the headphone housing 2.

Where the noise reduction apparatus section 20 is represented in such a manner as seen in FIG. 3, the blocks of FIG. 3 can be represented by an expression 1 in FIG. 4. If attention is paid to the noise N in the expression 1, then it can be recognized that the noise N is attenuated to $1/(1+ADHfbM\beta)$. However, in order for the system of the expression 1 to operate stably as a noise cancel mechanism in the noise reproduction object frequency band, it is necessary to satisfy the expression 2 of FIG. 4.

Generally, it is necessary for the absolute value of the product of the transfer functions in the noise reduction system of the feedback type to be higher than 1 ($1 \ll |ADHfbM\beta|$). Further, together with Nyquist stability decision in the classic control theory, the stability of the system relating to the expression 2 of FIG. 4 can be interpreted in the following manner.

Figure 5:
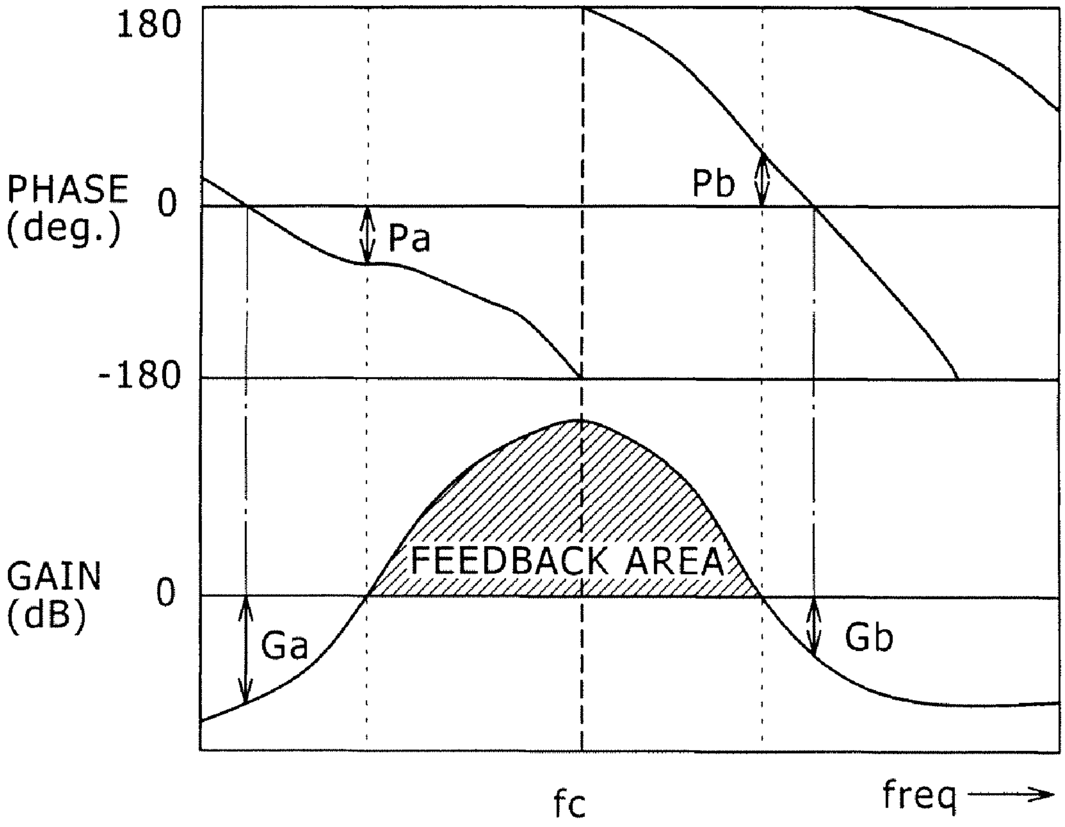

Referring to FIG. 3, an "open loop" of a transfer function ($-ADHfbM\beta$) where the loop portion which relates to the noise N, that is, the loop portion from the microphone 21 to the driver 11, is cut at one place is considered. This open loop has such characteristics as represented by a board chart shown in FIG. 5.

Where this open loop is determined as an object, the condition that satisfies the expression 2 above, from the Nyquist stability decision, that it is necessary to satisfy the following two conditions that, in FIG. 5, when a point at which the phase is 0 degree is passed, the gain must be lower than 0 dB, and when the gain is higher than 0 dB, a point at which the phase is 0 degree must not be included.

If the two conditions above are not satisfied, then positive feedback is applied to the loop, which gives rise to oscillation (howling). In FIG. 5, reference characters Pa and Pb represent phase margins, and Ga and Gb represent gain margins. Where those margins are small, the possibility of oscillation increases by a personal error or a dispersion in mounting of the headphone.

Now, reproduction of necessary sound from the driver of the headphone is described in addition to the noise reduction function.

The sound signal S of an object of listening in FIG. 3 actually is a general term of signals to be originally reproduced by the driver 11 of the headphone apparatus such as sound of a microphone outside the housing (the sound is used for a hearing adding function) and a sound signal through communication (the sound is used for a headset) in addition of a music signal.

If attention is paid to the sound signal S in the expression 1 given hereinabove, then if the equalizer E is set as represented by the expression 3 illustrated in FIG. 4, then the sound pressure P is represented as given by the expression 4 in FIG. 4.

Accordingly, if the position of the microphone 21 is very proximate to the ear, then since Hfb is the transfer function from the driver 11 to the microphone 21 (ear) and A and D are transfer functions of the characteristic of the power amplifier 13 and the driver 11, respectively, it can be recognized that characteristics similar to those of an ordinary headphone which does not have a noise reduction function are obtained. It is to be noted that, at this time, the equalizer E of the power amplifier 13 has a characteristic substantially similar to the open loop characteristic as viewed on the frequency axis.

The headphone apparatus of the configuration described above with reference to FIG. 1 allows the user to listen to a sound signal of an object of listening without any trouble while reducing noise in such a manner as described above. It is to be noted, however, that, in this instance, in order to achieve a sufficient noise reduction effect, it is necessary to set a filter coefficient according to a characteristic of noise transmitted from the noise source 3 to the inside of the headphone housing 2 in the digital filter formed from the DSP 232.

As described hereinabove, various noise environments wherein noise is generated exist, and the frequency characteristic or the phase characteristic of noise relies upon the respective noise environment. Therefore, it is difficult to expect to use a single filter coefficient to obtain a sufficient noise reduction effect in all noise environments.

Therefore, in the present embodiment, a plurality of or a plurality of sets of filter coefficients according to various noise environments are prepared and stored in advance in the memory 24. Then, one of the filter coefficients which is considered appropriate is selectively read out from the memory 24 and is set to the digital filter circuit 301 formed in the DSP 232 of the FB filter circuit 23.

It is desirable to calculate, for the filter coefficients to be set to the digital filter circuit 301, suitable values with which noise collected in various noise environments can be reduced or canceled and store the values into the memory 24 in advance. For example, suitable filter coefficient values with which noise collected in various noise environments such as, for example, on a platform of a railway station, at an airport, in a train traveling on the ground, in a train of a subway, in a crowd in a town or in a large store can be reduced or canceled are calculated and stored into the memory 24 in advance.

In particular, a set of filter coefficients for each of a plurality of noise environments, that is, for each of a plurality of different noise modes, are calculated and stored into the memory 24 in advance.

Then, in the present first embodiment, selection of a suitable one of the filter coefficients or a suitable one of the sets of coefficients stored in the memory 24 is performed by a manual operation by the user.

In the present embodiment, the manual operation of the user is provided by beating of the headphone housing 2. Further, in the present embodiment, a single beating operation of the headphone housing 2 is determined as an alteration instruction of the filter coefficient, that is, an alteration instruction of the noise mode, and two successive beating operations of the headphone housing 2 are determined as an alteration instruction of the equalizer characteristic.

Alteration of the equalizer characteristic based on the alteration instruction of the equalizer characteristic by two successive beating operations of the headphone housing 2 is different from alteration of the equalizer characteristic according to alteration of the noise mode of the noise reproduction system of the feedback type described hereinabove. In particular, the alteration instruction of the equalizer characteristic in this instance is for selecting an equalizer characteristic (amplitude-frequency characteristic, a phase-frequency characteristic or both of such characteristics) suitable for a genre of a musical piece which the user is listening to such as, for example, classic, jazz, pops, rock or Japanese popular song.

A plurality of parameters to be supplied to the digital equalizer circuit 305 in order to produce equalizer characteristics according to such a plurality of genres as described above are stored in advance in the memory 24. Then, every time the headphone housing 2 is beaten twice by the user, the control circuit 304 reads out parameters for the individual genres successively and cyclically from the memory 24 and supplies them to the digital equalizer circuit 305. In particular, every time the headphone housing 2 is beaten twice, the control circuit 304 successively reads out the parameters for equalizer characteristic alteration like the parameter for classic music→parameter for jazz→parameter for pops→parameter for rock→parameter for Japanese popular song and supplies the read out parameters to the digital equalizer circuit 305.

Thereupon, though not shown, a voice message representing a parameter of which genre is set to the digital equalizer circuit 305, for example, a voice message of "classic music", may be added to the sound signal to be supplied to the driver 11 every time the equalizer characteristic is altered based on a decision of two beating operations of the headphone housing 2.

The decision of beating of the headphone housing 2 in the present embodiment is performed based on a collected sound signal from the microphone 21. The collected sound signal from the microphone 21 in this instance is influenced not only by an external sound signal such as a component of reproduced music to be listened to or communication sound but also by a noise reduction effect. When the user beats the headphone housing 2 twice, although the sound generated from the thus beaten headphone housing 2 is collected by the microphone 21, the sound volume thereof is reduced by the noise reduction effect. Further, since reproduction sound is emitted from the driver 11 simultaneously, there is the possibility also that the beating sound of the headphone housing 2 may be covered with the reproduction sound. Therefore, it is difficult to detect beating of the headphone housing 2 immediately from the collected sound signal from the microphone 21.

Therefore, in the present embodiment, acoustic reproduction sound of the sound signal S is removed so that a beating operation can be decided with certainty.

Further, where the transfer function from the driver 11 to the microphone 21 or the ear is represented by Hfb, a filter Hfb_nc is calculated in advance by multiplying a factor of the transfer function Hfb by a frequency characteristic influence of an external sound signal by a noise reduction effect in a currently selected noise mode. Then, upon actual application, a sound signal of a reproduction object is passed through the digital equalizer circuit 305 and then multiplied by the filter Hfb_nc, whereafter it is subtracted from an output signal of the microphone 21. Then, a beating decision is made based on a resulting subtraction output signal.

In other words, a sound signal emitted from the driver 11 at the position of the microphone 21 is simulated as accurately as possible and is subtracted from sound at the position of the microphone 21 to remove a component of the sound signal S from the collected sound signal of the microphone 21.

Thus, in the present embodiment, the collected sound signal from the microphone 21 is converted into a digital sound signal by the A/D conversion circuit 231 and then supplied to the subtraction circuit 307.

Meanwhile, the sound signal S from the digital equalizer circuit 305 is supplied to the filter Hfb_nc multiplication circuit 306, by which it is multiplied by the filter Hfb_nc which is determined taking the transfer function Hfb into consideration. Then, a result of the multiplication is supplied to the subtraction circuit 307, by which the result of multiplication is subtracted from the collected sound signal from the microphone 21 to remove the component of the sound signal S included in the collected sound signal.

Then, the collected sound signal of the microphone 21 from which the component of the sound signal S is removed from the subtraction circuit 307 is supplied to the beating decision circuit 308. The beating decision circuit 308 decides whether or not the collected sound signal from the microphone 21 includes a sound signal component or an oscillation component when the headphone housing 2 is beaten and further decides the number of times of beating depending upon how many components are included within a predetermined period of time. Then, the beating decision circuit 308 supplies the decision result to the control circuit 304.

Although the subtraction result obtained from the subtraction circuit 307 includes environmental noise, sound transmitted through the headphone housing 2 when the user beats the headphone housing 2 is generally louder than the environmental noise and usually the environmental noise does not include pulsed sound like the beating sound when the headphone housing 2 is beaten. Therefore, such environmental noise as described above is not recognized in error as sound upon beating.

While an example of a particular configuration of the beating decision circuit 308 is hereinafter described in detail, not only a hardware configuration but also a configuration of software processing of an output signal of the subtraction circuit 307 can be applied. Further, where a software processing configuration is employed, it may additionally include also processing of the transfer function Hfb multiplication circuit 306 and the subtraction circuit 307.

In the present embodiment, every time the control circuit 304 receives a decision result of one beating operation which is a changeover instruction operation of the noise mode as a result of the decision of the beating decision circuit 308, the control circuit 304 alters the setting of the filter coefficients to be read out from the memory 24 and supplies the altered filter coefficients to the digital filter circuit 301.

Figure 6:
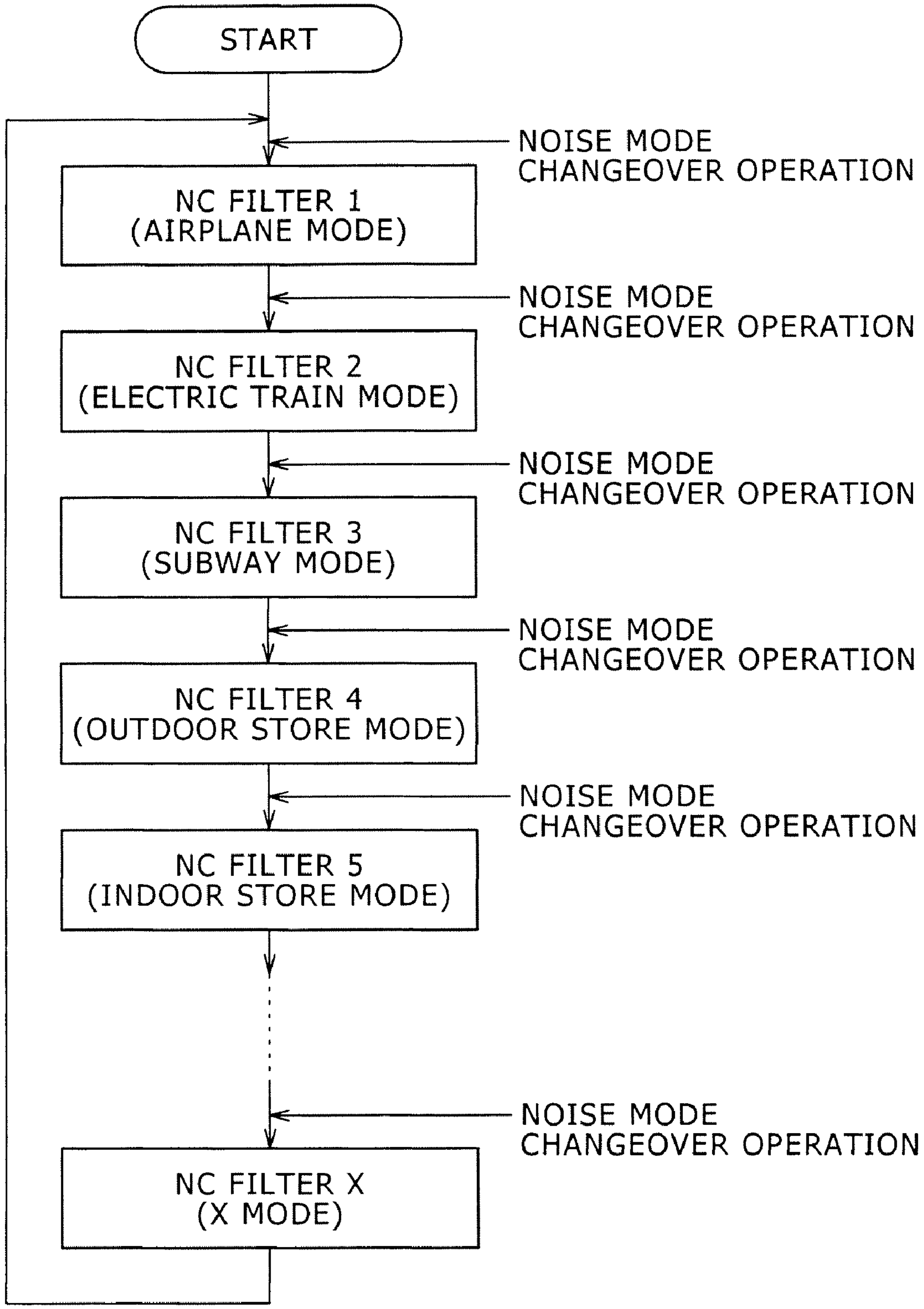
FIG. 6 is a flow chart illustrating operation of the sound outputting apparatus according to the first embodiment of the present invention.

In particular, as seen in FIG. 6, every time the control circuit 304 detects a noise changeover instruction operation by one beating operation of the headphone housing 2, the control circuit 304 alters the filter coefficients to be read out from the memory 24 and supplied to the digital filter circuit 301 thereby to change over and alter the filter characteristics of the NC filter formed from the digital filter circuit 301.

Upon reading out of the filter coefficients or sets of filter coefficients according to the noise modes stored in the memory 24, a readout order is determined in an order of the noise modes in advance, and when it is decided that a changeover alteration operation instruction of the noise mode is issued, the filter coefficients are successively and cyclically read out in accordance with the readout order.

For example, the readout order illustrated in FIG. 6 is determined such that the first noise mode is an air plane mode which is a noise function mode in an airplane; the second noise mode is an electric train mode which is a noise environment mode in an electric train; the third noise mode is a subway mode which is a noise environment mode in a subway; the fourth noise mode is an outdoor store mode which is a noise environment mode outdoors around a store; the fifth noise mode is an indoor store mode which is a noise environment mode indoors of a store; . . . . An NC filter 1, an NC filter 2, an NC filter 3, an NC filter 4, an NC filter 5, . . . according to the noise modes are formed by the digital filter circuit 301 in accordance with the noise modes.

Figure 7:
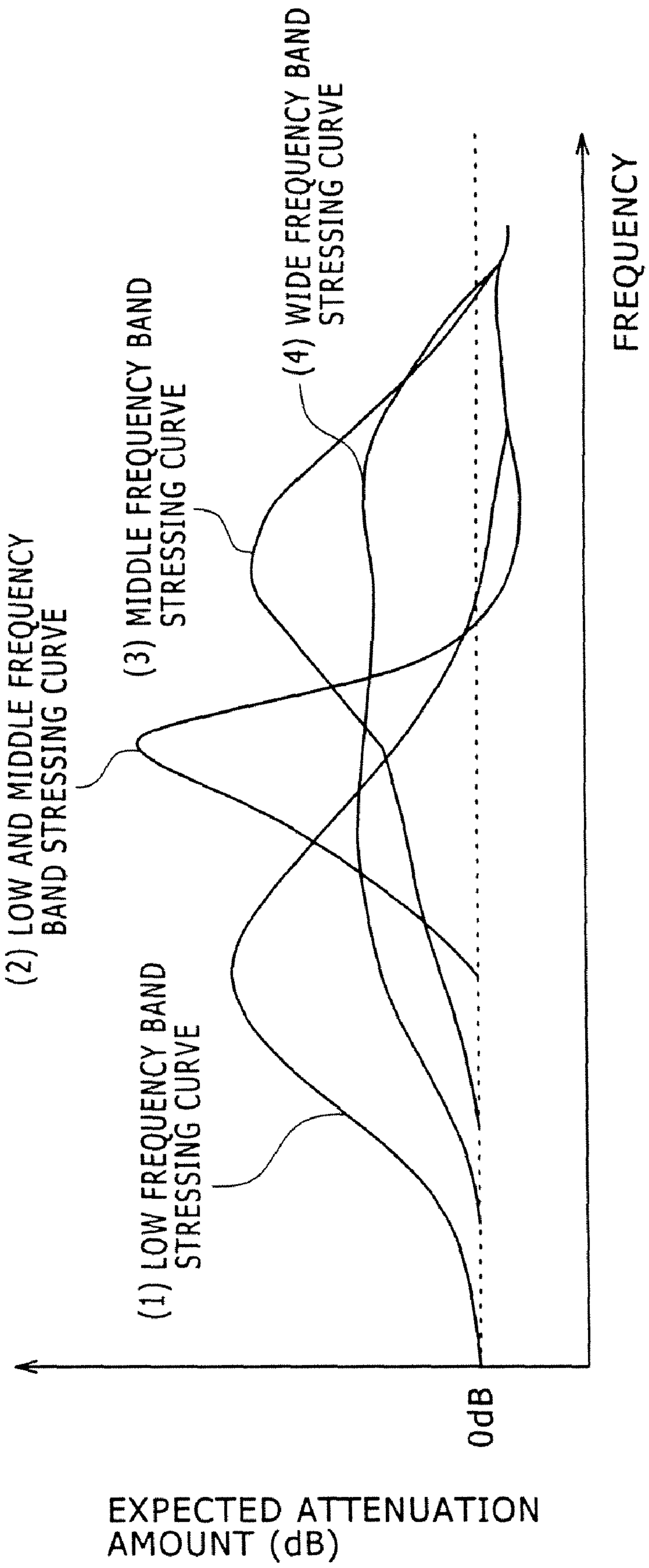
FIGS. 7 and 8 are waveform diagrams illustrating operation of the sound outputting apparatus according to the first embodiment of the present invention.

For example, it is assumed that, as a simple example, sets of parameters with which four different noise reduction effects as represented by "noise reduction curves (noise attenuation characteristics)" illustrated in FIG. 7, that is, sets of filter coefficients, are written in the memory 24. In the example of FIG. 7, for noise characteristics of four different noise modes where noise is distributed principally in a low frequency band, a middle low frequency band, a middle frequency band and a wide frequency band, sets of filter coefficients with which curve characteristics for decreasing noise in the individual node modes are stored in the memory 24.

In this instance, where, as seen in FIG. 7, a filter coefficient with which a noise reduction characteristic of the low frequency band stressing curve used for noise reduction where noise is distributed principally in the low frequency band, another filter coefficient with which a noise reduction characteristic of the middle low frequency band stressing curve used for noise reduction where noise is distributed principally in the middle low frequency band, a further filter coefficient with which a noise reduction characteristic of the middle frequency band stressing curve used for noise reduction where noise is distributed principally in the middle frequency band and a still further filter coefficient with which a noise reduction characteristic of the wide frequency band stressing curve used for noise reduction where noise is distributed principally in the wide frequency band are determined as first, second, third and fourth filter coefficients, respectively. And the filter coefficient to be read out from the memory 24 is changed like the first→second→third→fourth→first→ . . . every time a push switch is depressed to issue an alteration operation instruction of the filter coefficient.

The listener 1 would change over the noise mode in this manner and confirm the noise reduction effect in each noise mode with the ears of the user itself. Then, if the user feels that a sufficient noise reduction effect is achieved, then the user would stop later depression of the mode changeover button so that the noise mode in which the filter coefficient is read out then may be maintained. Consequently, the memory controller continually reads out the filter coefficient read out at the point of time also after then and controls the readout state of the filter coefficient to that of the noise mode selected by the user.

It is to be noted that the example described above with reference to FIG. 7 corresponds to a case wherein not noise in individual noise environments is actually measured to set corresponding filter coefficients but states wherein noise is distributed in four different frequency bands including a low frequency band, a low middle frequency band, a middle frequency band and wide frequency band are assumed and filter coefficients are set so as to obtain curve characteristics for reducing noise in the individual cases and stored in the memory 24.

Also where such filters set according to simple noise modes as described above are used, with the noise reduction apparatus of the present embodiment, a filter coefficient suitable for each noise environment can be selected. Therefore, a more effective noise reduction effect than that where a filter coefficient is determined fixedly as in the case of the analog filter system in the past can be obtained.

It is to be noted that also alteration of the equalizer characteristic based on a twice beating decision of the headphone housing 2 by the control circuit 304 can be performed similarly as in the case of the alteration of the noise mode described above.

Further, in the present embodiment, in order to allow the listener to confirm a noise reduction effect in each noise mode upon changeover alteration of the noise mode with a higher degree of certainty, the control circuit 304 performs its control in the following manner upon changeover alteration of the noise mode.

FIRST EXAMPLE

Figure 8:
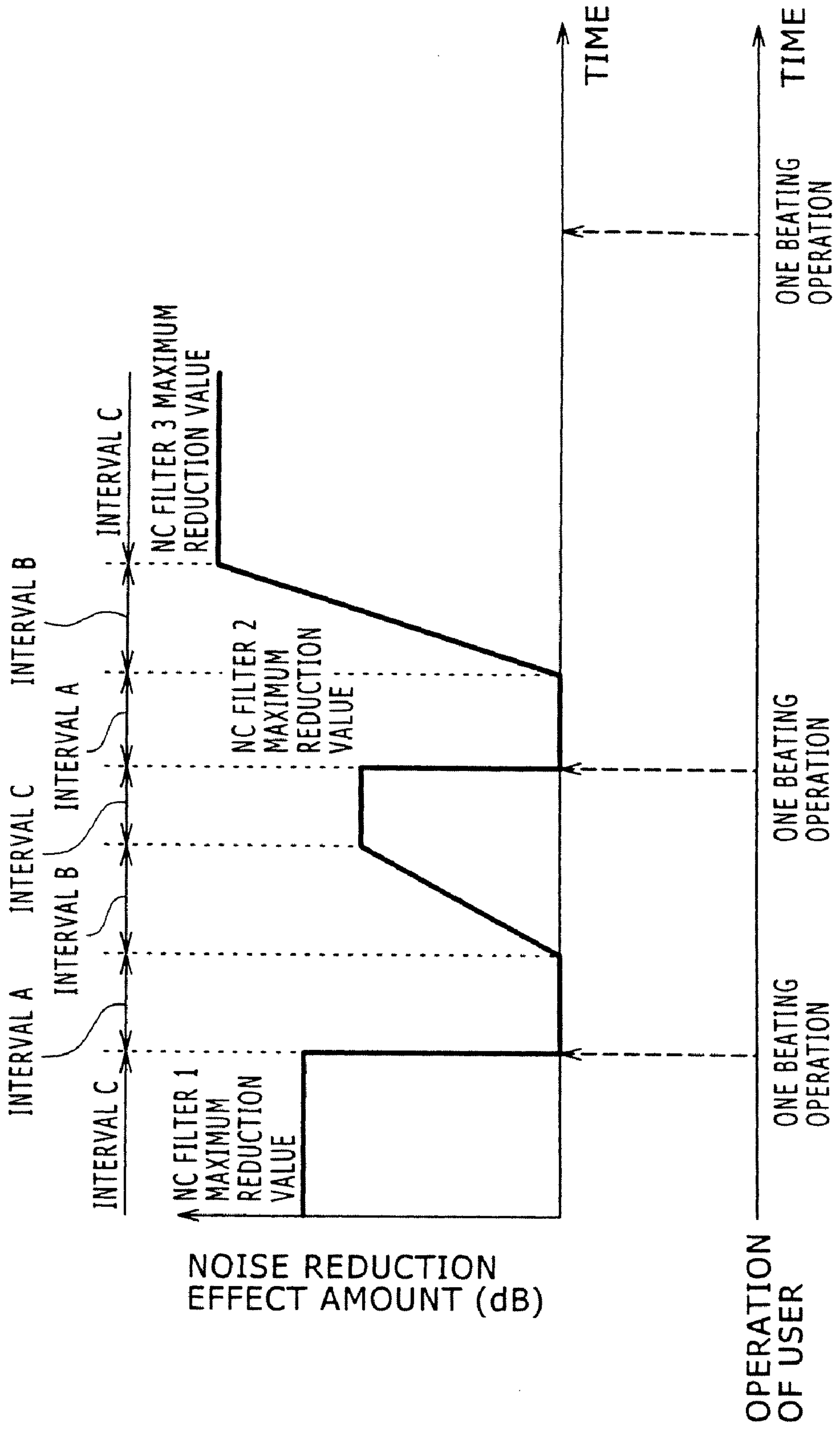

FIG. 8 illustrates a first example of control upon noise mode changeover alteration of the control circuit 304 in the present embodiment.

In the present example, when it is decided that a noise mode changeover instruction operation is performed by a single beating operation of the headphone housing 2, the control circuit 304 not only merely alters the filter coefficient to change over the NC filter formed from the digital filter circuit 301 but also reduces the noise reduction effect by the digital filter circuit 301 to zero immediately after a depression operation of the mode changeover button is performed as seen in FIG. 7, thereby to provide a noise reduction effect off interval A, within which the noise reduction effect is off, for a predetermined period of time.

Then, after the noise reduction effect off interval A comes to an end, the control circuit 304 provides a noise reduction effect gradually increasing interval B of a fixed period of time within which the noise reduction effect by the NC filter of the noise mode after the changeover is gradually increased to its maximum value.

Then, after the noise reduction effect gradually increasing interval B comes to an end, the control circuit 304 fixes the noise reduction effect by the NC filter of the mode after the changeover at its maximum value. In FIG. 8, the interval within which the noise reduction effect is fixed at its maximum value is represented as interval C.

The noise reduction effect off interval A and the noise reduction effect gradually increasing interval B are individually set to appropriate lengths. For example, the interval A is set to three seconds, and the interval B is set to four seconds. The interval C is defined by an end point provided by a point of time at which the mode changeover button is depressed next and is not fixed.

It is not be noted that, while, in the present embodiment, the noise reduction effect gradually increasing interval B is set as a fixed period of time, since the maximum values of the noise reduction amount of the NC filters in the individual noise modes are not equal to each other, the gradient of the gradual increase of the noise reduction effect differs depending upon the maximum value of the noise reduction amount of the NC filter in the noise modes.

Figure 9:
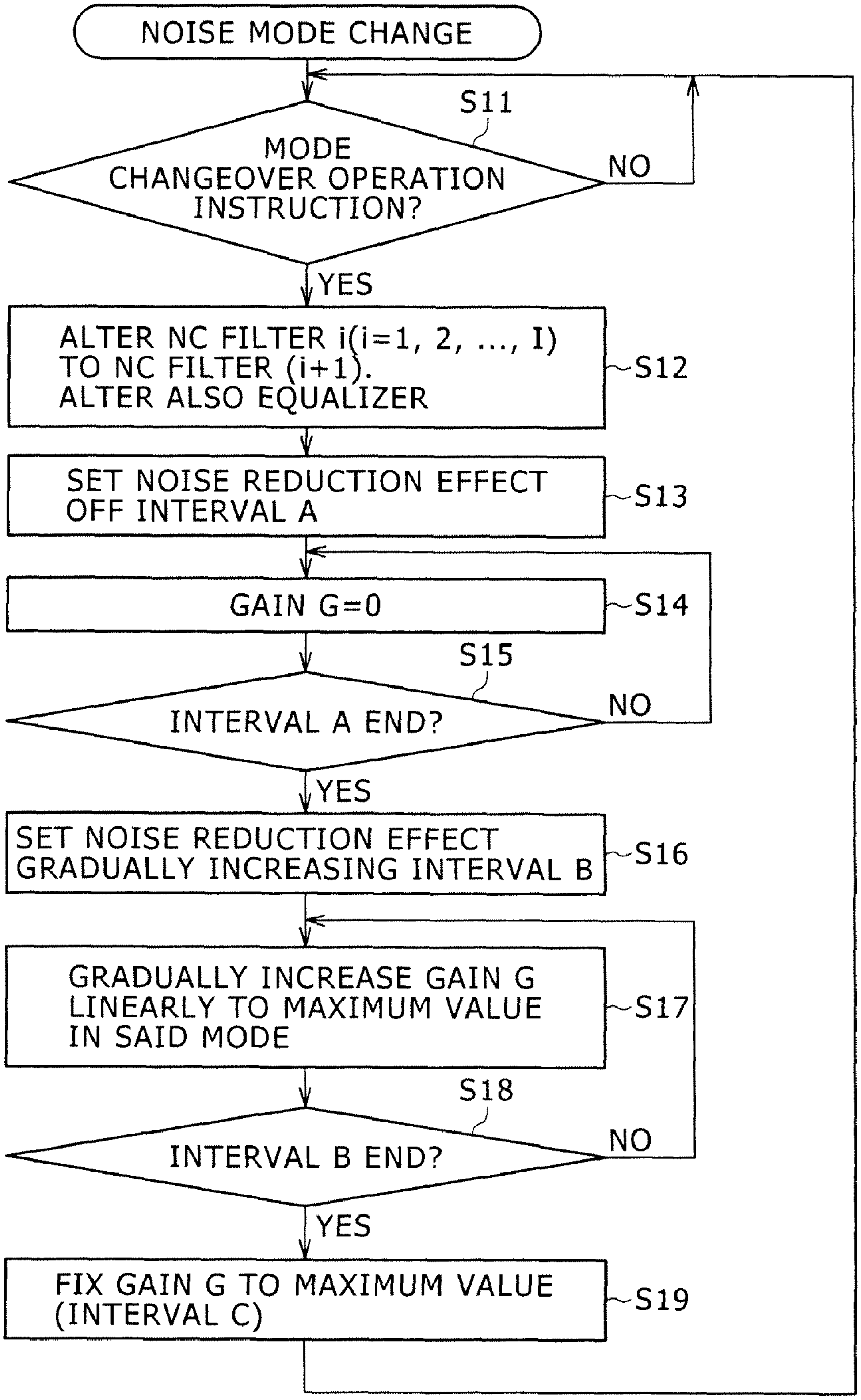
FIG. 9 is a flow chart illustrating operation of the sound outputting apparatus according to the first embodiment of the present invention.

A flow chart of control by the control circuit 304 in the case of the first example is shown in FIG. 9. Referring to FIG. 9, the control circuit 304 supervises decision result information from the beating decision circuit 308 to decide whether or not a changeover alteration operation instruction of the noise mode is issued by one beating operation of the headphone housing 2 (step S11).

If it is decided at step S11 that a changeover alteration operation instruction of the noise mode is not issued, then the control circuit 304 repeats the process at step S11 to wait that a changeover operation instruction of the noise mode is issued.

If it is decided at step S11 that a changeover alteration operation instruction of the noise mode is issued, then the control circuit 304 alters the set of filters to be read out from the memory 24 to filter coefficients of NC filters of the next order different from that till now and supplies the altered filters to the digital filter circuit 301 (step S12).

At this time, as described hereinabove, in the case of the noise reduction process of the feedback type of the present embodiment, it is necessary to control also the equalizer characteristic regarding the sound signal S in response to a variation of the noise reduction effect. Thus, the control circuit 304 controls the equalizer characteristic of the digital equalizer circuit 305 in accordance with gain control of the noise reduction effect in each of the noise reduction effect off interval A and the noise reduction effect gradually increasing interval B.

Then, the control circuit 304 sets the noise reduction effect off interval A by means of a timer (step S13) and controls the gain G of the gain variation circuit 302 to zero (step S14). Then, the control circuit 304 supervises the timer to decide whether or not the noise reduction effect off interval A comes to an end (step S15). However, if the noise reduction effect off interval A does not come to an end, then the processing returns to step S14 so that the state of the gain G of the gain variation circuit 302 is zero is maintained.

If it is decided at step S15 that the noise reduction effect off interval A comes to an end, then the control circuit 304 sets the noise reduction effect gradually increasing interval B to the timer (step S16) and then gradually increases the gain G of the gain variation circuit 302 linearly on the dB axis so that the gain G may exhibit a maximum noise reduction amount of the NC filters in the noise mode within the noise reduction effect gradually increasing interval B (step S17).

Then, the control circuit 304 supervises the timer to decide whether or not the noise reduction effect gradually increasing interval B comes to an end (step S18). If the noise reduction effect gradually increasing interval B does not come to an end, then the processing returns to step S16, at which the gradual increase of the gain G of the gain variation circuit 302 is continued.

If it is decided at step S18 that the noise reduction effect gradually increasing interval B comes to an end, then the control circuit 304 fixes the gain G of the gain variation circuit 302 to a state of the maximum reduction amount of the NC filters in the noise mode (step S19). Thereafter, the processing returns to step S11, at which, every time a depression operation of the mode changeover button is performed, the operations described above are repeated.

Figure 10:
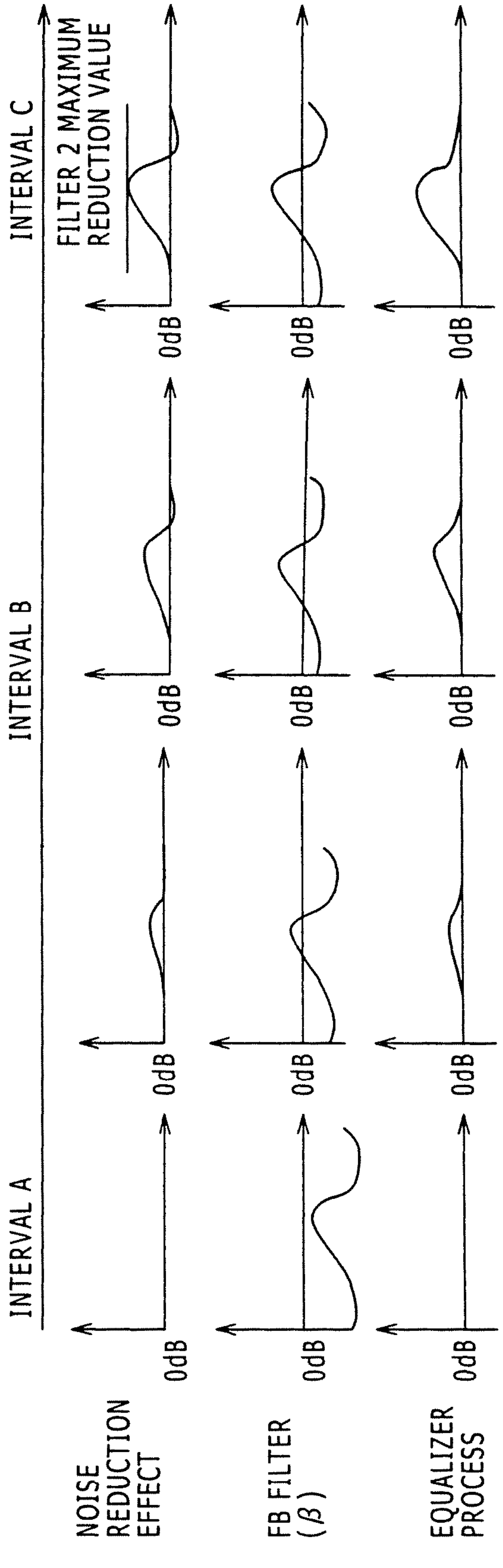
FIG. 10 is a waveform diagram illustrating operation of the sound outputting apparatus according to the first embodiment of the present invention.

FIG. 10 illustrates an example of a variation of the noise reduction effect, the NC filter characteristic in the digital filter circuit 301 and the equalizer characteristic of the digital equalizer circuit 305 in the noise reduction effect off interval A, noise reduction effect gradually increasing interval B and interval C.

SECOND EXAMPLE

In the second example, the control circuit 304 performs control upon changeover alteration of the noise mode based on a noise mode changeover instruction operation by one beating operation of the headphone housing 2 as in the case of the first example. Simultaneously, when it is found that a noise mode changeover instruction operation by a single beating operation of the headphone housing 2 is performed, the control circuit 304 notifies the user that what noise mode is entered after the mode changeover alteration. Consequently, the user can recognize the noise mode proximate to a noise environment in which the user itself is placed in advance and can confirm the noise reduction effect in the noise mode.

In this instance, in the present second example, the notification of the noise mode is performed, for example, using a method of adding a notification voice message of the noise mode to a sound signal to be supplied to the driver 11. For example, if the next mode by the noise mode changeover alteration is the airplane mode, then such a notification voice message as “airplane” is used, and if the next mode is the electric train mode, then such a notification voice message as “train” is used, but if the next mode is the subway mode, then such a notification voice message as “subway” is used.

Further, in the present second example, though not shown in the drawings, notification voice messages for the individual noise modes are stored, for example, in the memory 24. Then, the control circuit 304 selectively reads out the notification voice messages from the memory 24 at a suitable timing based on a noise mode changeover instruction operation by one beating operation of the headphone housing 2 and supplies the read out notification voice message to the addition circuit 303.

Then, in the present second example, the addition timing of a notification voice message in each noise mode to the addition circuit 303 is selected such that such addition is performed in a state wherein the noise reduction effect is in the maximum, that is, in a state wherein noise is reduced and sound can be heard readily.

Figure 11:
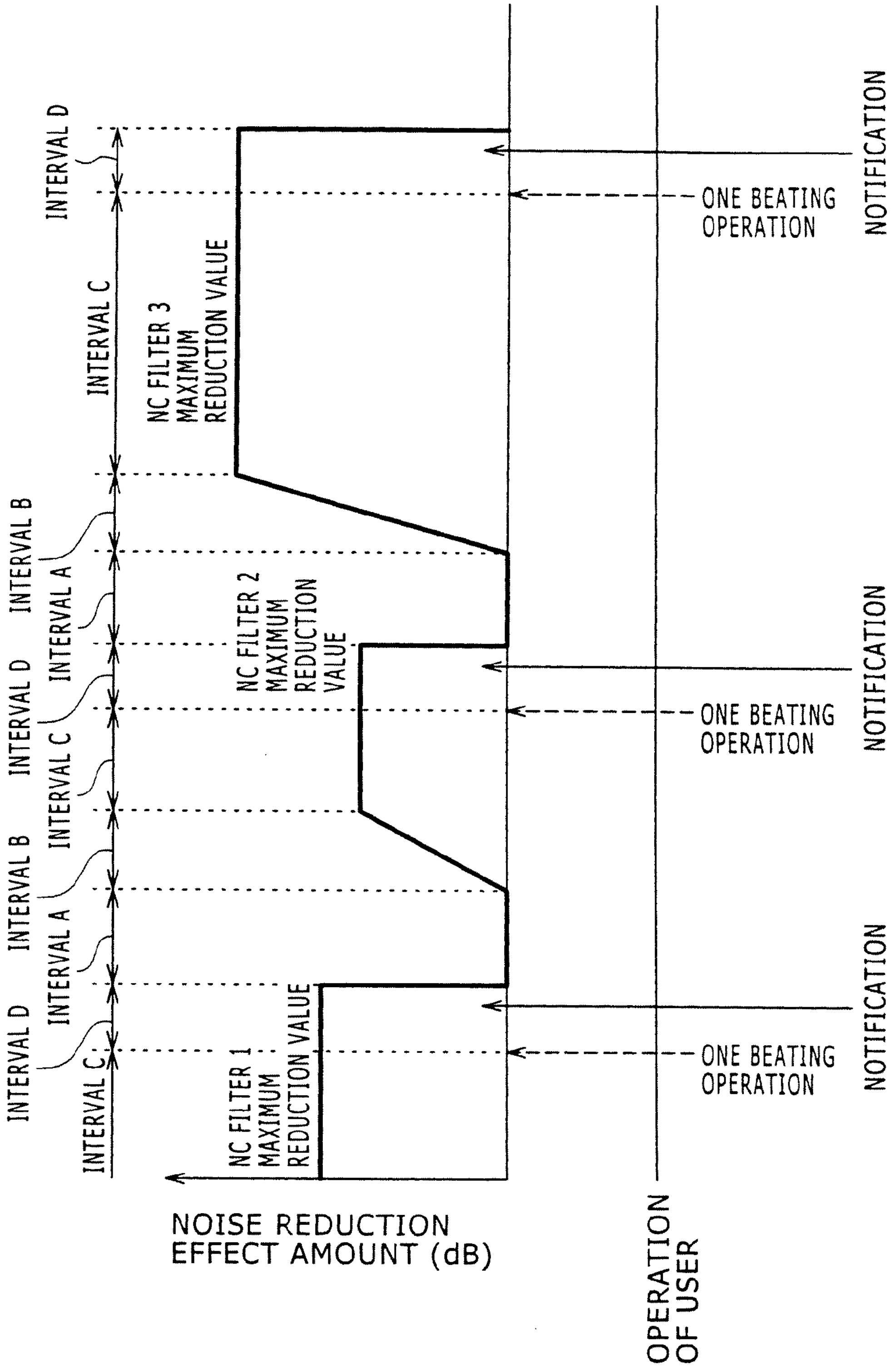
FIG. 11 is a waveform diagram illustrating another example of operation of the sound outputting apparatus according to the first embodiment of the present invention.

FIG. 11 illustrates a second example of control upon mode changeover alteration of the control circuit 304 in the present embodiment.

Referring to FIG. 11, in the present second example, not the noise reduction effect off interval A is started immediately when it is decided that a noise mode changeover operation instruction is performed by one beating operation of the headphone housing 2, but the interval C wherein the noise reduction effect by the NC filters in a noise mode before the noise mode changeover operation instruction is in the maximum is extended by a predetermined interval of time also after the noise mode changeover operation instruction to provide a period D which is used as a notification period of a next mode.

Then, within the notification interval D, the control circuit 304 reads out a notification message of a next mode from the memory 24 and adds the notification message to a sound signal by means of the addition circuit 303. Then, after the notification interval D comes to an end, the noise reduction effect off interval A described above is entered.

Figure 12:
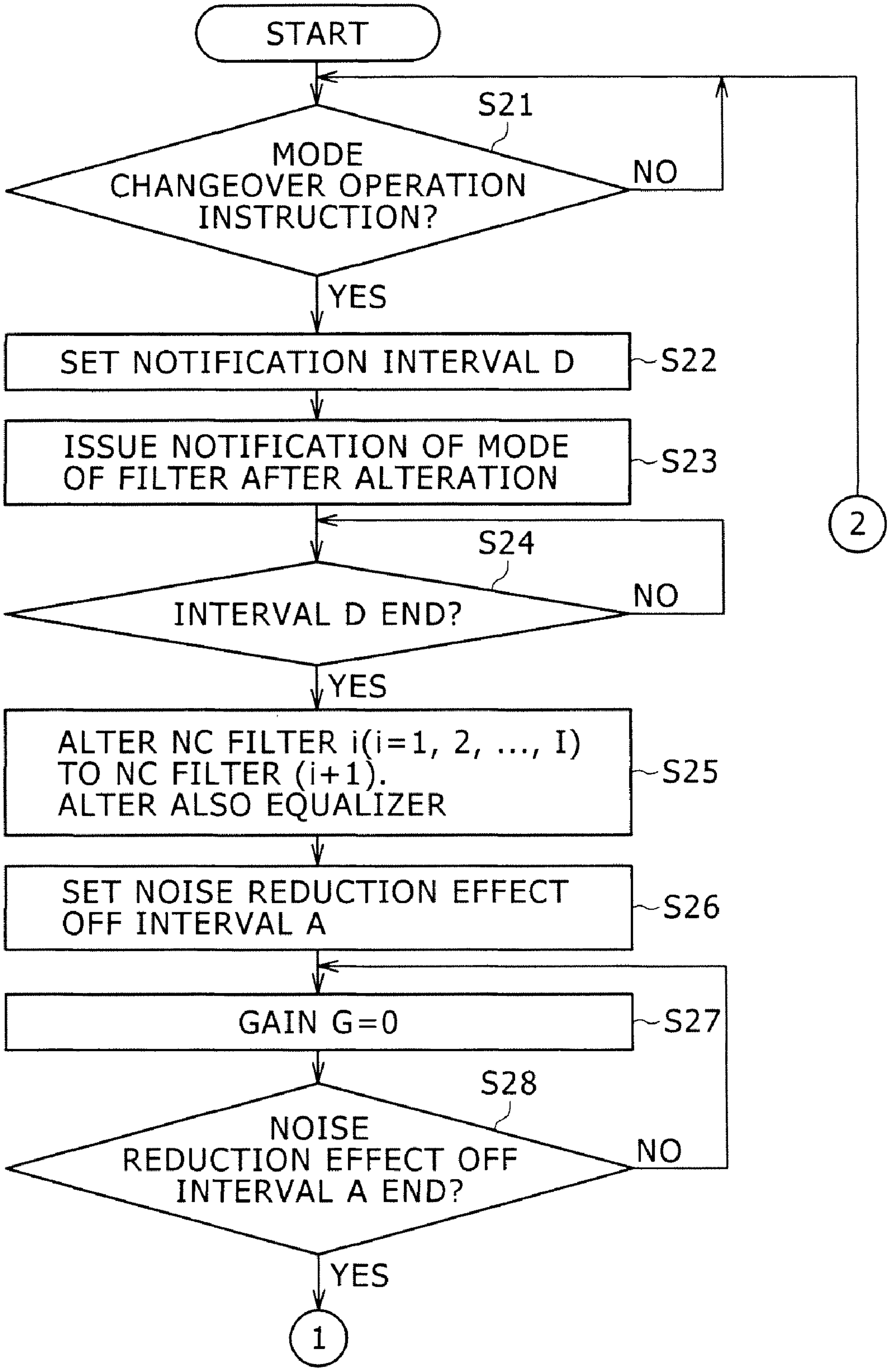
FIGS. 12 and 13 are flow charts illustrating another example of operation of the sound outputting apparatus according to the first embodiment of the present invention.
Figure 13:
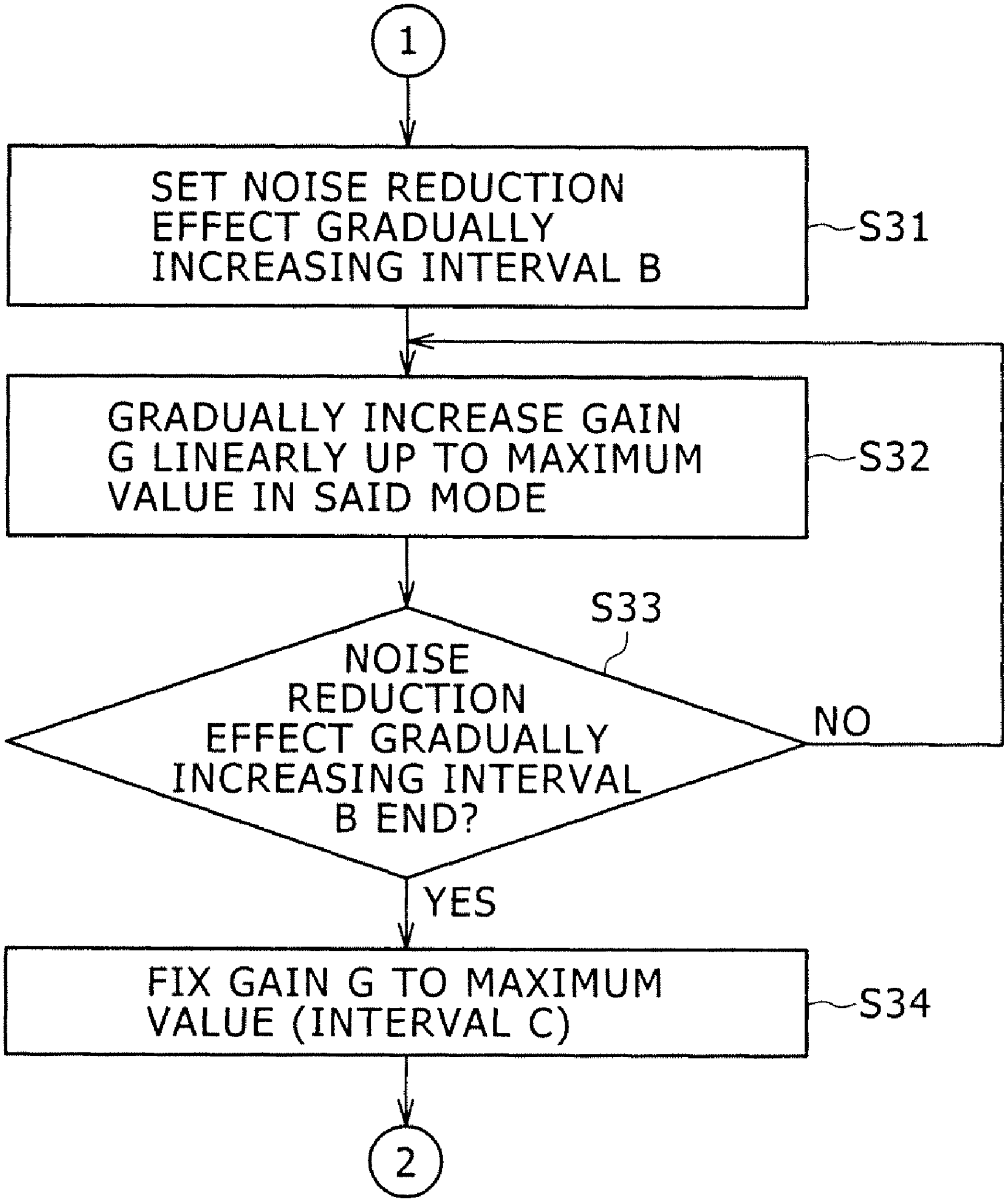

Control by the control circuit 304 in the second example is illustrated in FIGS. 12 and 13. Referring first to FIG. 12, the control circuit 304 supervises decision result information from the beating decision circuit 308 to decide whether or not a changeover operation instruction of the noise mode is issued by one beating operation of the headphone housing 2 (step S21).

If it is decided at step S21 that a changeover operation instruction of the noise mode is not issued, then the control circuit 304 repeats the process at step S21 to wait that a changeover operation instruction of the noise mode is issued.

If it is decided at step S21 that a changeover operation instruction of the noise mode is issued, then the control circuit 304 sets the notification interval D to the timer (step S22). Then, the control circuit 304 reads out data of a notification voice message of the next noise mode from the memory 24 and supplies the data to the addition circuit 303 to notify the user of the noise mode of the next order (step S23).

Then, the control circuit 304 supervises the timer to decide whether or not the notification interval D comes to an end (step S24). If the notification interval D does not come to an end, then the processing returns to step S24 to wait that the notification interval D comes to an end.

If it is decided at step S24 that the notification interval D comes to an end, then the control circuit 304 alters the set of filter coefficients to be read out from the memory 24 to filter coefficients of the NC filter of the next order different from that till then and then supplies the resulting filter coefficients to the digital filter circuit 301 (step S25).

Then, the control circuit 304 sets the noise reduction effect off interval A to the timer (step S26) and then controls the gain G of the gain variation circuit 302 to zero (step S27). Then, the control circuit 304 supervises the timer to decide whether or not the noise reduction effect off interval A comes to an end (step S28) Then, if the noise reduction effect off interval A does not come to an end, then the processing returns to step S27 to maintain the state of the gain G=0 of the gain variation circuit 302.

If it is decided at step S28 that the noise reduction effect off interval A comes to an end, then the control circuit 304 sets the noise reduction effect gradually increasing interval B to the timer (step S31 of FIG. 13). Referring now to FIG. 13, the control circuit 304 then gradually increases the gain G of the gain variation circuit 302 on the dB axis so that the gain G exhibits a maximum noise reduction amount of the NC filter in the noise mode within the noise reduction effect gradually increasing interval B (step S32).

Then, the control circuit 304 supervises the timer to decide whether or not the noise reduction effect gradually increasing interval B comes to a end (step S33) If the noise reduction effect gradually increasing interval B does not come to an end, then the processing returns to step S32 to continue the gradual increase of the gain G of the gain variation circuit 302.

If it is decided at step S33 that the noise reduction effect gradually increasing interval B comes to an end, then the control circuit 304 fixes the gain G of the gain variation circuit 302 to that of a maximum reduction amount of the NC filter in the noise mode (step S34). Thereafter, the processing returns to step S21 so that the operations described above are repeated every time a depression operation of the mode changeover button is performed.

THIRD EXAMPLE

In the first and second examples, upon changeover alteration of the noise mode, the noise reduction effect of the NC filter in the noise mode prior to the changeover alteration is changed from the maximum noise reduction amount immediately to the zero noise reduction amount. However, in the present third embodiment, the noise reduction effect of the NC filter in the noise mode prior to the changeover alteration is changed from the maximum noise reduction amount so as to be gradually decreased to the zero noise reduction amount. This is intended to prevent the noise reduction effect from disappearing suddenly until the sound becomes disagreeable to the listener.

Figure 14:
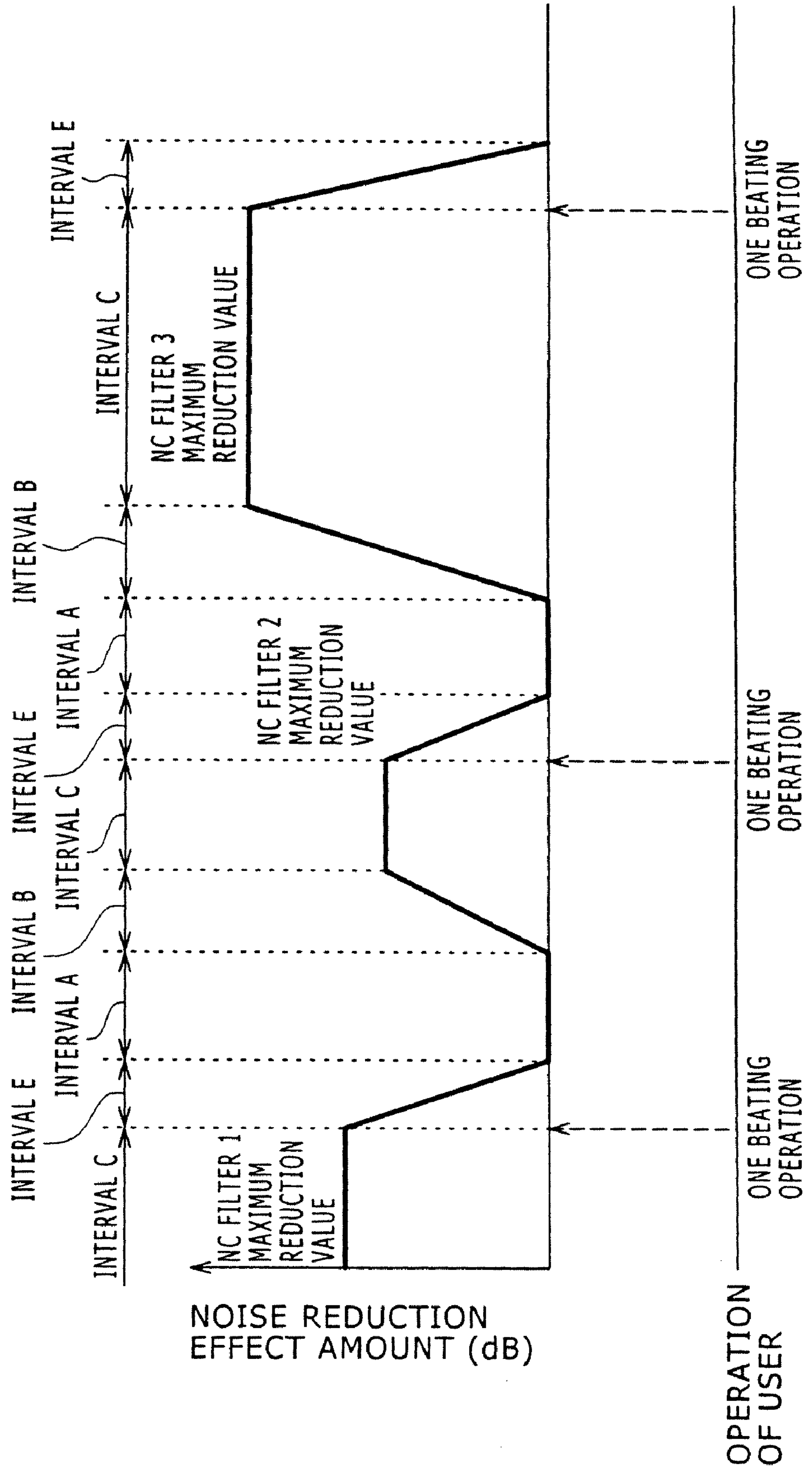
FIG. 14 is a waveform diagram illustrating a further example of operation of the sound outputting apparatus according to the first embodiment of the present invention.

FIG. 14 illustrates a case wherein the third example is applied to the first example. In particular, a noise reduction effect gradually decreasing interval E is provided next to the interval C. Then, after the noise reduction effect gradually decreasing interval E comes to an end, the noise reduction effect off interval A is entered.

It is to be noted that, where the third example is applied to the second example, the noise reduction effect gradually decreasing interval E is provided next to the notification interval D. Then, after the noise reduction effect gradually decreasing interval E comes to an end, the noise reduction effect off interval A is entered.

Further, while, in the description of the first to third examples, the noise reduction effect gradually increasing interval B is a fixed period of time, it may otherwise be a variable period set such that the gradient of the gradual increase of the noise reduction effect is fixed and the noise reduction amount of the NC filter after the mode changeover alteration gradually increases up to the its maximum value.

Further, while, in the second example, also the notification interval D is set to a predetermined period of time, after the addition of a notification voice message is completed, the notification interval D may be ended and the noise reduction effect off interval A may be entered immediately.

Further, while, in the examples described above, the gradual increase of the noise reduction effect within the noise reduction effect gradually increasing interval B is performed by control of the gain G of the gain variation circuit 302, it may be implemented by a different method. In particular, a set of filter coefficients which vary so as to implement the gradual increase of the noise reduction effect within the noise reduction effect gradually increasing interval B are stored as filter coefficients for an NC filter in the individual noise modes in the memory 24. Then, the filter coefficients are successively read out within the noise reduction effect gradually increasing interval B.

It is to be noted that, while, in the examples described above, a noise mode of a next turn is conveyed clearly to the user, it may be conveyed otherwise that changeover alteration of the noise mode is performed. In this instance, not a sound message but particular sound such as, for example, beep sound may be used for the notification.

Also the notification of the next noise mode in the order may be performed not using a notification sound message but using sound corresponding to each noise mode or using related sound such as, for example, a guide announcement at an airport or a guide announcement on a platform of a railway station.

It is to be noted that, in order to allow the listener to confirm the noise reduction effect with a higher degree of accuracy, it sometimes is favorable that the confirmation is performed in an environment wherein reproduction sound based on the sound signal S is not emitted from the driver 11. In order to cope with such a case as just described, a method is available wherein, in an environment wherein the sound signal S is not inputted, the listener operates the A/D conversion circuit 25 to confirm the noise reduction effect. Or, where the sound signal S is currently inputted and reproduced, another method may be adopted wherein, within a predetermined period of time within which the noise reduction effect can be confirmed after the changeover button of the A/D conversion circuit 25 is depressed, the sound signal S to be supplied to the DSP 232 is muted. This similarly applies to preferred embodiments of the present invention hereinafter described.

Beating Decision Method by the Beating Decision Circuit 308

FIRST EXAMPLE OF THE BEATING DECISION

Figure 15:
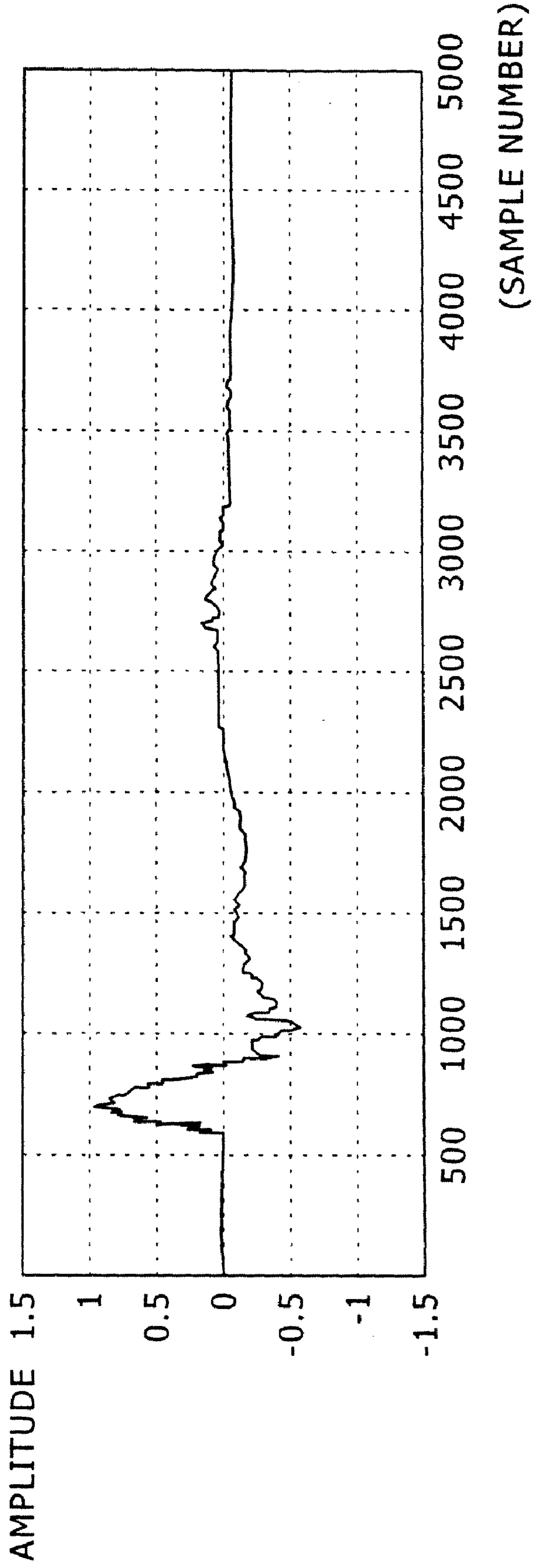
FIG. 15 is a graph illustrating a first example of a beating decision method for the sound outputting apparatus according to the first embodiment of the present invention.

As described hereinabove, sound when the headphone housing 2 is beaten is pulse-like sound. FIG. 15 illustrates an example of sound waveform data (beating waveform data) collected by the microphone 21 when the headphone housing 2 is beaten when the reproduction sound signal S is not inputted. In the example of FIG. 15, the axis of abscissa indicates the time axis sample number where the sampling frequency Fs when the collected sound signal is converted into a digital signal is 48 kHz.

In this first example, such representative beating waveform data as illustrated in FIG. 15 which are obtained from the microphone 21 when the headphone housing 2 is beaten are stored, for example, into a waveform data area of the memory 24. Then, the stored beating waveform data are used to perform coincidence evaluation with the sound signal waveform from the subtraction circuit 307 to detect whether or not the headphone housing 2 is beaten by the user and detect the number of times of beating.

The beating decision circuit 308 sets a fetching interval PD for waveform data for a predetermined period and fetches waveform data of the collected sound signal of the microphone 21, from which the component of the reproduction sound signal S is removed by the subtraction circuit 307, successively by an amount corresponding to the fetching interval PD. To this end, the beating decision circuit 308 includes a buffer memory for fetching waveform data and writes the fetched waveform data into the buffer memory.

Then, a correlation function between the fetched waveform data and the beating waveform data stored in the memory 24 is arithmetically operated and it is decided by coincidence evaluation of them whether or not beating of the headphone housing 2 is performed. It is to be noted that, even if the beating decision process in this instance is delayed a little, there is no problem in practical use.

Here, the length of the fetching interval PD is set to an interval length which includes two successive beating timings when the user beats the headphone housing 2 successively two times in order to issue an alteration instruction of the equalizer characteristic, and is set, for example, 0.5 to 1 second. If three or more successive beating operations are detected or decided within the fetching interval PD, then they are not decided as an alteration instruction.

Figure 21:
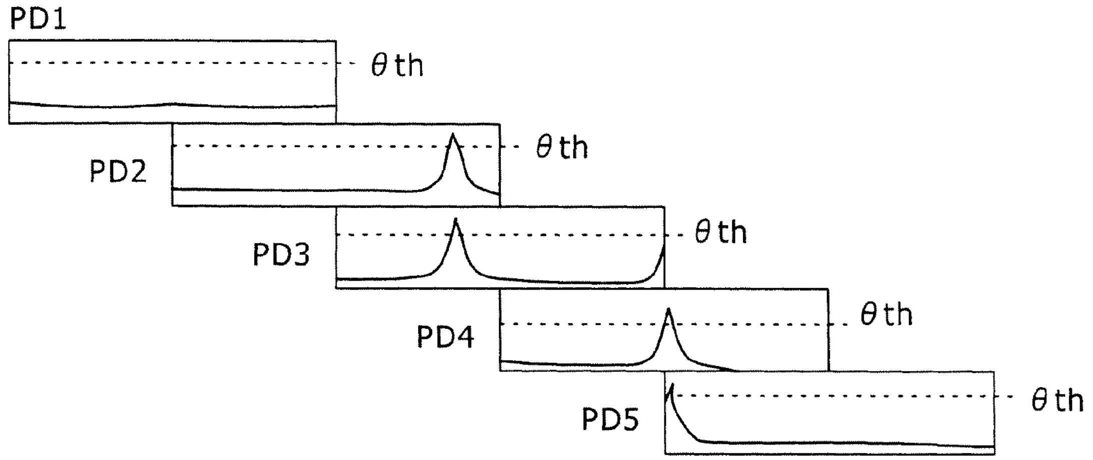
Figure 22:
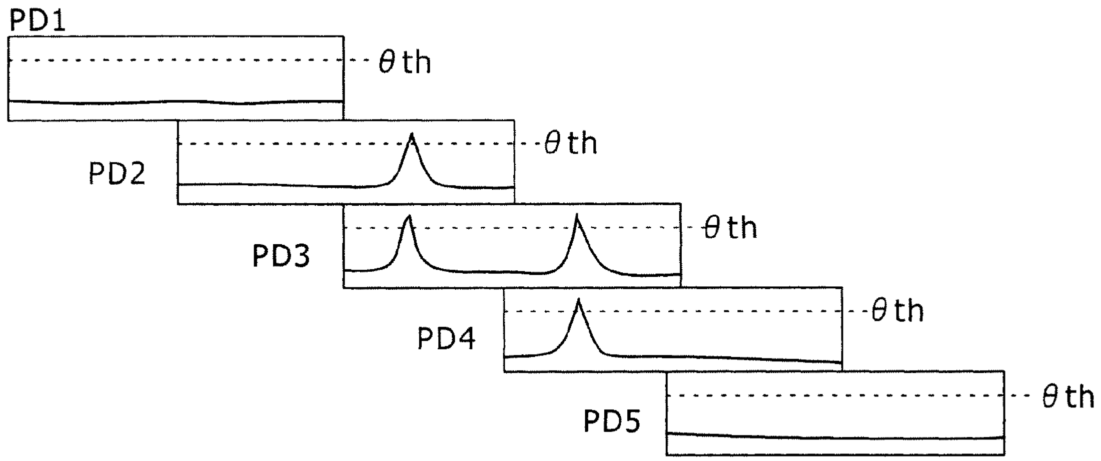

However, even if the user beats the headphone housing 2 successively twice within a period of time of the fetching interval PD described above, depending upon the position of the points of time of beating within the fetching interval PD, only one beating operation may possibly be detected within one fetching interval PD as seen from FIG. 21 or 22.

Figure 23:
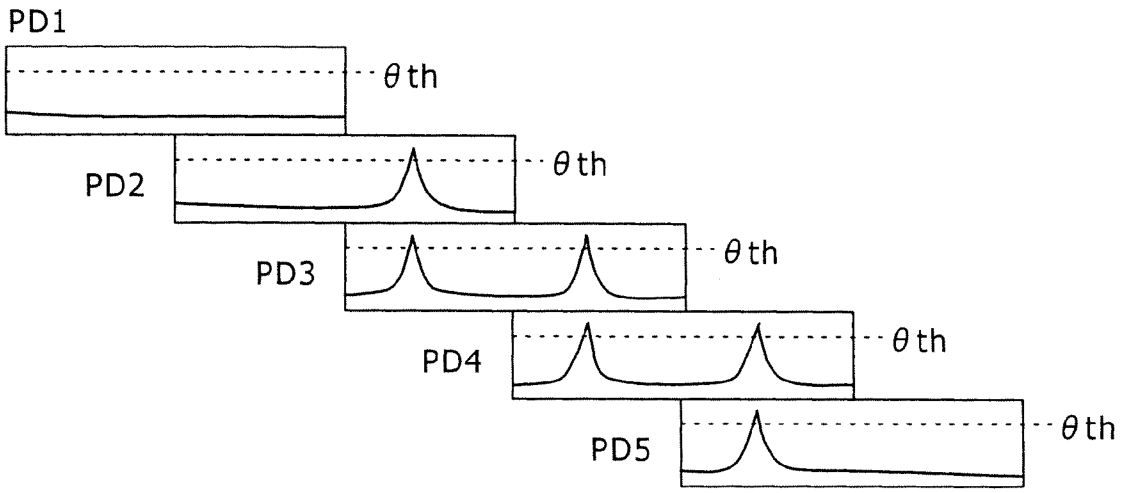

On the other hand, even if the headphone housing 2 is beaten twice within one fetching interval PD, three or more beating operations may actually be performed for the headphone housing 2, for example, as seen in FIG. 23.

Taking the cases described above into consideration, in the present first example, the fetching interval PD is set such that each two successive preceding and succeeding fetching intervals PD have an overlapping interval as seen from fetching intervals PD1, PD2, PD3, . . . in FIGS. 19 to 23. In the examples of FIGS. 19 to 23, the overlapping interval is set to a period of time of just one half the fetching interval PD. It is to be noted that naturally the length of the overlapping interval is not limited to this.

Further, in the present first example, decision of one beating operation or two beating operations is not performed only through decision within one fetching interval PD but performed referring to results of decision with regard to two successive preceding and succeeding fetching intervals PD.

Figure 16:
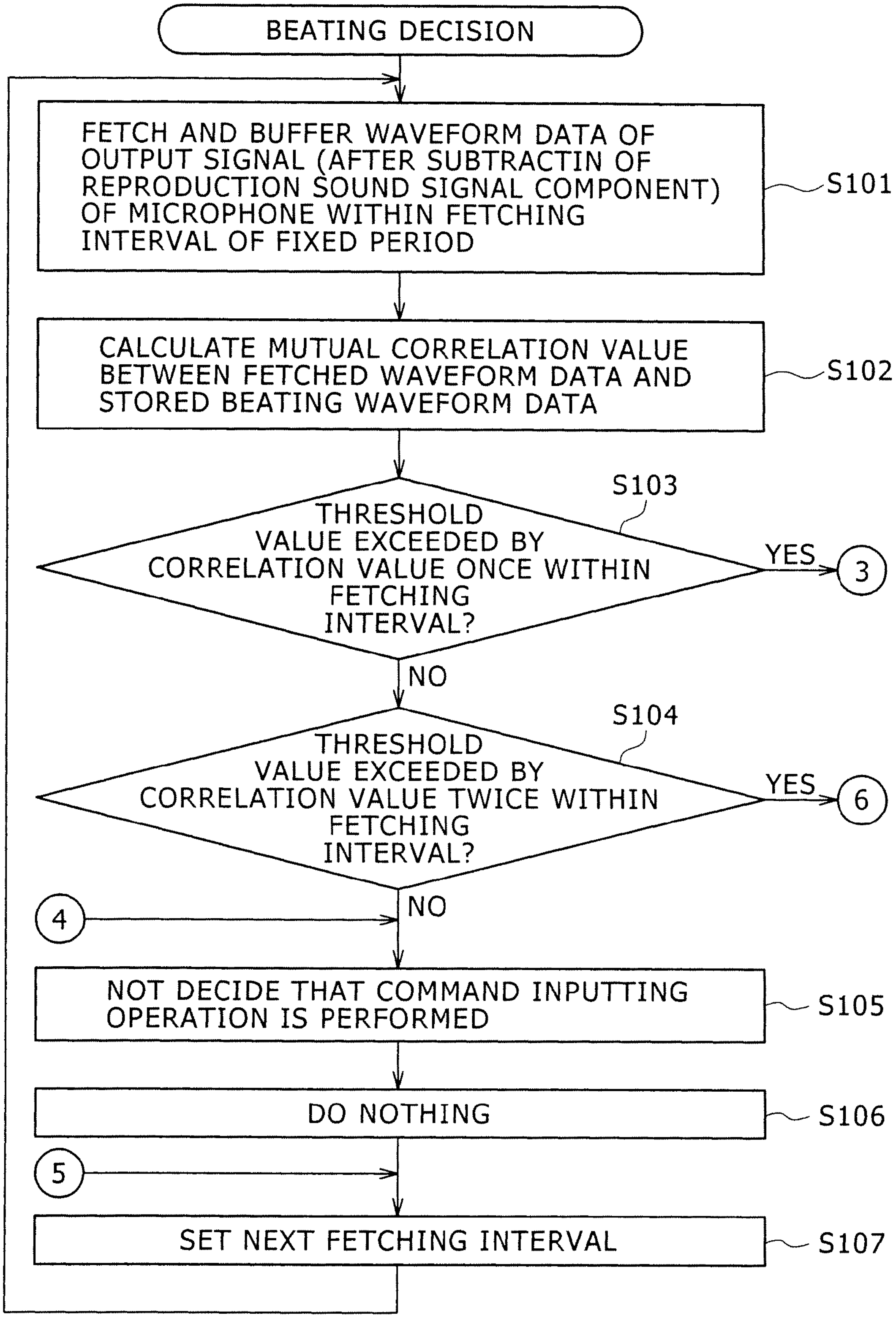
FIGS. 16 to 18 are flow charts illustrating the first example of the beating decision method for the sound outputting apparatus according to the first embodiment of the present invention.
Figure 17:
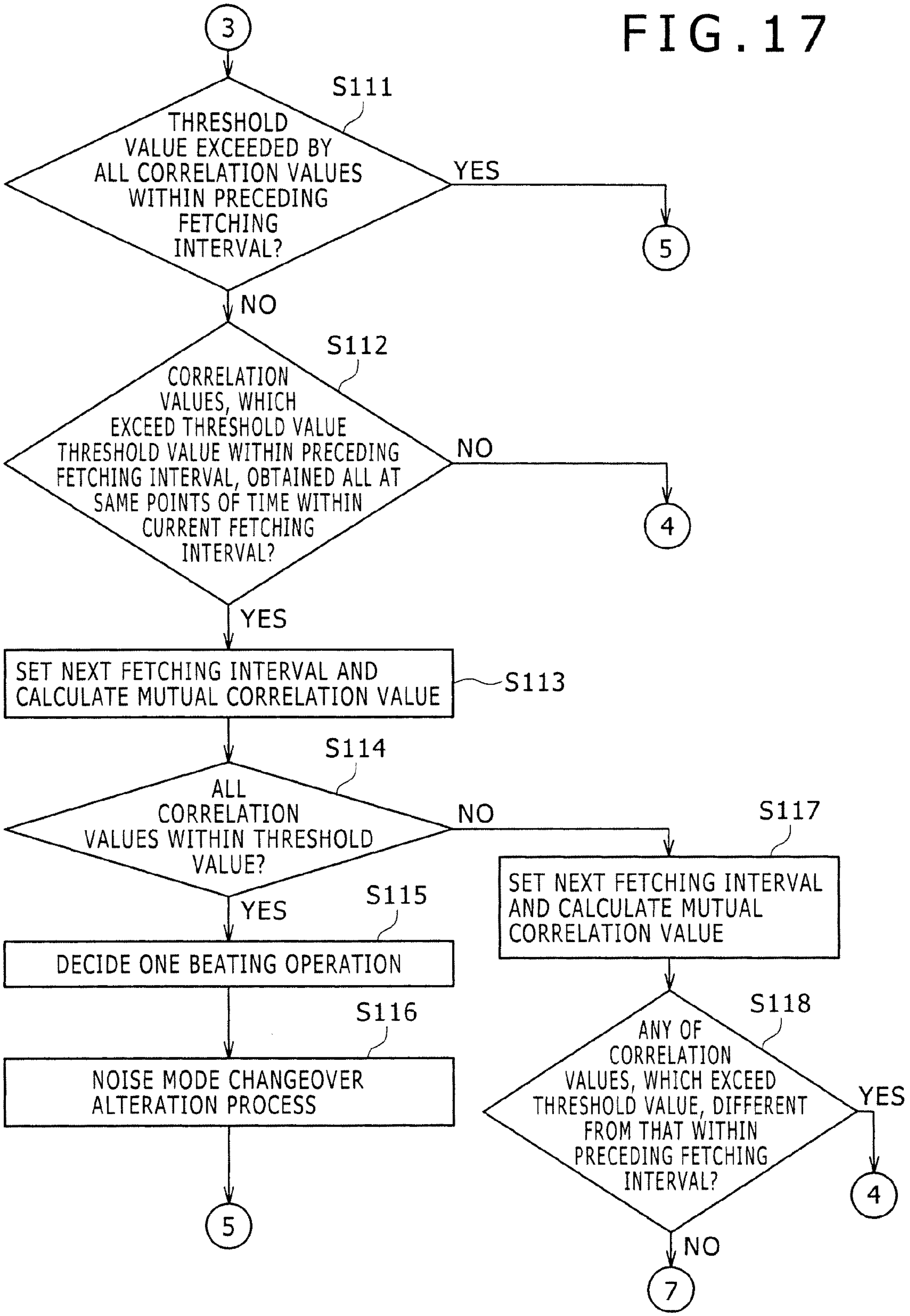
Figure 18:
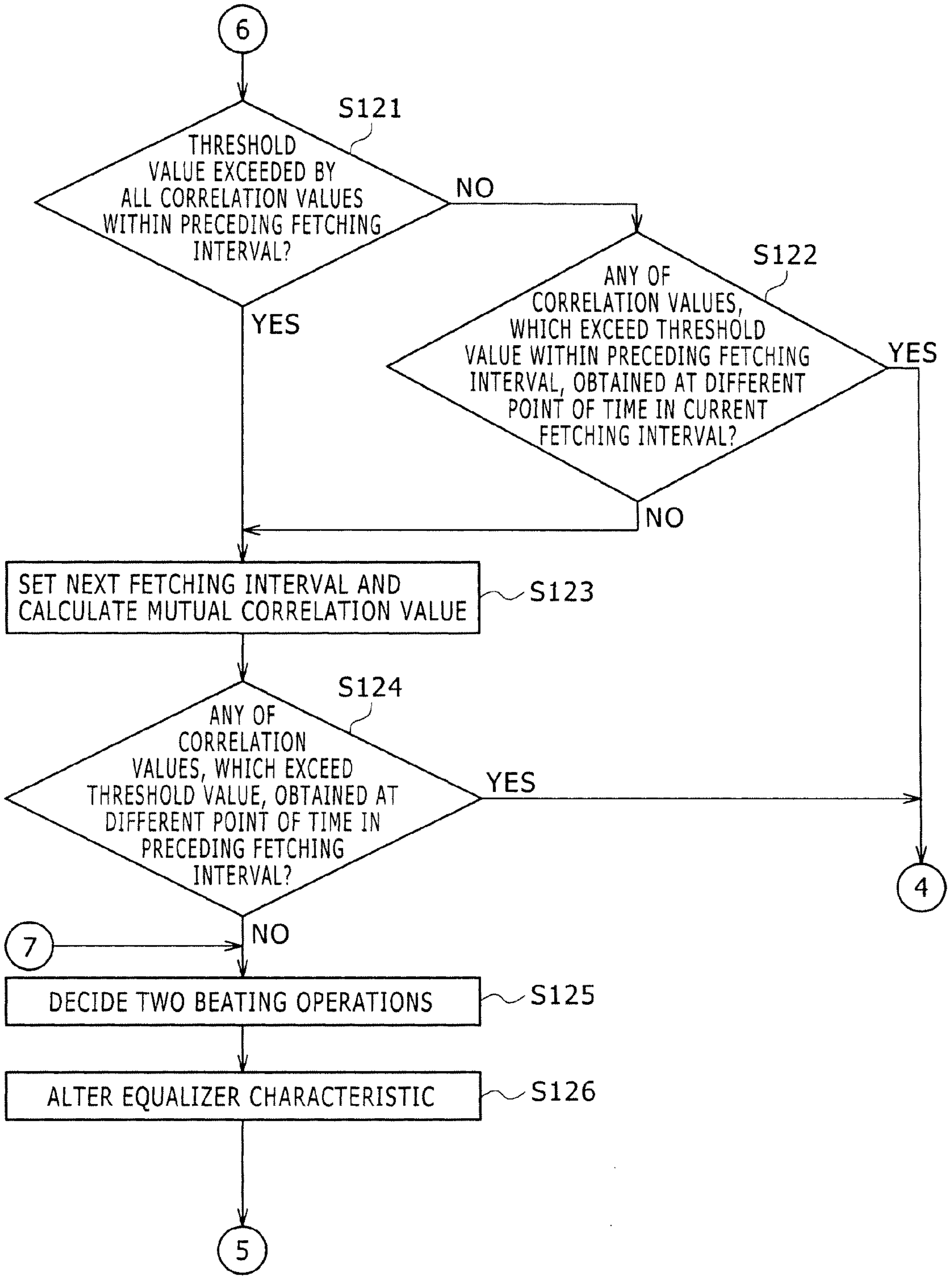

The beating decision method of the present first example is described with reference to FIGS. 16 to 23. It is to be noted that the flow charts of FIGS. 16 to 18 illustrate processing steps executed by the beating decision circuit 308 and the control circuit 304.

The beating decision circuit 308 first fetches, within a set fetching interval PD, waveform data of the collected sound signal of the microphone 21 from which the component of the reproduction sound signal S is removed by the subtraction circuit 307 and temporarily retains the fetched waveform data into the buffer memory (step S101).

Then, after the beating decision circuit 308 completes the fetching of waveform data from the subtraction circuit 307 for a fetching interval PD into the buffer memory, it calculates a mutual correlation value COR of the fetched waveform data and beating waveform data acquired from the control circuit 304 and stored in the memory 24 (step S102).

In this instance, the calculation of the mutual correlation value COR can be performed, for example, by multiplying a sample number of waveform data fetched into the buffer memory, which is equal to the sample number of the beating waveform data read out from the memory 24, by the beating waveform data read out from the memory 24 while successively shifting the position of the sample number of waveform data. Further, the multiplication may not be performed directly using time series waveform data, but fast Fourier transform of the waveform data may be performed such that the multiplication is performed in the frequency region.

Then, the beating decision circuit 308 compares the mutual correlation value COR calculated in the fetching interval PD with a threshold value θth determined in advance to search for the presence of a correlation value exceeding the threshold value θth and decides whether or not the number of times by which the mutual correlation value COR exceeds the threshold value θth is once (step S103). Here, the threshold value θth is set to a value equal to or a little higher than a value with which the beating waveform data and the fetched waveform data have a correlation.

If it is decided at step S103 that the number of times by which the mutual correlation value COR exceeds the threshold value θth is not once (is 0 time or two or more times) within the fetching interval PD, then the beating decision circuit 308 decides whether or not the number of times by which the mutual correlation value COR exceeds the threshold value θth within the fetching interval PD is twice (step S104).

If it is decided that the number of times by which the mutual correlation value COR exceeds the threshold value θth within the fetching interval PD is not twice but 0 time or three or more times, then the beating decision circuit 308 decides that a command inputting operation such as a changeover operation instruction of the noise mode or an alteration operation instruction of the equalizer characteristic by beating is not performed. Then, the beating decision circuit 308 conveys nothing to the control circuit 304 (step S105). Therefore, the control circuit 304 does not perform changeover alternation of the noise mode or alteration of the equalizer characteristic (step S106).

Then, the beating decision circuit 308 sets a next fetching interval PD (step S107). Thereafter, the processing returns to step S101 so that the processes at steps beginning with step S101 are repeated.

On the other hand, if the beating decision circuit 308 decides at step S103 that the number of times by which the mutual correlation value COR exceeds the threshold value θth is once, then the beating decision circuit 308 decides whether or not the mutual correlation value COR does not exceed the threshold value θth at all within the preceding fetching interval PD (step S111 of FIG. 17).

Referring now to FIG. 17, if it is decided that the mutual correlation value COR does not exceed threshold value θth at all within the preceding fetching interval PD, then since the user starts beating in a state wherein a beating operation of the headphone housing 2 is not being performed, it is necessary to supervise also the state of the next fetching interval PD. Therefore, the beating decision circuit 308 advances its processing to step S107 of FIG. 16, at which it sets a next fetching interval PD. Thereafter, the processing returns to step S101 to repeat the processes at the steps beginning with step S101.

On the other hand, if it is decided at step S111 that the correlation value COR exceeds the threshold value θth within the preceding fetching interval PD, then the beating decision circuit 308 decides whether or not those correlation values COR which exceed the threshold value θth within the preceding fetching interval PD include a correlation value COR at a point of time which is different from any of points of time from among the correlation values COR which exceed the threshold value θth in the present cycle (step S112).

If it is decided at step S112 that those correlation values COR which exceed the threshold value θth within the preceding fetching interval PD include a correlation value COR at a point of time which is different from any of points of time from among the correlation values COR which exceed the threshold value θth in the present cycle, then this signifies that the number of correlation values COR which exceed the threshold value θth within the preceding fetching period is three or more. In particular, as seen from FIG. 16, from among states wherein the mutual correlation value COR of the calculation result exceeds the threshold value θth by more than one time from a state wherein a mutual correlation value COR which exceeds the threshold value θth is not included, a state wherein the threshold value θth is exceeded once is decided at step S103, and then another state wherein the threshold value θth is exceeded twice is decided at step S104. Then, if a state wherein the threshold value θth is exceeded once is decided, then the processing advances to the processing routine of FIG. 17, but if the threshold value θth is exceeded twice, then the processing advances to the processing routine of FIG. 18. Then, at step S111, when the state within the preceding fetching interval is absence of any mutual correlation value COR which exceeds the threshold value θth, a next fetching period is checked.

Then, the state which can exist as an interval preceding to the current fetching interval at step S112 is only a state wherein the mutual correlation value COR exceeds the threshold value θth once and another state wherein the mutual correlation value COR exceeds the threshold value θth three or more times.

Accordingly, that those correlation values COR which exceed the threshold value θth within the preceding fetching interval PD include a correlation value COR at a point of time which is different from any of points of time from among the correlation values COR which exceed the threshold value θth in the present cycle indicates that the correlation value COR exceeds the threshold value θth three or more times.

Therefore, if it is decided at step S112 that those correlation values COR which exceed the threshold value θth within the preceding fetching interval PD include a correlation value COR at a point of time which is different from any of points of time from among the correlation values COR which exceed the threshold value θth in the present cycle, then the beating decision circuit 308 advances the processing to step S105 of FIG. 16. At step S105, the beating decision circuit 308 decides that a command inputting operation such as a changeover operation instruction of the noise mode or an alteration operation instruction of the equalizer characteristic by beating is not performed. Then, the beating decision circuit 308 conveys nothing to the control circuit 304. Therefore, the control circuit 304 does not perform changeover alteration of the noise mode, alteration of the equalizer process or the like (step S106).

Then, the beating decision circuit 308 sets a next fetching interval PD (step S107) and thereafter returns the processing to step S101 to repeat the processes at the steps beginning with step S101.

Figure 19:
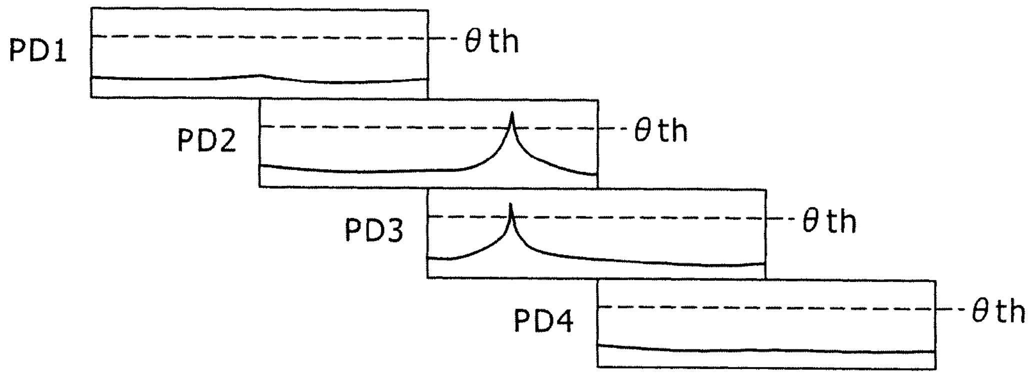
FIGS. 19 to 26 are views illustrating the first example of the beating decision method for the sound outputting apparatus according to the first embodiment of the present invention.
Figure 20:
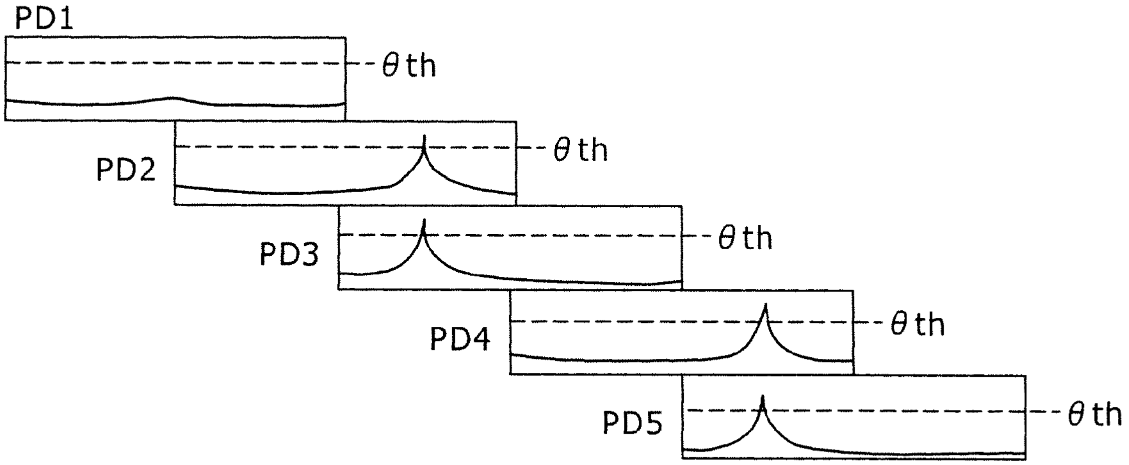

Incidentally, the state wherein it is decided at step S112 that those correlation values COR which exceed the threshold value θth within the preceding fetching interval PD do not include a correlation value COR at a point of time which is different from any of points of time from among the correlation values COR which exceed the threshold value θth in the present cycle, that is, the state wherein the correlation value COR which exceeds the threshold value θth is at a coincident point of time between the preceding and current fetching intervals, may be any of such states as seen in FIGS. 19, 20 and 21. Further, it is necessary to grasp the state of the fetched waveform within the next fetching interval PD. In particular, in FIGS. 19, 20 and 21, the current fetching period at step S113 is the period PD3, and the next fetching period PD4 is checked. Then, in the case of FIGS. 20 and 21, it is necessary to check the state of the further next fetching period PD5.

Further, in FIG. 21, the fetching period at present is the period PD2, and it is necessary to check the state of the next fetching period PD3 and the further next fetching period PD4.

Therefore, in the present example, if it is decided at step S112 that those correlation values COR which exceed the threshold value θth within the preceding fetching interval PD do not include a correlation value COR at a point of time which is different from any of points of time from among the correlation values COR which exceed the threshold value θth in the present cycle, then the control circuit 304 sets a next fetching interval PD and calculates a mutual correlation value COR between the fetched waveform data and the stored beating waveform data (step S113). Then, the beating decision circuit 308 decides whether none of the correlation values COR obtained as a result of the calculation exceeds the threshold value θth, that is, all of the correlation values COR are equal to or lower than the threshold value θth (step S114).

Then, if it is decided at step S114 that none of the correlation values COR obtained as a result of the calculation exceeds the threshold value θth (this is a state wherein none of the correlation values COR exceeds the threshold value θth within the next fetching period PD4 as seen in FIG. 19), then the beating decision circuit 308 decides that the headphone housing 2 is beaten once and sends a notification of this to the control circuit 304 (step S115).

When the control circuit 304 receives the notification of the result of decision of one beating operation, it recognizes the notification as a noise mode changeover operation instruction and executes the noise mode changeover alteration process described hereinabove (step S116).

Then, the beating decision circuit 308 advances the processing to step S107 of FIG. 16, at which it sets a next fetching interval PD. Thereafter, the processing returns to step S101 so that the processes at the steps beginning with step S101 are executed.

On the other hand, if it is decided at step S114 that some of the correlation values COR obtained as a result of the calculation exceeds the threshold value θth (this is a state wherein the next fetching period PD4 includes a correlation value COR which exceeds the threshold value θth as seen in FIGS. 20 and 21), then the beating decision circuit 308 sets a next fetching period PD5 and calculates a mutual correlation value COR between the fetched waveform data and the stored waveform data (step S117).

Then, the beating decision circuit 308 decides whether or not a further next fetching interval PD includes a mutual correlation value COR or correlation values COR obtained as a result of the calculation which exceed the threshold value θth and besides those points of time at which the threshold value θth is exceeded include a point of time different from that in the preceding cycle (step S118).

The state wherein it is decided at step S118 that the state wherein those points of time at which the threshold value θth is exceeded include a point of time different from that in the preceding cycle is the state of FIGS. 20 and 21, and at this time, the beating decision circuit 308 decides that the headphone housing 2 is beaten successively twice (step S125 of FIG. 18). Further, the beating decision circuit 308 conveys this to the control circuit 304.

Consequently, the control circuit 304 recognizes that the two beating operations of the headphone housing 2 represent an alteration instruction of the equalizer characteristic. Thus, the control circuit 304 reads out parameters of the equalizer characteristic to be set to the digital equalizer circuit 305 subsequently from the memory 24 and supplies the parameters to the digital equalizer circuit 305 to alter the equalizer characteristic (step S126).

Then, the beating decision circuit 308 advances the processing to step S107 of FIG. 16, at which it sets a next fetching interval. Thereafter, the processing is returned to step S101 to repeat the processes at the steps beginning with step S101.

On the other hand, the state wherein it is decided at step S118 that those points of time at which the threshold value θth is exceeded include a point of time different from that in the preceding cycle indicates, though not shown in the drawings, presence of more than two correlation values COR which exceed the threshold value θth within the fetching interval PD in FIGS. 20 and 21. Therefore, the beating decision circuit 308 decides that this state indicates more than two successive beating operations and thus decides that a command inputting operation such as a noise mode changeover operation instruction or an equalizer alteration operation instruction is not performed, and conveys nothing to the control circuit 304 (step S105 of FIG. 16). Therefore, the control circuit 304 does not perform changeover operation of the noise mode, alteration of the equalizer characteristic or the like (step S106).

Then, the beating decision circuit 308 sets a next fetching interval PD (step S107) and then returns the processing to step S101 to repeat the processes at the steps beginning with step S101.

On the other hand, if the beating decision circuit 308 decides at step S104 that the number of times by which the mutual correlation value COR exceeds the threshold value θth within the fetching interval PD is twice, then the beating decision circuit 308 decides whether or not the correlation value COR exceeds the threshold value θth by more than one time within the preceding fetching interval PD (step S121 of FIG. 18).

If it is decided at step S121 that the correlation value COR exceeds the threshold value θth by more than one time within the preceding fetching interval PD, then the beating decision circuit 308 decides whether or not those correlation values COR which exceed the threshold value θth in the preceding fetching period PD include a correlation value COR which is different from the mutual correlation value COR which exceeds the threshold value θth in the present cycle (step S122).

Figure 24:
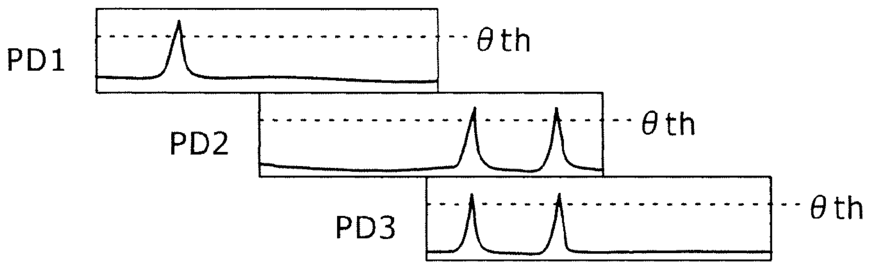

The state wherein it is decided at step S122 that those correlation values COR which exceed the threshold value θth in the preceding fetching period PD include a correlation value COR which is different from the mutual correlation value COR which exceeds the threshold value θth in the present cycle is, for example, such a state as seen in FIG. 24 and indicates a case wherein the headphone housing 2 is beaten successively by three times or more or a like case.

Therefore, if it is decided at step S122 that those correlation values COR which exceed the threshold value θth in the preceding fetching period PD include a correlation value COR which is different from the mutual correlation value COR which exceeds the threshold value θth in the present cycle, then the processing advances to step S105 of FIG. 16, at which the beating decision circuit 308 decides that a command inputting operation such as a noise mode changeover operation instruction or an equalizer alteration operation instruction is not performed and conveys nothing to the control circuit 304. Then, the processes at the processes beginning with step S105 are repeated.

The state wherein it is decided at step S122 that those correlation values COR which exceed the threshold value θth in the preceding fetching period PD do not include a correlation value COR which is different from the mutual correlation value COR which exceeds the threshold value θth in the present cycle is, for example, such a state as illustrated in FIGS. 22 and 23, and it is necessary to grasp the state of the fetched waveform within a further next fetching interval PD. In particular, in FIGS. 22 and 23, the current fetching interval at step S122 is the period PD3, and it is necessary to check the state of the next fetching period PD4.

Therefore, if it is decided at step S122 that those correlation values COR which exceed the threshold value θth in the preceding fetching period PD do not include a correlation value COR which is different from the mutual correlation value COR which exceeds the threshold value θth in the present cycle, then the control circuit 304 sets a next fetching period PD (n FIGS. 22 and 23, the fetching period PD4) and calculates the mutual correlation value COR between the fetched waveform data and the stored beating waveform data (step S123).

Then, the beating decision circuit 308 decides whether or not those points of time at which the threshold value θth is exceeded by the correlation values COR obtained as a result of the calculation include any point of time which is different from that in the preceding cycle (in FIGS. 22 and 23, within the period PD3) (step S124).

In this instance, the state wherein the points of time at which the threshold value θth is exceeded in the preceding cycle (in FIGS. 22 and 23, the period PD3) and the present cycle (in FIGS. 22 and 23, the fetching period PD4) have no different point of time therebetween is, for example, a state of FIG. 22. On the other hand, the state wherein the points of time at which the threshold value θth is exceeded in the preceding cycle (in FIGS. 22 and 23, the period PD3) and the present cycle (in FIGS. 22 and 23, the fetching period PD4) have some different points of time therebetween is, for example, a state of FIG. 23.

Therefore, if it is decided at step S124 that the points of time at which the threshold value θth is exceeded in the preceding cycle (in FIGS. 22 and 23, the period PD3) and the present cycle (in FIGS. 22 and 23, the fetching period PD4) have no different point of time therebetween, then the beating decision circuit 308 decides that the headphone housing 2 is beaten successively twice (step S125 of FIG. 18) and conveys this to the control circuit 304.

Consequently, the control circuit 304 recognizes that the two beating operations of the headphone housing 2 are an alteration instruction of the equalizer characteristic. As a result, the control circuit 304 reads out parameters of the equalizer characteristics to be set to the digital equalizer circuit 305 subsequently from the memory 24 and supplies the parameters to the digital equalizer circuit 305 to alter the equalizer characteristic (step S126).

Then, the beating decision circuit 308 advances the processing to step S107 of FIG. 16, at which it sets a next fetching interval. Thereafter, the beating decision circuit 308 returns the processing step S101 to repeat the processes at the steps beginning with step S101.

On the other hand, if it is decided at step S124 that the points of time at which the threshold value θth is exceeded in the preceding cycle (in FIGS. 22 and 23, the period PD3) and the present cycle (in FIGS. 22 and 23, the fetching period PD4) have some different points of time therebetween, then the beating decision circuit 308 decides that three or more successive beating operations are performed and hence decides that a command inputting operation such as a noise mode changeover operation instruction or an equalizer alteration operation instruction is not performed. Consequently, the beating decision circuit 308 conveys nothing to the control circuit 304 (step S105 of FIG. 16). Therefore, the control circuit 304 does not perform a noise mode changeover operation instruction or an equalizer alteration operation instruction (step S106).

Then, the beating decision circuit 308 sets a next fetching interval PD (step S107) and returns the processing to step S101 to repeat the processes at the steps beginning with step S101.

Figure 25:
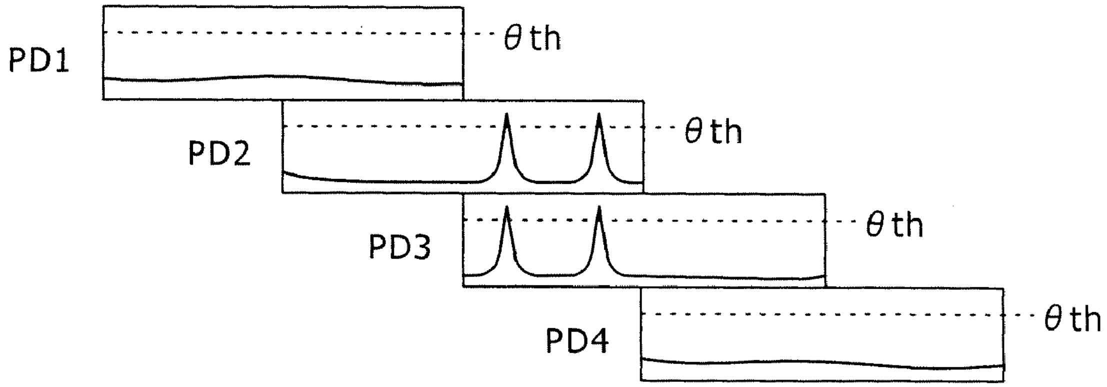
Figure 26:
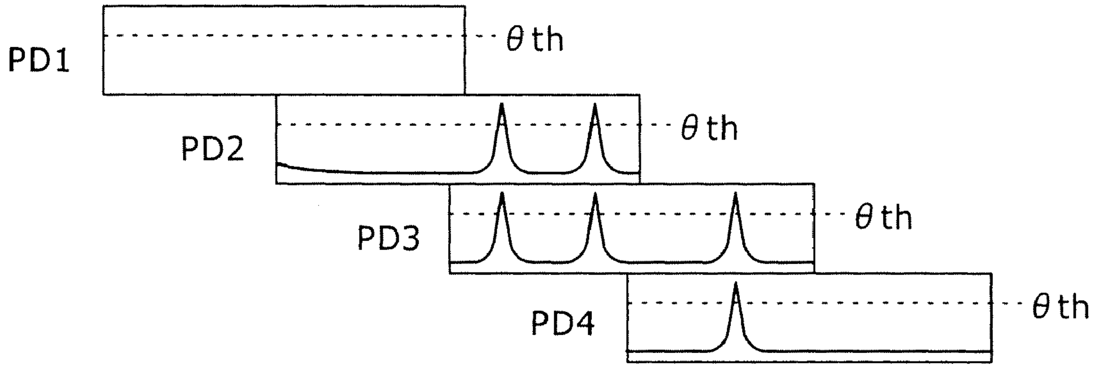

The state wherein it is decided at step S121 that the correlation value COR does not exceed the threshold value θth at all within the preceding fetching interval PD is, for example, such a state as seen in FIGS. 25 and 26. Accordingly, also in this instance, it is necessary to grasp the state of the fetched waveform within a next fetching interval PD. In other words, in FIGS. 25 and 26, the fetching interval at present at step S121 is the fetching period PD2, and it is necessary to check the state within the next period PD3.

Therefore, when it is decided at step S121 that the correlation value COR does not exceed the threshold value θth at all within the preceding fetching interval PD, the beating decision circuit 308 sets a next fetching interval PD (in FIGS. 25 and 26, the period PD3) and calculates a mutual correlation value COR between the fetched waveform data and the stored beating waveform data (step S123).

Then, the beating decision circuit 308 decides whether or not those points of time at which the threshold value θth is exceeded by the correlation values COR obtained as a result of the calculation include any point of time which is different from that in the preceding cycle (in FIGS. 25 and 26, the fetching period PD3) (step S124).

In this instance, the state wherein those points of time at which the threshold value θth is exceeded by the correlation values COR in the present cycle (in FIGS. 25 and 26, the fetching period PD3) do not include any point of time which is different from that in the preceding cycle (in FIGS. 25 and 26, the fetching period PD2) is, for example, a state of FIG. 25. On the other hand, the state wherein those points of time at which the threshold value θth is exceeded by the correlation values COR in the present cycle (in FIGS. 25 and 26, the fetching period PD3) include some point of time which is different from that in the preceding cycle (in FIGS. 25 and 26, the fetching period PD2) is, for example, a state of FIG. 26.

Therefore, if it is decided at step S124 that those points of time at which the threshold value θth is exceeded by the correlation values COR in the present cycle (in FIGS. 25 and 26, the fetching period PD3) do not include any point of time which is different from that in the preceding cycle (in FIGS. 25 and 26, the fetching period PD2), then the beating decision circuit 308 decides that the headphone housing 2 is successively beaten twice (step S125 of FIG. 18) and conveys this to the control circuit 304.

Consequently, the control circuit 304 recognizes that the headphone housing 2 is beaten twice as an alteration instruction of the equalizer characteristic. Thus, the control circuit 304 reads out parameters of the equalizer characteristic to be set to the digital equalizer circuit 305 subsequently from the memory 24 and supplies the parameters to the digital equalizer circuit 305 to alter the equalizer characteristic (step S126).

Then, the beating decision circuit 308 jumps the processing to step S107 of FIG. 16, at which it sets a next fetching interval. Thereafter, the processing returns to step S101 to repeat the processes at the steps beginning with step S101.

On the other hand, if it is decided at step S124 that those points of time at which the threshold value θth is exceeded by the correlation values COR in the present cycle (in FIGS. 25 and 26, the fetching period PD3) include any point of time which is different from that in the preceding cycle (in FIGS. 25 and 26, the fetching period PD2), then the beating decision circuit 308 decides that the headphone housing 2 is beaten three or more times successively. Thus, the beating decision circuit 308 decides that a noise mode changeover operation instruction of an equalizer alteration operation instruction is not received and conveys nothing to the control circuit 304 (step S105 of FIG. 16). Therefore, the control circuit 304 does not changeover alteration of the noise mode or alteration of the equalizer characteristic (step S106).

The, the beating decision circuit 308 sets a next fetching interval PD (step S107) and then returns the processing to step S101 to repeat the processes at the steps beginning with step S101.

In this manner, in the first example, one beating operation and two beating operations of the headphone housing 2 can be decided based on a mutual correlation value between waveform data fetched from a signal obtained by removing a reproduction sound signal S from a collected sound signal of the microphone 21 and beating waveform data stored in the memory 24. Then, a noise mode changeover operation instruction and an equalizer characteristic alteration operation instruction can be decided from the one beating operation and the two beating operations of the headphone housing 2, respectively.

MODIFICATIONS OF THE FIRST EXAMPLE

In the foregoing description, the memory 24 retains representative waveform data of beating waveform data. However, where several kinds of beating waveform data have different waveform tendencies depending upon the manner of beating or the beating position of the headphone housing 2, the different beating waveform data may be stored in advance into the memory 24 such that the mutual correlation process described hereinabove is performed for all beating waveform data to decide one beating operation and two beating operations of the headphone housing 2.

Further, while, in the foregoing description of the embodiment, beating waveform data are stored in advance in the memory 24, also it is possible to provide the DSP 232 with a learning function for storing, into the memory 24, beating waveform data obtained from a beating sound signal of the microphone 21 when the user actually beats the headphone housing 2.

In this instance, for example, a particular operation section for activating the learning function is provided in the control circuit 304 of the DSP 232, and if the operation section is operated, then the control circuit 304 notifies the user of completion of registration preparations of beating waveform data through electronic sound or a sound message. Then, the control circuit 304 recognizes later beating of the headphone housing 2 by the user as a fetching instruction for beating waveform data to be registered, and fetches beating waveform data obtained from a collected sound signal of the microphone 21 and stores the beating waveform data into the memory 24.

In this instance, if beating waveform data are already written in the memory 24, then they may be replaced by the new beating waveform data, or the new beating waveform data and the beating waveform data written already in the memory 24 may be averaged such that the averaged beating waveform data are rewritten into the memory 24.

Further, in the embodiment described hereinabove, one beating operation and two beating operations are detected as beating of the headphone housing 2. However, three beating operations, four beating operations and so forth may be detected additionally so that operation instructions for further various processes may be provided.

For example, in place of provision of a particular operation section for starting a learning function in the control circuit 304 of the DSP 232, beating of the headphone housing 2, for example, three successive beating operations of the headphone housing 2, may be used as an instruction operation for starting the learning function.

SECOND EXAMPLE OF BEATING DECISION

The beating decision method of the present second example is a simplified beating decision method which does not involve such storage in advance of beating waveform data in the memory 24 as in the first example, but utilizes the shape of the beating waveform illustrated in FIG. 15.

In particular, it is known that, as seen from FIG. 15, the beating waveform exhibits attenuation with a comparatively determined damping ratio at samples preceding and succeeding to a sample thereof which indicates a maximum amplitude value.

Therefore, in the present second example, a time length in which one beating waveform (beating response waveform) almost calms down is set as a fetching interval PD for waveform data described hereinabove, and a maximum amplitude value sample is checked within the fetching interval PD. Then, if a maximum value sample is detected successfully, then the amplitude value of samples preceding and succeeding to the maximum value sample is checked. Then, it is decided whether or not a beating waveform is included within the fetching interval PD depending upon whether or not damping ratios of the samples from the maximum value are equal or similar to the determined damping ratio. In other words, beating of the headphone housing 2 by the user is decided.

In the present second example, fetching intervals PD are not overlapped with each other, or even if they are overlapped with each other, the overlap is permitted within a very short period of time. Then, since, in the second example, the time length of the fetching interval PD is set such that one beating waveform (beating response waveform) almost calms down in the fetching interval as described above, one beating operation and two beating operations of the headphone housing 2 by the user are decided using a fetching interval PDa within which one beating operation is detected and a result of beating decision within an immediately succeeding fetching interval PDb, as shown in FIGS. 27A and 27B.

In the present second example, the beating decision circuit 308 includes a beating time number counter and counts the number of times of beating within two successive fetching intervals.

Figures 27A, 27B, 27C:
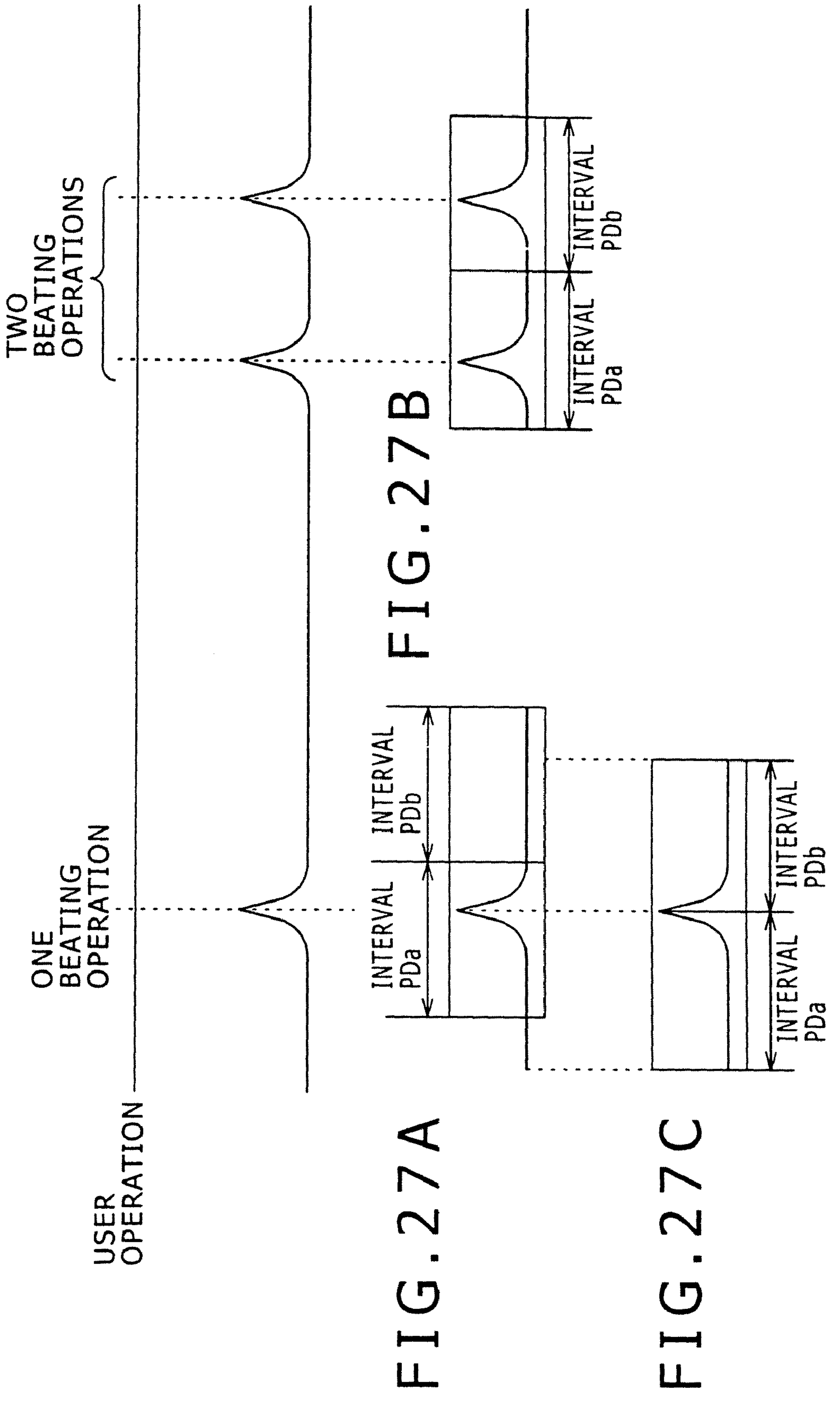
FIGS. 27A to 27C are views illustrating a second example of the beating decision method for the sound outputting apparatus according to the first embodiment of the present invention.

However, if the beating timing of the headphone housing 2 by the user is in the proximity of a boundary of a fetching interval PD (end of the fetching interval PD), then the two fetching intervals PDa and PDb are coupled to each other as seen in FIG. 27C to make a beating decision.

Figure 28:
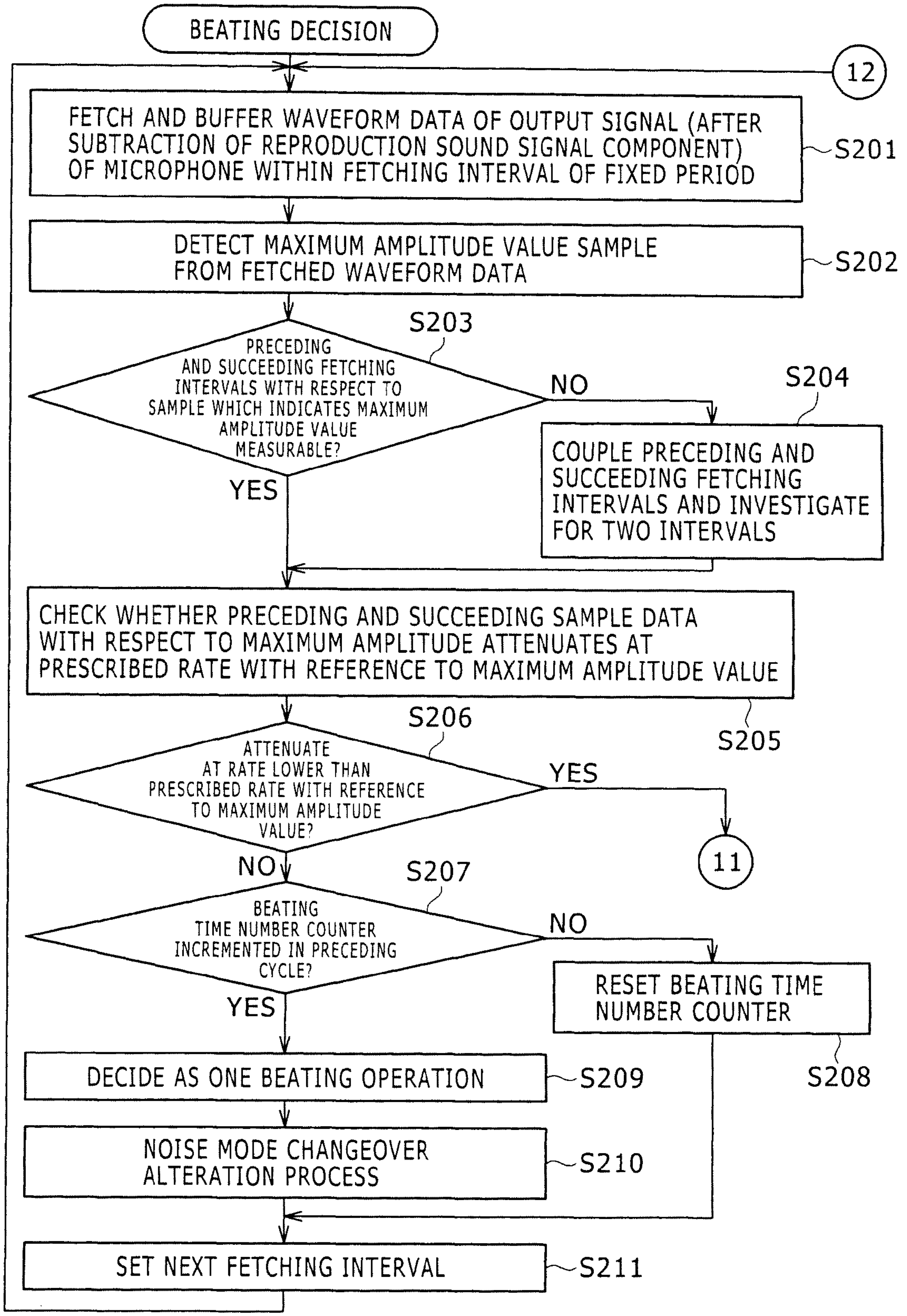
FIGS. 28 and 29 are flow charts illustrating the second example of the beating decision method for the sound outputting apparatus according to the first embodiment of the present invention.
Figure 29:
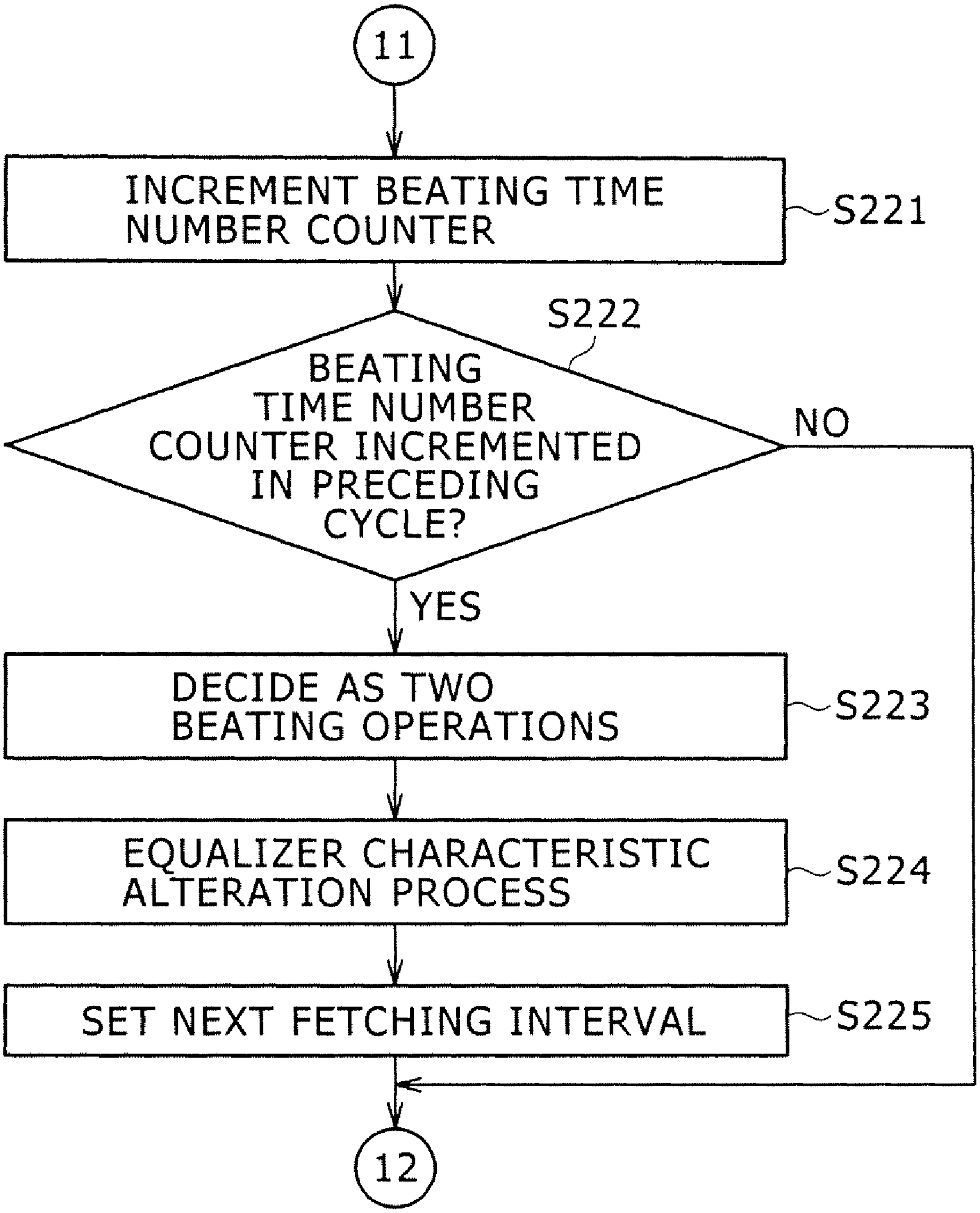

An example of processing where the beating decision method of the second example is used is described below with reference to FIGS. 28 and 29. It is to be noted that the flow charts of FIGS. 28 and 29 illustrate processing steps executed by the beating decision circuit 308 and the control circuit 304.

First, the beating decision circuit 308 fetches, within a set fetching interval PD for waveform data, waveform data of the collected sound signal of the microphone 21, from which a component of a reproduction sound signal S is removed by the subtraction circuit 307, and temporarily retains the fetched waveform data into a buffer memory (step S201).

Then, after the beating decision circuit 308 completes the fetching of waveform data from the subtraction circuit 307 for the fetching interval PD into the buffer memory, the beating decision circuit 308 detects a sample which indicates a maximum amplitude value from among the fetched waveform data (step S202).

If a sample indicative of a maximum amplitude value is detected, then the beating decision circuit 308 detects whether or not the sample indicative of the maximum amplitude value is at an end of the fetching interval PD and preceding and succeeding samples to the sample indicative of the maximum amplitude value can be observed (step S203).

Then, if it is decided that preceding and succeeding samples to the sample indicative of the maximum amplitude value can be observed, then the beating decision circuit 308 advances the processing directly to step S205. On the other hand, if it is decided that preceding and succeeding samples to the sample indicative of the maximum amplitude value may not be able to be observed, then the beating decision circuit 308 couples the two fetching intervals PD within which observation of the preceding and succeeding samples to the sample indicative of the maximum amplitude value is possible to the sample indicative of the maximum amplitude value to produce two observation intervals (step S204). Thereafter, the processing advances to step S205.

At step S205, the beating decision circuit 308 checks whether or not the sample data preceding and succeeding to the sample indicative of the maximum amplitude value exhibit attenuation with a prescribed ratio from the maximum amplitude value. Then, the beating decision circuit 308 decides whether or not the fetched waveform data exhibit attenuation at a rate lower than the prescribed ratio with reference to the maximum amplitude value (step S206).

If it is decided at step S206 that the fetched waveform data exhibit attenuation at a rate lower than the prescribed ratio with reference to the maximum amplitude value, then the beating decision circuit 308 increments the beating time number counter by one (step S221 of FIG. 29).

Referring now to FIG. 29, the beating decision circuit 308 decides whether or not the beating time number counter is incremented within the immediately preceding fetching interval PD from the count value of the beating time number counter (step S222). If it is decided that the beating time number counter is incremented, then the beating decision circuit 308 decides that the headphone housing 2 is beaten twice and notifies the control circuit 304 of this (step S223).

The control circuit 304 receives the notification of the two beating operations and recognizes the notification as an alteration instruction of the equalizer characteristic. Then, the control circuit 304 reads out parameters of the equalizer characteristic to be set to the digital equalizer circuit 305 subsequently from the memory 24 and supplies the parameters to the digital equalizer circuit 305 to alter the equalizer characteristic (step S224).

Then, the beating decision circuit 308 sets a next fetching interval (step S225) and then returns the processing to step S201 to repeat the processes at the steps beginning with step S201.

On the other hand, if it is decided at step S222 that the beating time number counter is not incremented within the immediately preceding fetching interval PD, then the beating decision circuit 308 returns the processing immediately to step S201 to repeat the processes at the steps beginning with step S201.

Referring back to FIG. 28, if it is decided at step S206 that the fetched waveform data do not exhibit attenuation at a rate lower than the prescribed ratio with reference to the maximum amplitude value, then the beating decision circuit 308 decides whether or not the beating time number counter is incremented within the immediately preceding fetching interval PD from the count value of the beating time number counter (step S207).

If it is decided at step S207 that the beating time number counter is not incremented within the immediately preceding fetching interval PD, then the beating decision circuit 308 resets the beating time number counter (step S208) and then sets a next fetching interval (step S211). Then, the beating decision circuit 308 returns the processing to step S201 to repeat the processes at the steps beginning with step S201.

On the other hand, if it is decided at step S207 that the beating time number counter is incremented within the immediately preceding fetching interval PD, then the beating decision circuit 308 decides that the headphone housing 2 is beaten once and notifies the control circuit 304 of this (step S209).

Upon reception of the notification of the decision result of one beating operation, the control circuit 304 recognizes the notification as a noise mode changeover operation instruction and executes the noise mode changeover alteration process described hereinabove (step S210).

Then, the beating decision circuit 308 sets a next fetching interval PD (step S211) and then returns the processing to step S201 to repeat the processes at the steps beginning with step S201.

It is to be noted that the "next fetching interval PD" at step S211 naturally is, where two fetching intervals are coupled at step S204, the latter one of the two fetching intervals coupled to each other.

THIRD EXAMPLE OF BEATING DECISION

The beating decision method according to the third example is advantageous in that the structure of the headphone housing 2 is devised so that the response waveform when the user beats the headphone housing 2 can be distinguished readily from the other signals such as noise and a sound signal.

Figure 30:
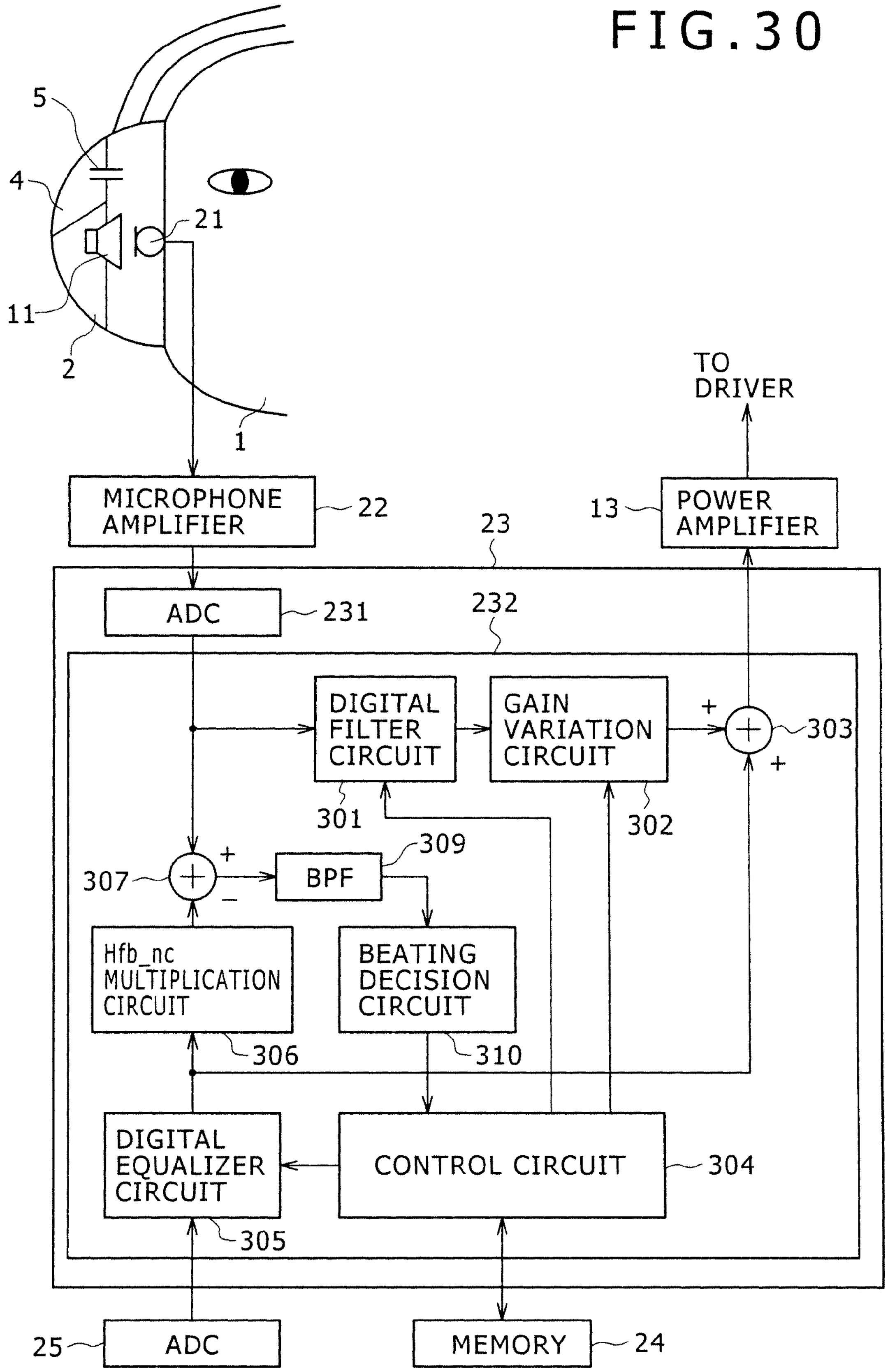
FIG. 30 is a block diagram illustrating a third example of the beating decision method for the sound outputting apparatus according to the first embodiment of the present invention.

In the present third example, for example, as seen in FIG. 30, a small chamber 4 of a volume V and a port 5 communicating with the small chamber 4 are provided as acoustic mechanical components in the headphone housing 2. In this instance, the small chamber 4 and the port 5 are formed such that they form a resonance point when the headphone housing 2 is beaten.

Figure 31:
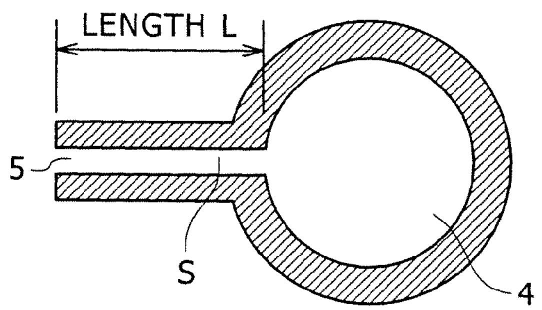
FIG. 31 is a view illustrating the third example of the beating decision method for the sound outputting apparatus according to the first embodiment of the present invention.

FIG. 31 illustrates an equivalent configuration of a portion of the headphone housing 2 including the small chamber 4 and the port 5. Referring to FIG. 31, where the length of the port 5 is represented by L, the sectional area of the port 5 by S and the volume of the small chamber 4 by V, the frequency fo at the resonance point is given by $$f_o c = c/(2\Pi)\bullet(S/(LV))^{1/2} \quad \text{(expression 8)}$$

where c is the velocity of the sound wave. From the expression 8, if the sectional area of the port S and the length L of the port 5 are selected suitably, then the frequency fo can be set to the resonance frequency when the headphone housing 2 is beaten.

Where the acoustic mechanical configuration formed from the small chamber 4 and the port 5 is provided in the headphone housing 2 and the frequency fo of the acoustic mechanical configuration is set so as to be equal to the resonance frequency when the headphone housing 2 is beaten, when the headphone housing 2 is beaten by the user, the response waveform then is influenced much by the resonance point of the acoustic mechanical configuration and has high energy around the frequency fo.

Taking this into consideration, in the present third example, a band-pass filter 309 having a steep pass band characteristic whose pass center frequency is the frequency fo is provided for an output signal of the subtraction circuit 307 as seen in FIG. 30. Then, an output signal of the band-pass filter 309 is supplied to a beating decision circuit 310.

Figure 32A:
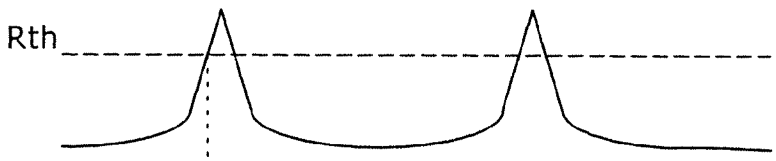
FIGS. 32A and 32B are waveform diagrams illustrating the third example of the beating decision method for the sound outputting apparatus according to the first embodiment of the present invention.

The beating decision circuit 310 decides that the headphone housing 2 is beaten when the signal amplitude from the band-pass filter 309 exceeds a threshold level Rth with which it can be decided that the headphone housing 2 is beaten (refer to FIG. 32A).

Figure 32B:
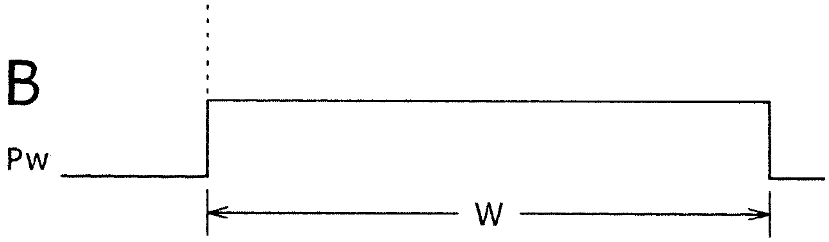

Then, the beating decision circuit 310 decides two beating operations in the following manner. In particular, in the present third example, the beating decision circuit 310 produces such a window pulse Pw of a predetermined window width W as seen in FIG. 32B such that it rises at a point of time of the top of the signal of the band-pass filter 309 at which the signal amplitude from the band-pass filter 309 exceeds the threshold level Rth as seen in FIG. 32A.

Then, the beating decision circuit 310 decides whether or not the signal from the band-pass filter 309 includes a pulse-like component whose signal amplitude exceeds the threshold level Rth within the window width W of the window pulse Pw. Then, if it is decided that the signal from the band-pass filter 309 does not include a pulse-like component whose signal amplitude exceeds the threshold level Rth within the window width W of the window pulse Pw, then the beating decision circuit 310 decides that the headphone housing 2 is beaten once and notifies the control circuit 304 of a result of the decision. On the other hand, if it is decided that the signal from the band-pass filter 309 includes one single pulse-like component whose signal amplitude exceeds the threshold level Rth within the window width W of the window pulse Pw, then the beating decision circuit 310 decides that the headphone housing 2 is beaten two times and notifies the control circuit 304 of the result of the decision.

It is to be noted that, even if the signal from the band-pass filter 309 includes a pulse-like component whose signal amplitude exceeds the threshold level Rth within the window width W of the window pulse Pw, if the number of the components is more than two, then since the number of times of beating is three or more, the beating decision circuit 310 in this example conveys nothing to the control circuit 304.

The control circuit 304 recognizes the notification from the beating decision circuit 310 as a noise mode changeover operation instruction or an equalizer alteration operation instruction and executes the noise mode changeover alteration process or the equalizer characteristic alteration process in a similar manner as described hereinabove.

In this manner, according to the present third example, the beating decision circuit 310 can be formed in a comparatively simple configuration.

MODIFICATIONS OF THE THIRD EXAMPLE

In the third example described above, an acoustic mechanical configuration formed from the small chamber 4 and the port 5 is provided in the headphone housing 2 to produce a resonance point. However, the configuration may otherwise be provided, for example, by the headphone housing 2 itself without providing such an acoustic mechanical configuration as described above.

In this instance, although the acoustic influence of the resonance is little upon reproduction of the sound signal S, when the headphone housing 2 is actually beaten, since the resonance has a significant influence, the beating decision can be made readily.

Further, the output signal of the subtraction circuit 307 is free from the component of the sound signal S, and besides the beating waveform when the headphone housing 2 is beaten has a comparatively great amplitude as described hereinabove with reference to FIG. 15. Therefore, even if such a resonance point as described above is not produced, an amplitude component of the output signal of the subtraction circuit 307 which has an amplitude higher than a predetermined threshold level may be detected as a component by beating of the headphone housing 2.

Second Embodiment

Noise Reduction Apparatus of the Feedforward Type

Figure 33:
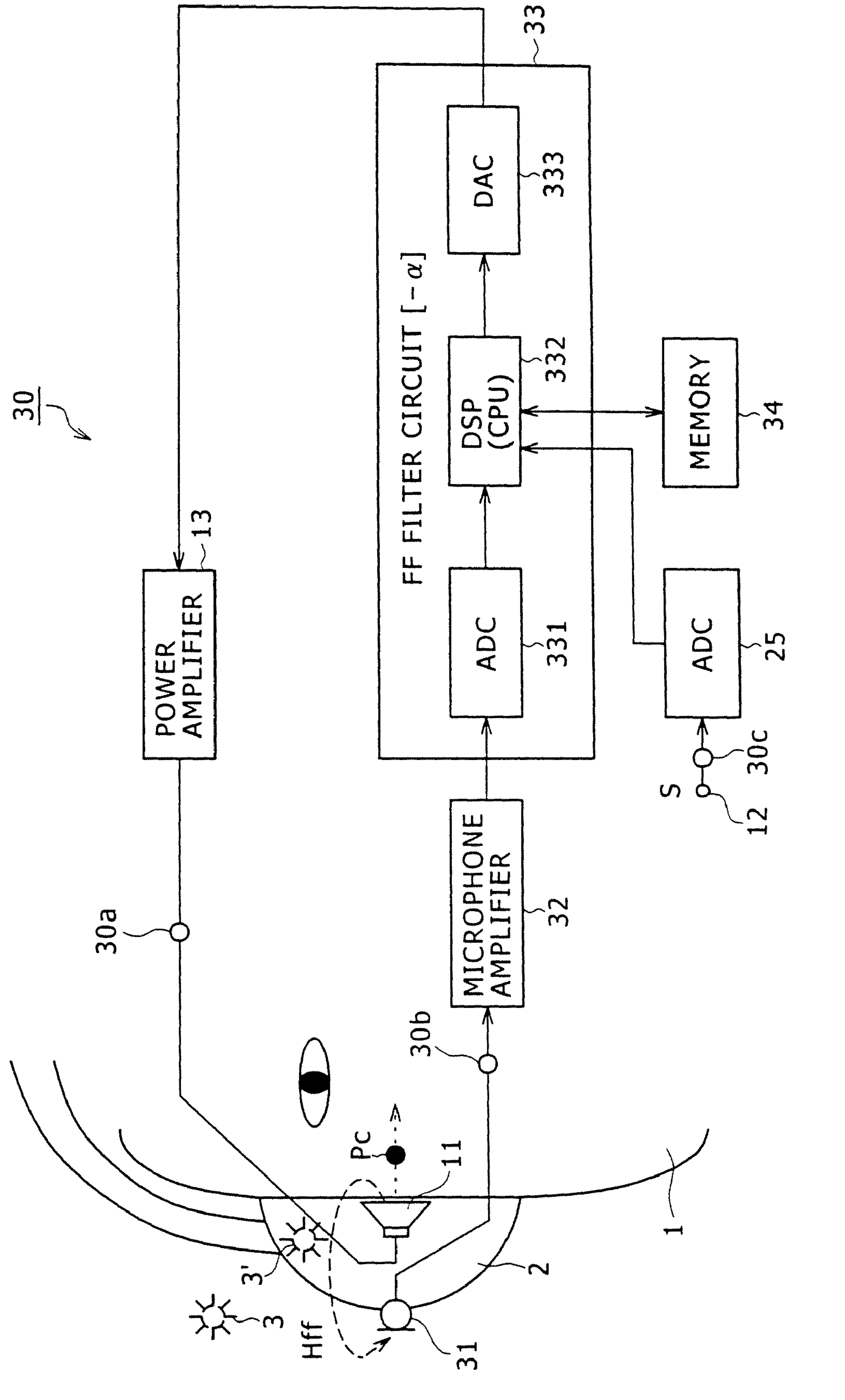
FIG. 33 is a block diagram showing an example of a headphone apparatus to which a sound outputting apparatus according to a second embodiment of the present invention is applied.

FIG. 33 shows a sound outputting apparatus according to a second embodiment of the present invention wherein a noise reduction apparatus of the feedforward type is applied in place of such a noise reduction apparatus of the feedback type in the first embodiment as described hereinabove to the noise reduction apparatus section of a headphone apparatus. In FIG. 33, components similar to those previously described with reference to FIG. 1 are denoted by the same reference numerals.

Referring to FIG. 33, the noise reduction apparatus section 30 in the second embodiment includes a microphone 31 serving as an acousto-electric conversion section, a microphone amplifier 32, a filter circuit 33 for noise reduction, a memory 34, and the like.

The noise reduction apparatus section 30 is connected to a driver 11, the microphone 31 and a headphone plug which forms a sound signal input terminal 12 by a connection cable similarly to the noise reduction apparatus section 20 of the feedback type described hereinabove. The connection cable is connected at connection terminal portions **30*a*, 30*b* and 30*c* to the noise reduction apparatus section 30**.

In the present second embodiment, noise entering from a noise source 3 outside the headphone housing 2 into a music listening position in the headphone housing 2 in a music listening environment of a listener 1 is reduced in accordance with the feedforward system so that the listener 1 can listen to the music in a good environment.

In the noise reduction system of the feedforward type, basically the microphone 31 is disposed outside the headphone housing 2 as seen in FIG. 33. The noise 3 collected by the microphone 31 is subjected to a suitable filtering process to produce a noise reduction sound signal. The thus produced noise reduction sound signal is acoustically reproduced by the driver 11 in the headphone housing 2 so that the noise 3' is canceled at a position proximate to the ear of the listener 1.

The noise 3 collected by the microphone 31 and the noise 3' in the headphone housing 2 have different characteristics according to a difference between the spatial positions of them (including a difference between the outside and the inside of the headphone housing 2). Accordingly, in the noise reduction system of the feedforward type, a noise reduction sound signal is produced taking the difference in spatial transfer function between the noise from the noise source 3 collected by the microphone 31 and the noise 3' at the cancel point Pc into account.

In the present embodiment, the digital filter circuit 33 is used as a noise reduction sound signal generation section of the feedforward type. In the present embodiment, since a noise reproduction sound signal is generated by the feedforward system, the digital filter circuit 33 is hereinafter referred to as FF filter circuit 33.

The FF filter circuit 33 includes a DSP (Digital Signal Processor) 332, an A/D conversion circuit 331 provided at the preceding stage to DSP 332 and a D/A conversion circuit 333 provided at the succeeding stage to the DSP 332 quite similarly to the FB filter circuit 23.

Figure 34:
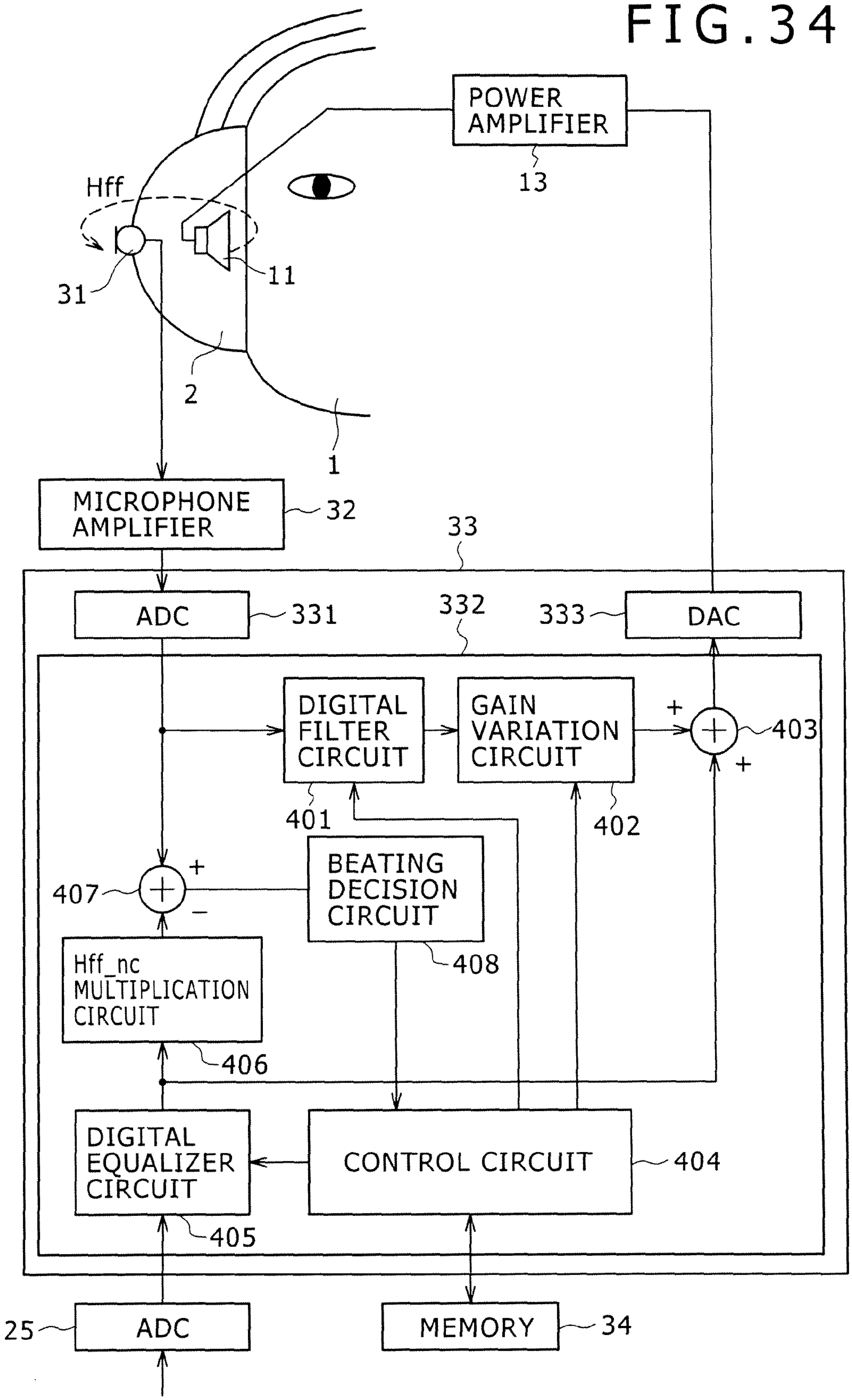
FIG. 34 is a block diagram showing an example of a detailed configuration of an FF filter circuit shown in FIG. 33.

Referring now to FIG. 34, in the present embodiment, the DSP 332 includes a digital filter circuit 401, a gain variation circuit 402, an addition circuit 403, a control circuit 404, a digital equalizer circuit 405, a transfer function Hff multiplication circuit 406, a subtraction circuit 407 which forms an example of a removing circuit, and a beating decision circuit 408.

An analog sound signal collected by the microphone 31 is supplied through the microphone amplifier 32 to the FF filter circuit 33 as shown in FIG. 34, by which it is converted into a digital sound signal by the A/D conversion circuit 331. Then, the digital sound signal is supplied to the digital filter circuit 401 of the DSP 332.

The digital filter circuit 401 of the DSP 332 is provided to generate a digital noise reduction sound signal using the feedforward system. The digital filter circuit 401 generates, from a digital sound signal inputted thereto, a digital noise reduction sound signal of a characteristic according to filter coefficients as parameters set to the digital filter circuit 401. The filter coefficients to be set to the digital filter circuit 401 are read out from the memory 34 and supplied to the digital filter circuit 401 by the control circuit 404.

In the present embodiment, in order to make it possible to reduce noise in a plurality of various different noise environments using a noise reduction sound signal according to the feedforward system generated by the digital filter circuit 401 of the DSP 332, such a plurality of filter coefficients or a plurality of sets of filter coefficients as parameters as hereinafter described are stored in the memory 34.

The control circuit 404 reads out a particular one filter coefficient or a particular one set of filter coefficients from the memory 34 and sets the filter coefficient or coefficients to the digital filter circuit 401 of the DSP 332 similarly as in the first embodiment described hereinabove.

Further, in the present embodiment, a beating decision signal is supplied from the beating decision circuit 408 to the control circuit 404. Thus, when the control circuit 404 decides that the beating decision signal from the beating decision circuit 408 indicates that the headphone housing 2 is beaten once by the user, the control circuit 404 alters the particular one filter coefficient or the particular one set of filter coefficients to be read out from the memory 34 and sets the altered filter coefficient or coefficients to the digital filter circuit 401.

Then, the digital filter circuit 401 generates a digital noise reduction sound signal according to the filter coefficient or coefficients selectively read out from the memory 34 and set thereto by the control circuit 404.

The digital noise reduction sound signal generated by the digital filter circuit 401 is supplied to the addition circuit 403 through the gain variation circuit 402 as seen in FIG. 34. In the present embodiment, the gain of the gain variation circuit 402 is controlled upon changeover alteration of the noise mode under the control of the control circuit 404.

On the other hand, a sound signal S of an object of listening such as, for example, a music signal inputted through the sound signal input terminal 12 is converted into a digital sound signal by an A/D conversion circuit (ADC) 25 and then supplied to the digital equalizer circuit 405 of the DSP 332. Consequently, the sound signal S in the form of a digital sound signal is subjected to amplitude-frequency characteristic correction or phase-frequency characteristic correction or both of them by the digital equalizer circuit 405.

In the noise reduction system of the feedforward type, even if the filter coefficient of the digital filter circuit 401 is altered to alter the noise reduction curve, that is, the noise reduction characteristic, the externally inputted sound signal S of an object of listening is not subject to the influence corresponding to the frequency curve or frequency characteristic of the noise reduction effect. Therefore, in the present second embodiment, when a noise mode changeover alteration process is performed, the control circuit 404 does not perform an alteration process of the equalizer characteristic of the digital equalizer circuit 405.

It is to be noted, however, that, similarly as in the first embodiment, also in the present second embodiment, a user can issue an instruction to alter the equalizer characteristic of the digital equalizer circuit 405. Therefore, also in the present second embodiment, when the headphone housing 2 is beaten once, the one beating operation is decided as a noise mode alteration input command, but when the headphone housing 2 is beaten twice, the two beating operations are decided as an equalizer characteristic alteration instruction command.

An output sound signal of the digital equalizer circuit 405 is supplied to the addition circuit 403, by which it is added to the noise reduction sound signal from the gain variation circuit 402. Then, a resulting sum signal is supplied as an output of the DSP 332 to the D/A conversion circuit 333, by which it is converted into an analog sound signal. Then, the analog sound signal is supplied as an output signal of the FF filter circuit 33 to a power amplifier 13. Then, the sound signal from the power amplifier 13 is supplied to and acoustically reproduced by the driver 11 so that reproduction sound then is emitted toward the ears (in FIGS. 33 and 34, only the right ear is shown) of the listener 1.

The sound acoustically reproduced and emitted from the driver 11 includes an acoustic reproduction component from the noise reduction sound signal generated by the FF filter circuit 33. The acoustic reproduction component from the noise reproduction sound signal from within the sound acoustically reproduced and emitted from the driver 11 and the noise 3' are acoustically synthesized so that the noise 3' is reduced or canceled at the noise cancel point Pc.

Figure 35:
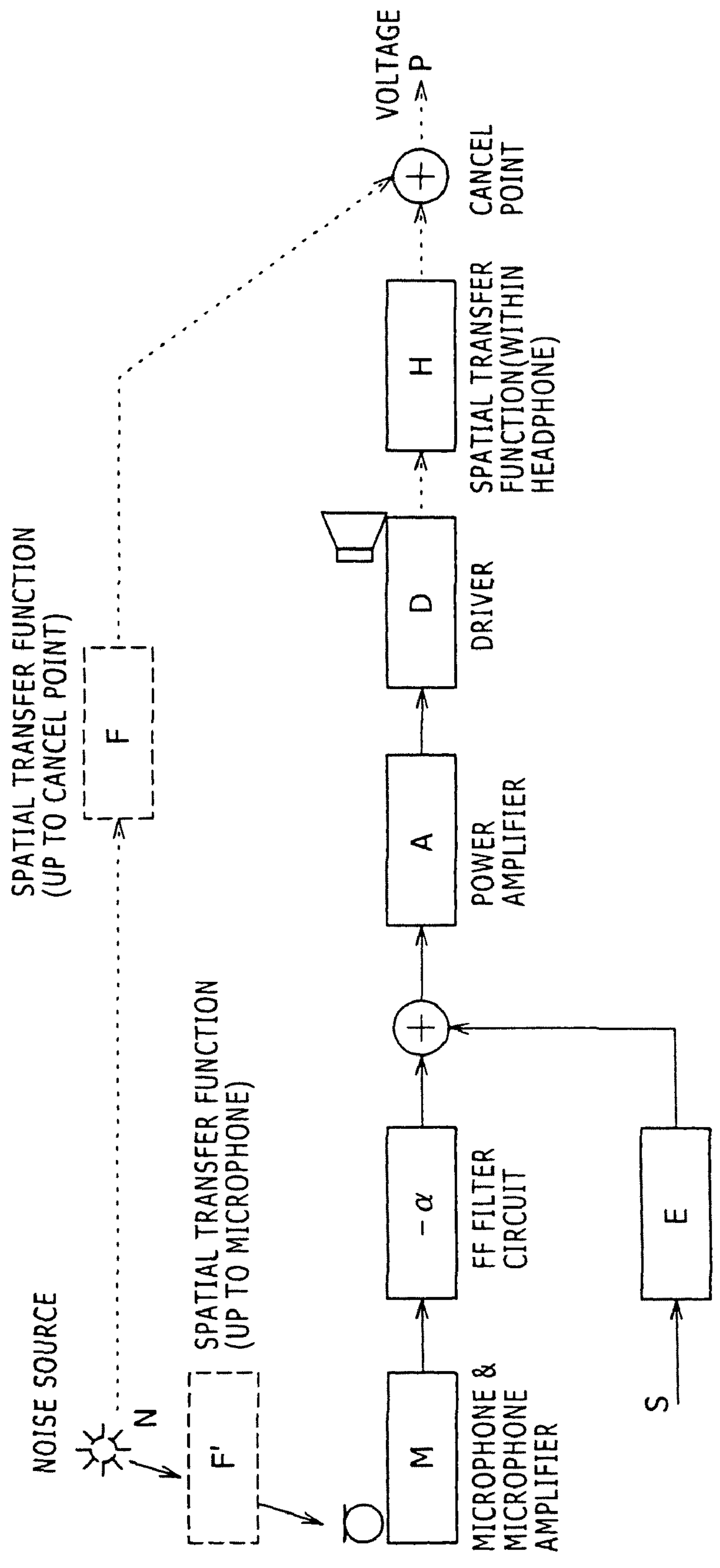
FIG. 35 is a block diagram showing a configuration of a noise reduction apparatus section in the sound outputting apparatus according to the second embodiment of the present invention using a transfer function.

Now, a noise reproduction operation of the noise reproduction apparatus of the feedforward type is described with reference to FIG. 35 using transfer functions. FIG. 35 shows a block diagram wherein different components of the noise reduction apparatus section 30 shown in FIG. 33 are represented using their transfer functions.

Referring to FIG. 35, reference character A denotes the transfer function of the power amplifier 13; D the transfer function of the driver 11; M the transfer function of the microphone 31 and the microphone amplifier 32; and $-\alpha$ the transfer function of the digital filter circuit 401 designed for the feedforward system. Further, reference character H denotes the transfer function of the space from the driver 11 to the cancel point Pc; and E the transfer function of the digital equalizer circuit 405 applied to the sound signal S of the listening object. Furthermore, reference character F denotes the transfer function from the position of noise N of the external noise source 3 to the position of the cancel point Pc of the ear of the listener 1.

Where the noise reduction apparatus is represented in such a manner as seen in FIG. 35, the blocks shown in FIG. 35 can be represented by an expression 5 of FIG. 4. It is to be noted that reference character F' represents the transfer function from the noise source to the position of the microphone. The transfer functions given above are represented in complex representations.

Here, an idealistic state is assumed. If the transfer function F can be represented in such a manner as given by an expression 6 of FIG. 4, then the expression 5 of FIG. 4 can be represented by an expression 7 of FIG. 4. From the expression 7, it can be recognized that the noise is canceled while only the reproduction sound signal S or the music signal or the like of an object of listening remains and the user can listen to sound similar to that in an ordinary headphone operation. The sound pressure P in this instance can be represented by the expression 7 of FIG. 4.

It is to be noted, however, that it is actually difficult to form a perfect filter having such a transfer function as fully satisfies the expression 6 of FIG. 4. Usually, for sound in the medium and high frequency region, such an active noise reproduction process as described above is not performed but passive sound insulation is applied frequently using the headphone housing 2 from such reasons as that, particularly with regard to the medium and high frequency region, the difference among individuals is great depending upon mounting or the shape of the ears and that the characteristic varies depending upon the position of noise or the position of the microphone.

It is to be noted that, while the expression 6 of FIG. 4 signifies that, although it is self-evident from the expression, the transfer function from the noise source to the ear position is simulated by an electric circuit including the transfer function α of the digital filter.

It is to be noted that, as seen in FIG. 33, the cancel point in the feedforward system according to the second embodiment can be set to an arbitrary ear position of the listener, different from that in the feedback system according to the first embodiment shown in FIG. 1.

However, in a normal case, the transfer function α of the digital filter circuit 401 is fixed, and at the stage of designing, it is determined from some target characteristic, and depending upon a person, a phenomenon that a sufficient noise cancel effect may not be obtained because the shape of the ear is different, or since a noise component is added not in a reverse phase, such a phenomenon that abnormal sound is generated occurs.

Figure 36:
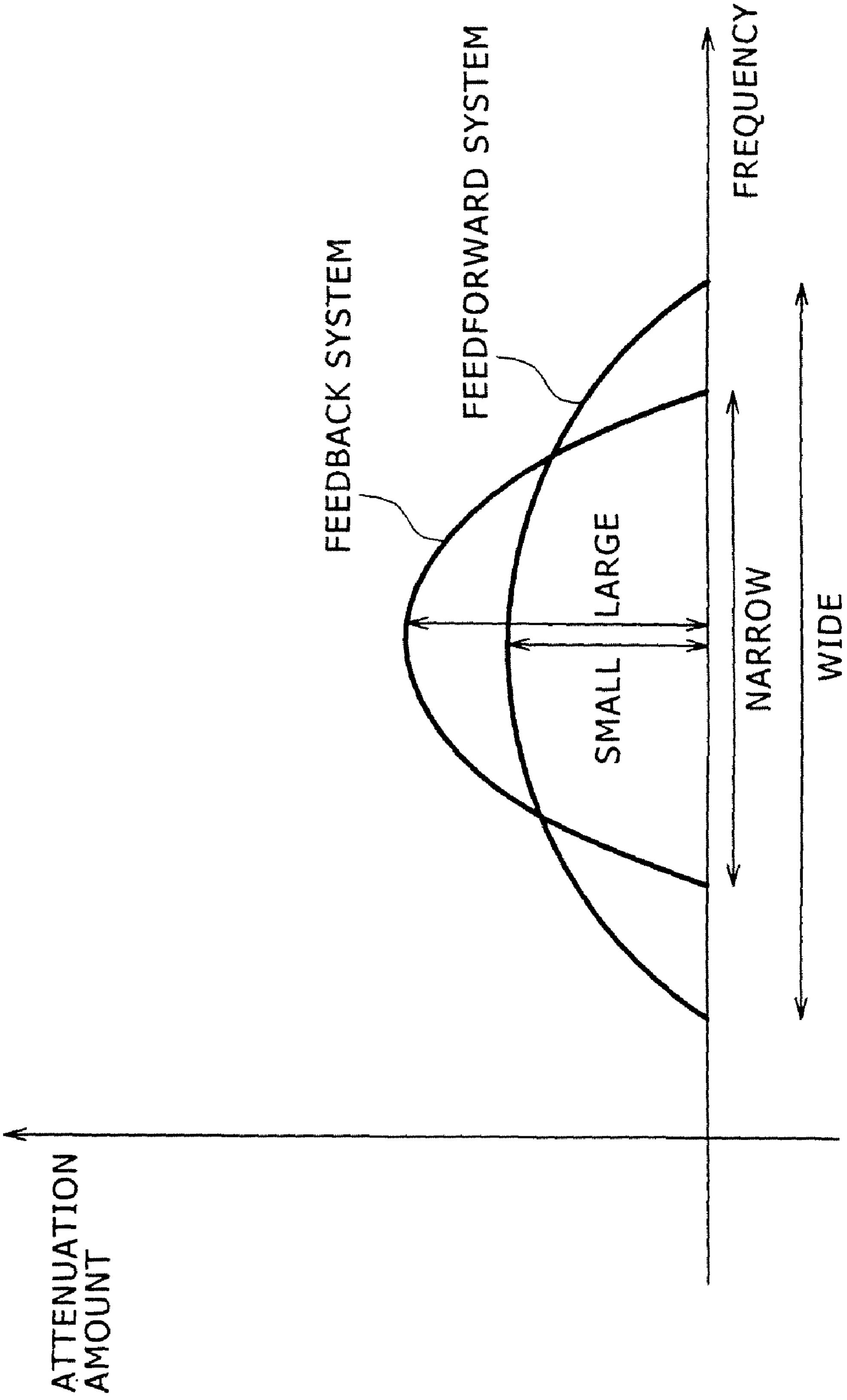
FIG. 36 is a graph illustrating attenuation characteristics of a noise reduction system of a feedback type and a noise reduction system of a feedforward type.

Generally, as seen in FIG. 36, the feedforward system of the second embodiment is low in possibility of oscillation and high in stability, but it is difficult for the feedforward system to obtain a sufficient attenuation amount. Meanwhile, the feedback system of the first embodiment necessitates attention in stability while a great attenuation amount can be anticipated.

Decision of beating of the headphone housing 2 in the present second embodiment is performed from a collected sound signal from the microphone 31. In this instance, the collected sound signal from the microphone 31 is influenced by a reproduction sound signal which is a component of reproduction music of an object of listening or of communication voice and also by a noise reduction effect. When the user beats the headphone housing 2, although the sound generated from the beaten headphone housing 2 is collected naturally by the microphone 31, since reproduction sound is emitted from the driver 11 simultaneously, there is the possibility that the beating sound of the headphone housing 2 may be embedded in the reproduction sound. Therefore, if no countermeasure is taken, then it is difficult to detect beating of the headphone housing 2 from the collected sound signal from the microphone 31.

Therefore, in the present second embodiment, the component of acoustic reproduction sound of the sound signal S is removed so that a beating operation can be decided with certainty.

First, where the transfer function from the driver 11 to the microphone 31 is represented by Hff, a filter Hff_nc is calculated in advance by multiplying a factor of the transfer function Hff by a frequency characteristic influence of an external sound signal by a noise reduction effect in the noise mode selected currently. Then, upon actual use, a sound signal of an object of reproduction is passed through the digital equalizer circuit 405 and then multiplied by the filter Hff_nc and is then subtracted from the output signal of the microphone 31. Then, a beating decision is made based on the subtraction output signal.

In short, a sound signal issued from the driver 11 is simulated as accurately as possible at the position of the microphone 31 and then is subtracted from the sound at the position of the microphone 31 to remove the component of the reproduction sound signal S from the collected sound signal of the microphone 31.

In particular, in the present second embodiment, the collected sound signal from the microphone 31 is supplied to the subtraction circuit 407 after it is converted into a digital sound signal by the A/D conversion circuit 331 as seen from FIG. 34.

On the other hand, the sound signal S from the digital equalizer circuit 405 is supplied to the filter Hff_nc multiplication circuit 406, by which it is multiplied by the filter Hff_nc determined with the transfer function Hff taken into consideration. Then, a result of the multiplication is supplied to the subtraction circuit 407, by which it is subtracted from the collected sound signal from the microphone 31 thereby to remove the component of the sound signal S included in the collected sound signal.

Then, the collected sound signal of the microphone 31 from which the component of the sound signal S from the subtraction circuit 407 is removed is supplied to the beating decision circuit 408. The beating decision circuit 408 decides whether or not the collected sound signal from the microphone 31 includes a sound signal component or an oscillation component produced when the headphone housing 2 is beaten. Further, the beating decision circuit 408 decides the number of times of beating depending upon how many components are included within a predetermined period of time. Then, the beating decision circuit 408 supplies a result of the decision to the control circuit 404.

While the subtraction result obtained from the subtraction circuit 407 includes much environmental noise, sound transmitted by the headphone housing 2 when the headphone housing 2 is beaten by the user is generally louder than such environmental noise. Further, pulse-like sound as is produced upon beating normally is not included in the environmental noise. Therefore, such environmental noise is not likely to be recognized in error.

Figure 37:
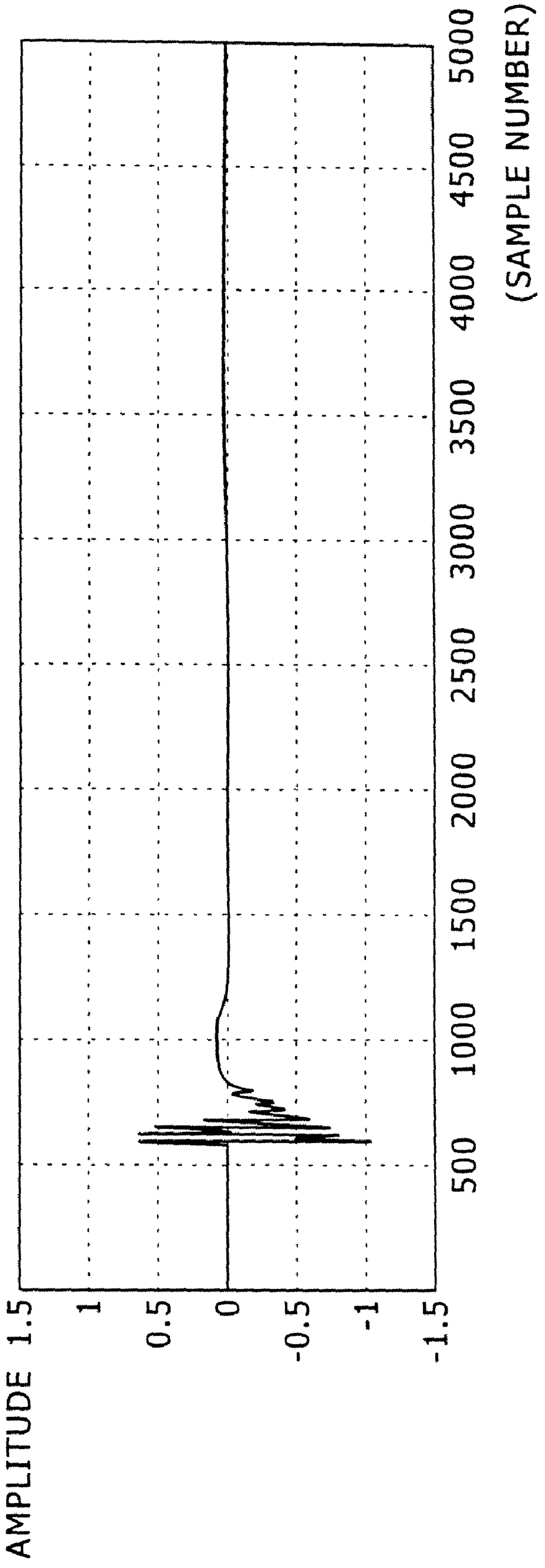
FIG. 37 is a graph illustrating a first example of a beating decision method for the sound outputting apparatus according to the second embodiment of the present invention.

The beating decision circuit 408 may have a particular configuration quite similar to that in the first embodiment described hereinabove. It is to be noted, however, that, in the present second embodiment, representative beating waveform data obtained form the microphone 31 when the headphone housing 2 is beaten are such as illustrated in FIG. 37. Accordingly, in the first example of beating decision, the beating waveform data to be stored into the memory 34 are such beating waveform data as illustrated in FIG. 37.

On the other hand, in the second example of beating decision, the beating waveform shape can be decided by decision of a maximum value and decision of the attenuation ratio regarding samples within preceding and succeeding intervals to the maximum value based on such waveform data as seen in FIG. 37.

Also in the second embodiment, a noise mode changeover alteration process and an equalizer characteristic alteration process are performed based on the beating decision under the control of the control circuit 404 in a quite similar manner as in the first embodiment.

Then, upon changeover alteration of the noise mode described above, the control circuit 404 performs such control operation as described hereinabove in connection with the first to third examples in the first embodiment described hereinabove.

Third and Fourth Embodiments

Incidentally, in the noise reproduction apparatus section in the first and second embodiments described hereinabove, the filter circuit is formed as a digital filter circuit and a plurality of different filter coefficients are prepared in a memory. Then, an appropriate filter coefficient is selected from among the filter coefficients and set to the digital filter.

However, the FB filter circuit 23 and the FF filter circuit 33 each formed as a digital filter circuit have a problem of delay in the A/D conversion circuit 231 or 331 and the D/A conversion circuit 233 or 333. The problem of delay is described below in connection with a noise reduction system of the feedback type.

For example, as a general example, where an A/D conversion circuit and a D/A conversion circuit whose sampling frequency Fs is 48 kHz are used, if the delay amount in the inside of the A/D conversion circuit and the D/A conversion circuit is 20 samples respectively, then a delay of totaling 40 samples is included in the block of the FB filter circuit 23 in addition to arithmetic operation delay in the DSP. As a result, the delay is applied as a delay of an open loop to the entire system.

Figure 38A:
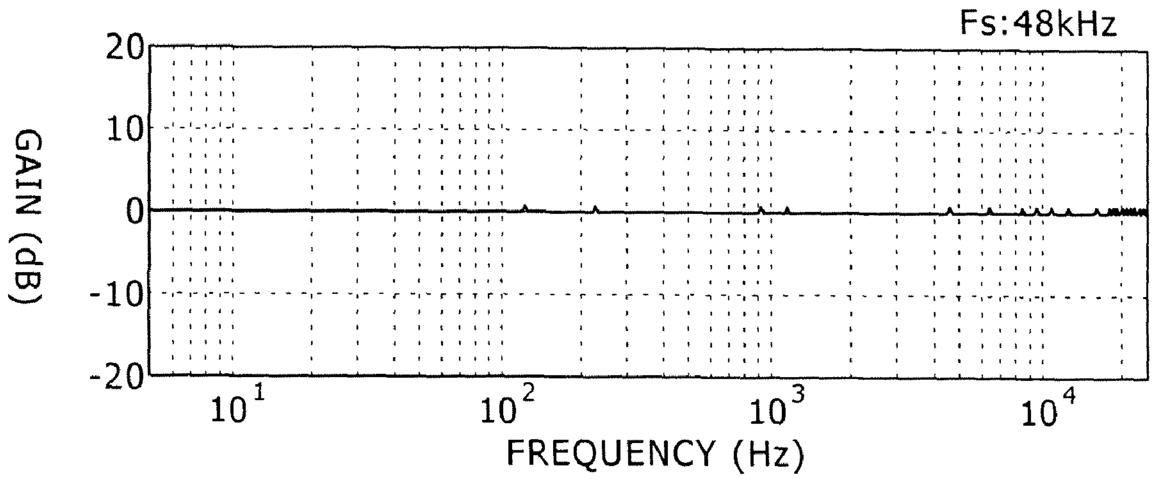
FIGS. 38 to 41B are views illustrating third and fourth embodiments of the present invention.
Figure 38B:
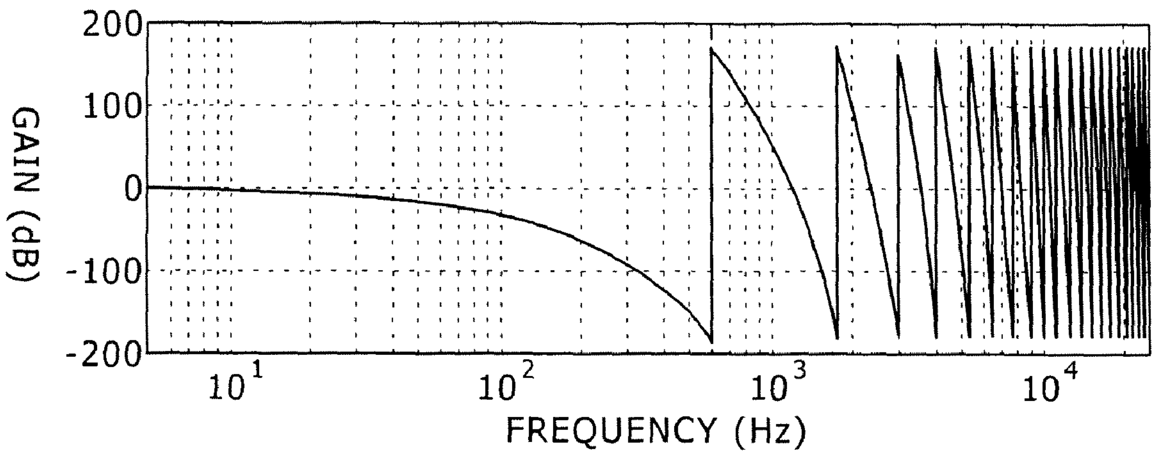
Figure 39A:
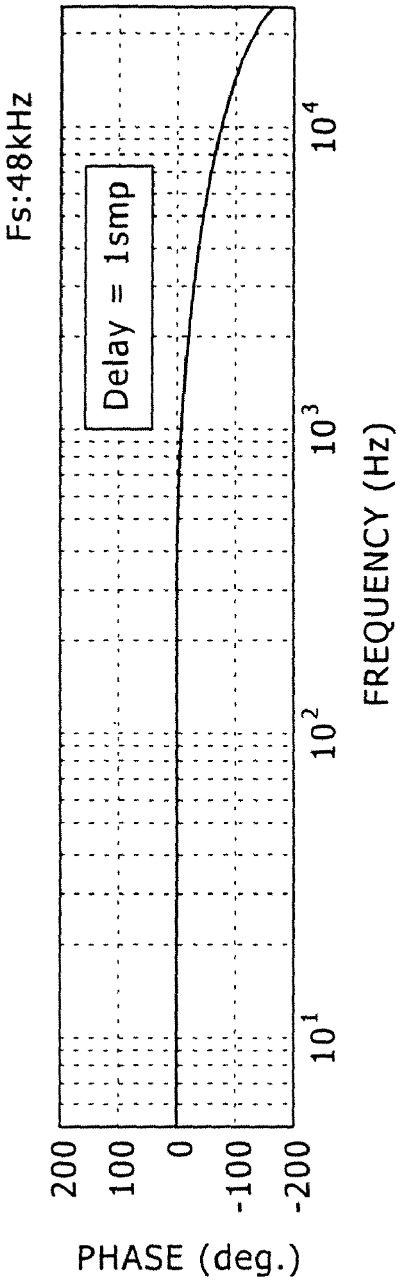
Figure 39B:
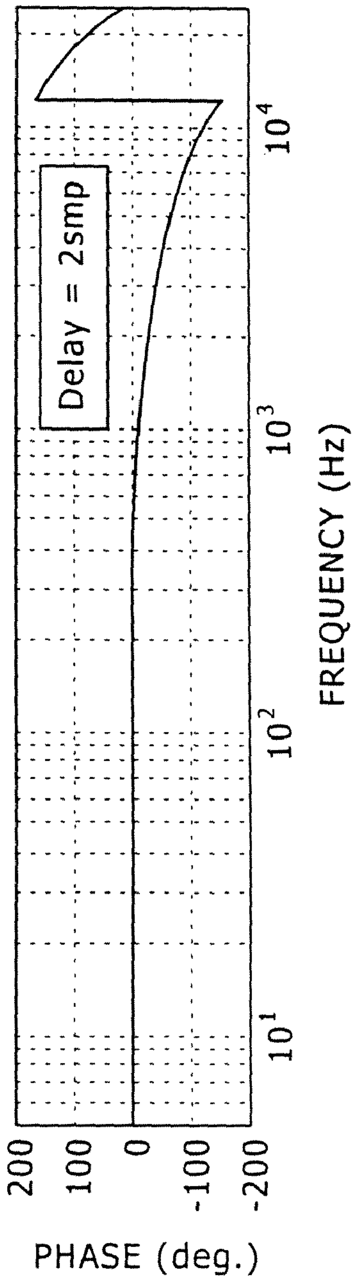
Figure 39C:
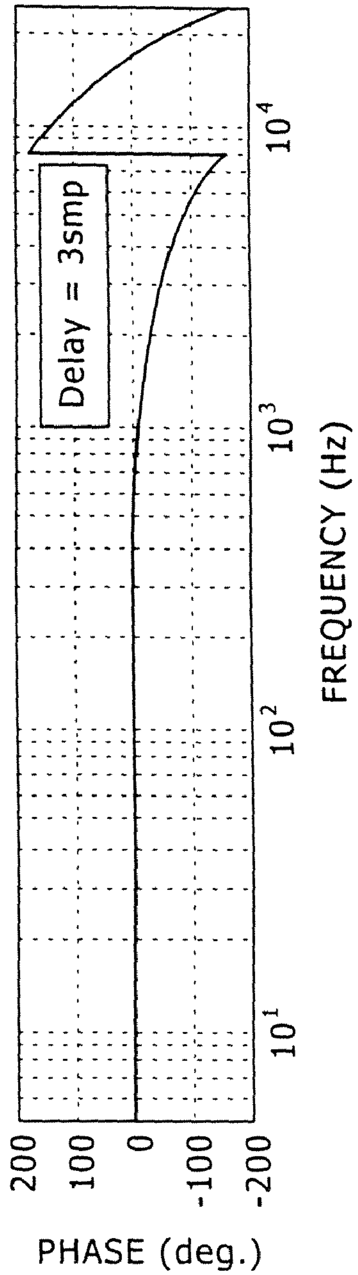

In particular, while gain and phase characteristics corresponding to a delay amount of 40 samples in a sampling frequency of 48 kHz are illustrated in FIGS. 38A and 38B, respectively, it can be seen that phase rotation starts at several tens Hz and the phase rotates by a great amount up to the frequency of Fs/2 (24 kHz). This can be recognized readily if it is recognized that, as seen in FIGS. 39A to 39C, a delay by one sample in the sampling frequency of 48 kHz corresponds to a delay of 180 degrees ($\pi$) at the frequency of Fs/2 and delays of 2 samples and 3 samples correspond to delays by $2\pi$ and $3\pi$, respectively.

Figure 40A:
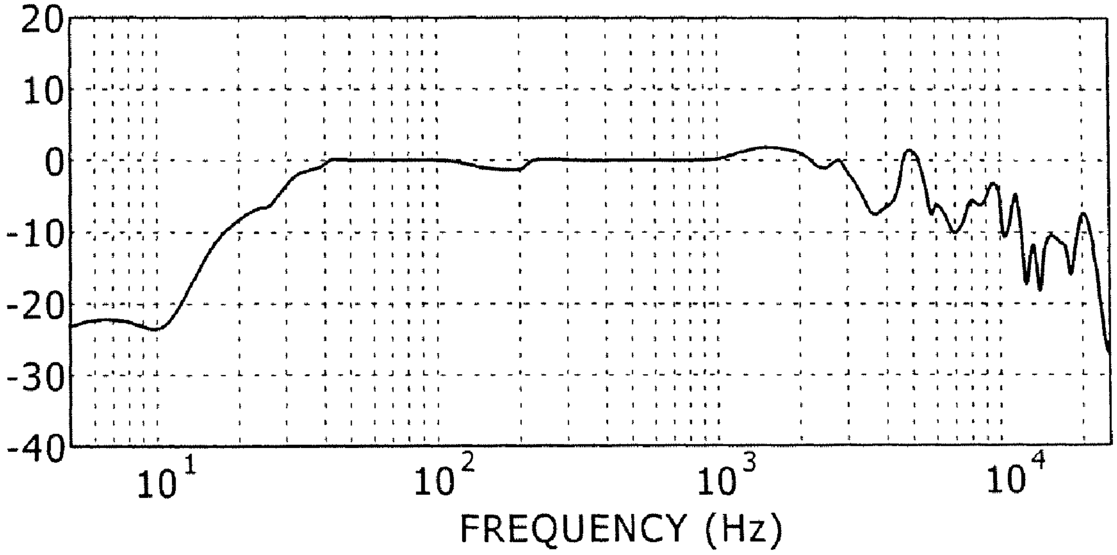
Figure 40B:
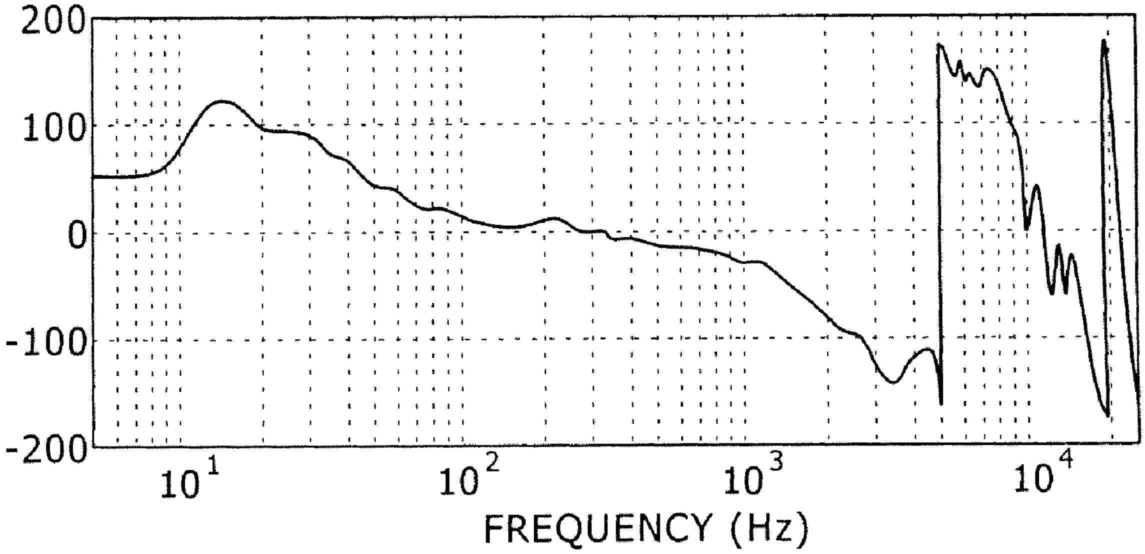

On the other hand, a gain characteristic and a phase characteristic when the transfer function from the position of the driver 11 to the microphone 21 in a headphone configuration which has an actual noise reduction system of the feedback type is measured are illustrated in FIGS. 40A and 40B, respectively. In this case, the microphone 21 is disposed at the vicinity of the front surface of the diaphragm of the driver 11, distance between them is small, thus the phase rotation is relatively small.

The transfer function illustrated in FIGS. 40A and 40B corresponds to ADHfbM in the expression 1 and the expression 2 illustrated in FIG. 4, and if the transfer function and a filter having a characteristic of a transfer function $-\beta$ are multiplied on the frequency axis, then an open loop is obtained directly. It is necessary for the shape of the open loop to satisfy the conditions described hereinabove with reference to the expression 2 of FIG. 4 and with reference to FIG. 5.

Here, if the phase characteristic of FIG. 38A is viewed again, then it can be seen that the phase begins to rotate from 0 degree and makes one rotation ($2\pi$) in the proximity of 1 kHz. In addition, also in the ADHfbM characteristic of FIG. 40B, a phase delay exists depending upon the distance from the driver 11 to the microphone 21.

In the FB filter circuit 23, the digital filter section formed from the DSP 232 which can be designed freely is connected in series to delay components of the A/D conversion circuit 231 and the D/A conversion circuit 233. However, in the digital filter section, it is basically difficult to design a phase-leading filter from the law of causality. It is to be noted, however, that, although "partial" phase leading only within a particular frequency band is possible depending upon the configuration of the filter shape, it may be impossible to form a phase leading circuit for such a wide frequency band as compensates for phase rotation by the delay.

Where this is taken into consideration, even if a suitable digital filter of the transfer function $-\beta$ is designed from the DSP 232, the frequency band within which a noise reduction effect can be obtained with the feedback configuration in this instance is restricted to a region lower than the proximity of 1 kHz at which the phase makes one rotation. Thus, it can be recognized that, if an open loop wherein an ADHM characteristic is incorporated is assumed and a phase margin and a gain margin are taken into consideration, then the attenuation amount and the attenuation frequency band are further restricted.

Figure 41A:
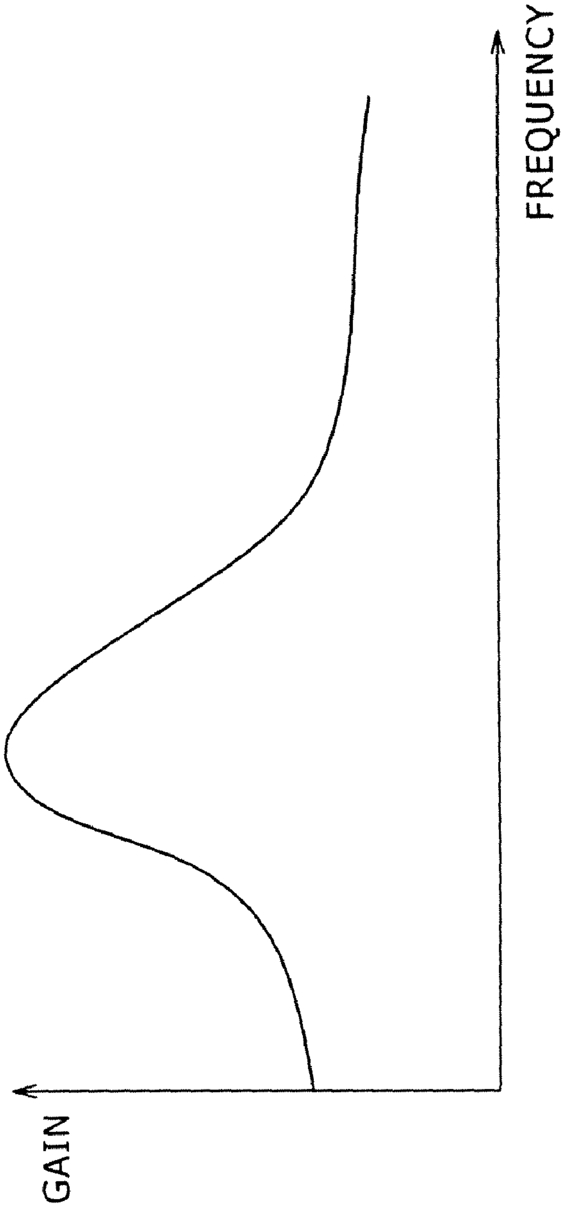

In this significance, it can be recognized that a characteristic desirable to such characteristics as seen in FIGS. 40A and 40B (phase reversing system in the block of the transfer function $-\beta$) is a gain shape with which, while a substantially mountain-like shape is maintained within a frequency band within which a noise reduction effect is intended, phase rotation does not occur very much (in FIG. 41A, the phase characteristic from a low frequency region to a high frequency region does not exhibit one rotation). Therefore, it is a current target to design the entire system so that the phase does not make one rotation.

It is to be noted that, essentially, if the phase rotation is small in an object frequency band (principally the low frequency region) of noise reduction, then the phase variation out of the frequency band has no relation as long as the gain is in a dropped state. However, generally since, if the phase rotation is great in the high frequency region, this has not a little influence also on the low frequency region, it is an object of the present embodiment to make a design so that the phase rotation becomes small over a wide frequency band.

Figure 41B:
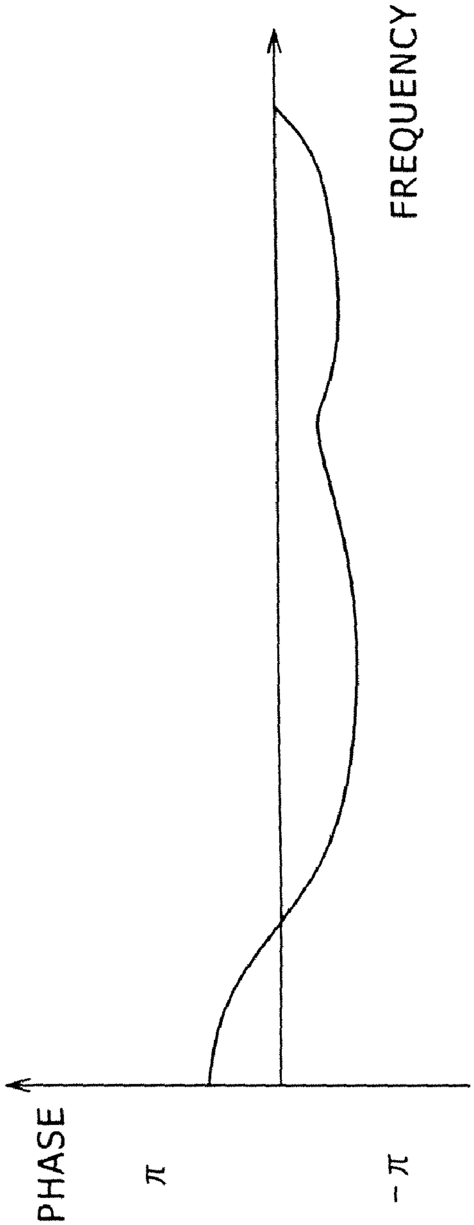

Further, such characteristics as seen in FIGS. 41A and 41B can be designed from an analog circuit. In this significance, it is not preferable for the noise reduction effect to be reduced much when compared with the alternative case wherein the system is designed from analog circuitry in exchange for the merits described hereinabove where the system is formed from a digital filter.

Incidentally, if the sampling frequency is raised, then the delay in the A/D conversion circuit and the D/A conversion circuit can be reduced. However, if the sampling frequency is raised, then the product becomes very expensive and can be implemented as a product for military purposes or for business purposes. However, where the product is applied as a product for general consumers such as a headphone apparatus for music listening, the price becomes very high, and the product is low in practicality.

Therefore, in the third and fourth embodiments, a technique is provided which can increase the noise reduction effect while making the most of the merits of digitalization by the first and second embodiments.

Figure 42:
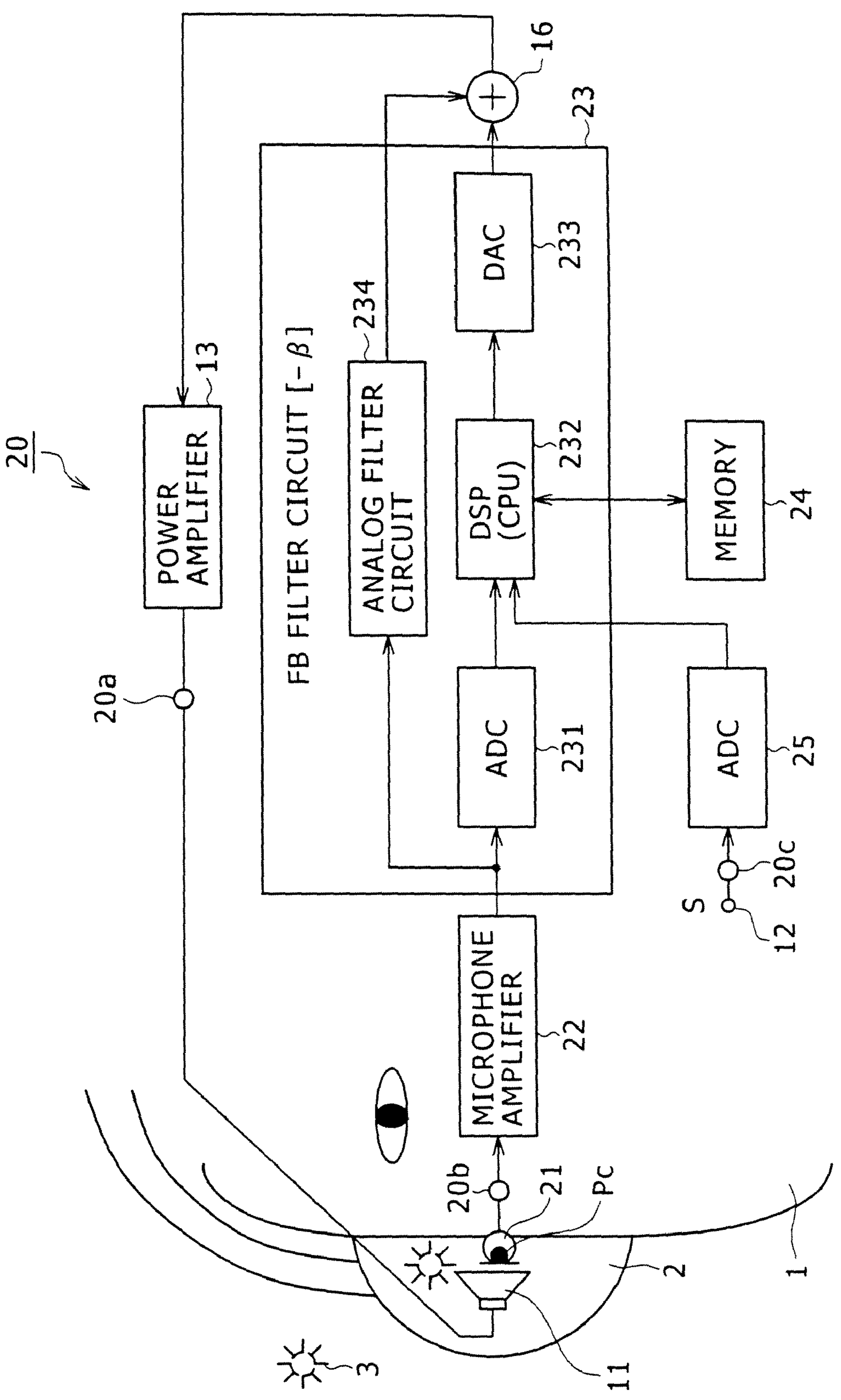
FIG. 42 is a block diagram showing an example of a headphone apparatus to which the third embodiment of the present invention is applied.

FIG. 42 shows a configuration of a headphone apparatus according to the third embodiment of the present invention. The headphone apparatus of the third embodiment improves the configuration of the noise reduction apparatus section 20 which uses the feedback system according to the first embodiment.

Referring to FIG. 42, in the headphone apparatus of the third embodiment, the FB filter circuit 23 includes an analog processing system formed from an analog filter circuit 234 connected in parallel to a digital processing system which includes an A/D conversion circuit 231, a DSP 232 and a D/A conversion circuit 233.

An analog noise reduction sound signal generated by the analog filter circuit 234 is supplied to an addition circuit 16. Also an analog signal from the D/A conversion circuit 233 is supplied to the addition circuit 16, by which it is added to the analog signal from the analog filter circuit 234. An output signal of the addition circuit 16 is supplied to a power amplifier 13. The configuration of the remaining part of the headphone apparatus is similar to that described hereinabove with reference to FIG. 1.

It is to be noted that the analog filter circuit 234 shown in FIG. 42 may actually be configured such that it passes an input sound signal therethrough without performing a filter process therefor so as to be supplied as it is to the addition circuit 16. In this instance, since an analog element is not included in the analog processing system, the system has high reliability in terms of the dispersion and the stability.

In the FB filter circuit 23 in the present third embodiment, the filter coefficients to be stored in the memory 24 described hereinabove are designed such that results of addition of signals after processed in parallel by the digital processing system and the analog processing system have such a gain characteristic and a phase characteristic as illustrated in FIGS. 41A and 41B, respectively, as characteristics of the transfer function β.

With the headphone apparatus of the third embodiment, since the path of the analog processing system is added in parallel to the path of the digital processing system, the problems described hereinabove can be moderated and excellent noise reduction can be achieved in accordance with various noise environments.

Figure 43A:
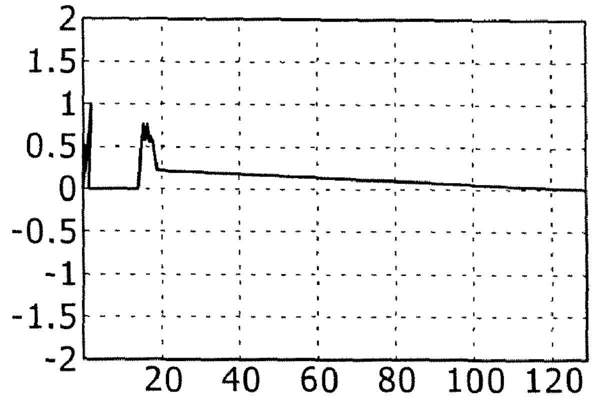
FIGS. 43A to 43C are views illustrating a characteristic of a noise reduction apparatus section in a sound outputting apparatus according to the third embodiment of the present invention.
Figure 43B:
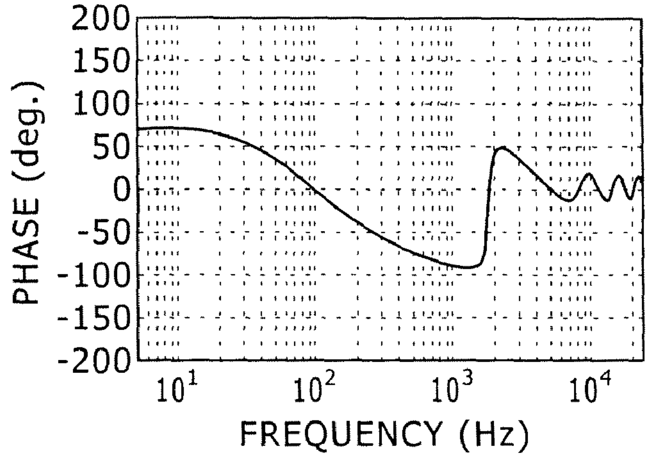
Figure 43C:
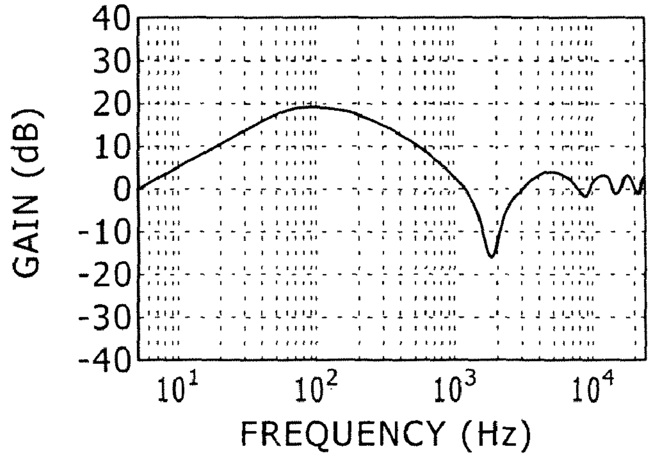

Characteristics where the path of the analog processing system (through which a signal passes) is added in parallel to the path of the digital processing system are illustrated in FIGS. 43A to 43C. FIG. 43A illustrates a top portion (up to the 128th sample) of the impulse response of the transfer function in the case of the present example, and FIGS. 43B and 43C illustrate the phase characteristic and the gain characteristic, respectively.

From FIG. 43B, it can be seen that, with the headphone apparatus of the third embodiment, phase rotation is suppressed by addition of the analog path and the phase does not exhibit one rotation over a wide range from the low frequency region to the high frequency region.

If the characteristics are viewed from a different aspect, then the low frequency region characteristic on which the noise reduction is stressed is subject to an increasing influence from the processing system composed of a digital filter. Meanwhile, in regard to the middle and high frequency regions in which phase rotation is likely to become great by delay by the A/D conversion circuit and the D/A conversion circuit, the characteristic of the analog path having a high responsibility is utilized effectively.

In this manner, according to the third embodiment of the present invention, a noise reproduction apparatus and a headphone apparatus can be provided wherein noise can be reduced in conformity with various noise environments without increasing the scale of the configuration.

While the third embodiment achieves noise reduction of the feedback type, it can be applied similarly also where noise reduction of the feedforward type of the second embodiment is involved.

Also in the third embodiment described above, such control operation as described hereinabove in connection with the first embodiment is performed under the control of the control circuit 304 of the DSP 232.

Figure 44:
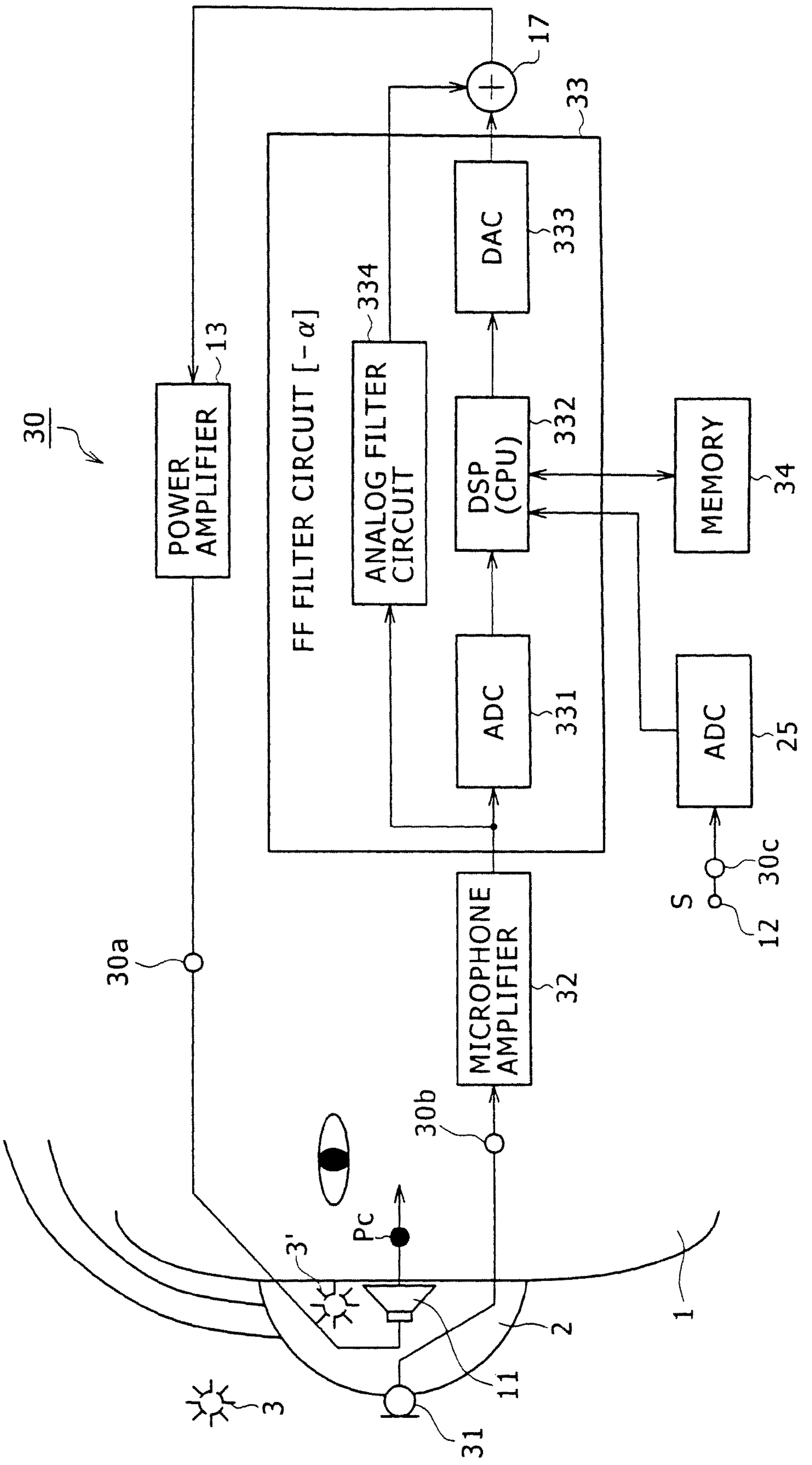
FIG. 44 is a block diagram showing an example of a headphone apparatus to which the fourth embodiment of the present invention is applied.

The fourth embodiment improves the second embodiment which involves noise reduction of the feedforward type in terms of the problems where only a digital filter is used described hereinabove and the example of configuration is shown in FIG. 44.

In particular, in the present fourth embodiment, the FF filter circuit 33 is configured such that an analog processing system formed from an analog filter circuit 334 is added in parallel to a digital processing system which includes an A/D conversion circuit 331, a DSP 332 and a D/A conversion circuit 333.

An analog noise reduction sound signal generated by the analog filter circuit 334 and an analog signal from the D/A conversion circuit 333 are added by an addition circuit 17. An addition output signal of the addition circuit 17 is supplied to the power amplifier 13. The configuration of the remaining part of the headphone apparatus is similar to that described hereinabove with reference to FIG. 33.

It is to be noted that the analog filter circuit 334 shown in FIG. 44 may actually be configured such that it passes an input sound signal therethrough without performing a filter process therefor so that the input sound signal is supplied as it is to the addition circuit 17. In this instance, since an analog element is not included in the analog processing system, the system has high reliability in terms of the dispersion and the stability.

In the FF filter circuit 33 in the present fourth embodiment, the filter coefficients to be stored in the memory 34 described hereinabove are designed such that results of addition of signals after processed in parallel by the digital processing system and the analog processing system have such a gain characteristic and a phase characteristic as illustrated in FIGS. 41A and 41B, respectively, as characteristics of the transfer function α.

It is to be noted that the memory controller in the embodiments described hereinabove may be provided in the DSPs 232 and 332, respectively. Also the A/D conversion circuit 25 may be provided in the DSP 232 or 332 such that it converts the sound signal S into a digital signal and supplies the digital signal to the equalizer circuit in the DSP 232 or 332.

Also in the fourth embodiment described above, such control operation as described hereinabove in connection with the second embodiment is performed under the control of the control circuit 404 of the DSP 332.

Fifth Embodiment

As described hereinabove, although the feedforward system of the second embodiment is low in possibility of oscillation and high in stability, it is difficult to obtain a sufficient attenuation amount. On the other hand, the feedback system of the first embodiment necessitates attention in stability while a great attenuation amount can be anticipated.

Therefore, the present fifth embodiment provides a noise reduction system which achieves the advantages of both systems. In particular, referring to FIG. 45, in the present fifth embodiment shown, the noise reduction system includes a noise reduction apparatus section 20 of the feedback type and a noise reduction apparatus section 30 of the feedforward type.

Figure 45:
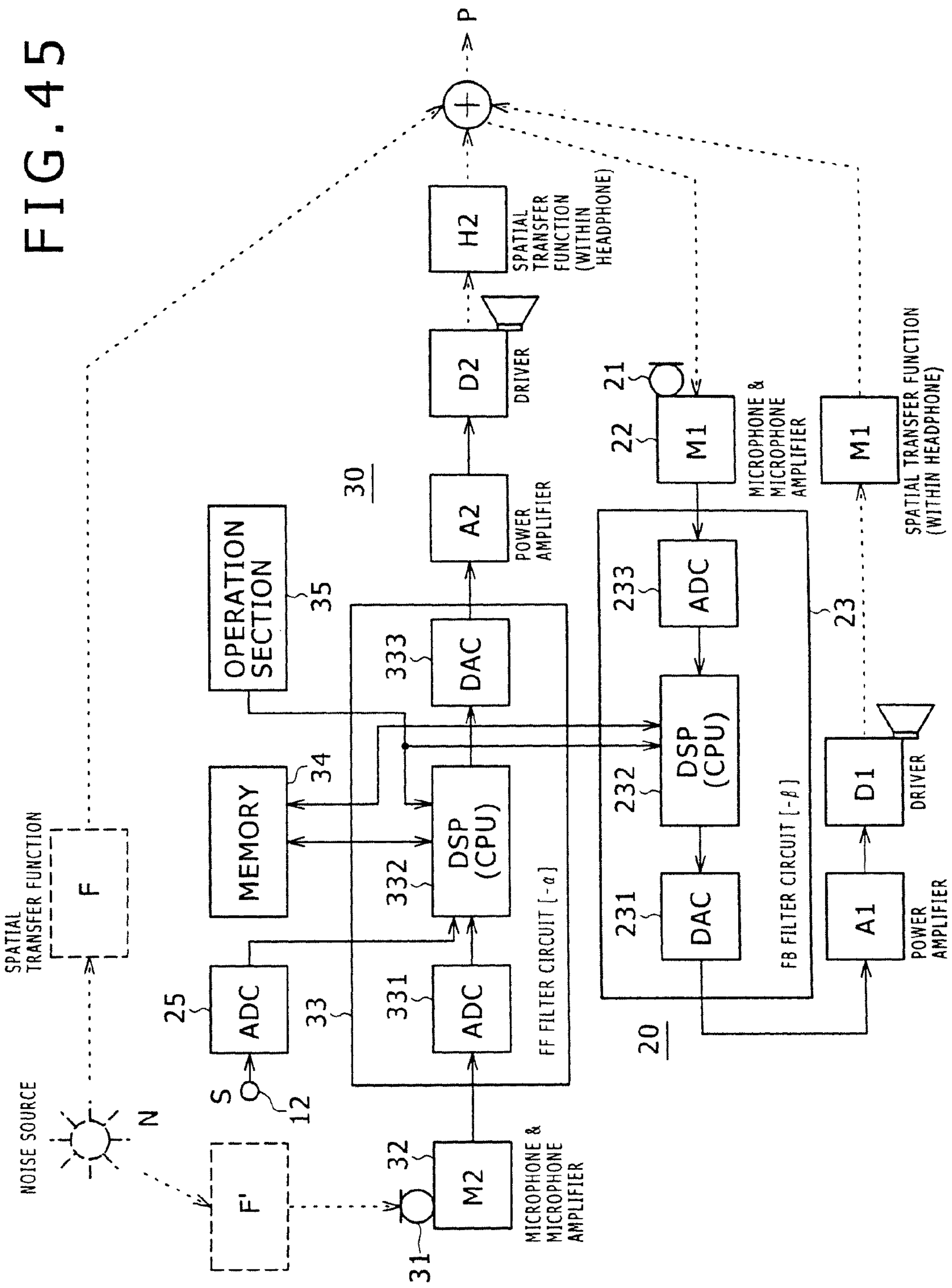
FIG. 45 is a block diagram showing an example of a headphone apparatus to which a fifth embodiment of the present invention is applied.

It is to be noted that, in FIG. 45, a block configuration is shown using transfer functions. In particular, in the noise reduction apparatus section 20 of the feedback type, the transfer function of a portion corresponding to a microphone 21 and an microphone amplifier 22 is represented by M1; the transfer function of a power amplifier for amplifying a noise reduction sound signal generated by the FB filter circuit 23 by A1; and the transfer function of a driver for acoustically reproducing the noise reduction sound signal by D1. Further, the transfer function of a space from the driver to a cancel point Pc is represented by H1.

Meanwhile, in the noise reduction apparatus section 30 of the feedforward type, the transfer function of a portion corresponding to a microphone 31 and a microphone amplifier 32 is represented by M2; the transfer function of a power amplifier for amplifying a noise reduction sound signal generated by the FF filter circuit 33 by A2; and the transfer function of a driver for acoustically reproducing the noise reduction sound signal by D2. Further, the transfer function of a space from the driver to the cancel point Pc is represented by H2.

Further, in the embodiment of FIG. 45, a plurality of sets of filter coefficients to be supplied to each of the FB filter circuit 23 and the FF filter circuit 33 are stored in the memory 34. Each of the control circuits 304 and 404 provided in the DSPs 232 and 332 selects suitable filter coefficients from among the plurality of sets of filter coefficients in response to such beating of the headphone housing 2 by the user as described above and sets the filter coefficients to the filter circuit 23 or 33. This similarly applies also to equalizer characteristic alteration control based on beating of the headphone housing 2 by the user.

Further, in the example of FIG. 45, a system for acoustically reproducing a noise reduction sound signal generated by the noise reduction apparatus section of the feedback type and a system for acoustically reproducing a noise reduction sound signal generated by the noise reduction apparatus section of the feedforward type are provided separately from each other.

Further, in the example of FIG. 45, the power amplifier and the driver of the system for acoustically reproducing a noise reduction sound signal generated by the noise reduction apparatus section of the feedback type are used only for noise reduction. On the other hand, the power amplifier and the driver of the system for acoustically reproducing a noise reduction sound signal generated by the noise reduction apparatus section of the feedforward type are used not only for noise reduction but also for acoustic reproduction of the sound signal S of the listening object. Therefore, the sound signal S inputted through the input terminal 12 is converted into a digital signal by the A/D conversion circuit 25 and then supplied to the digital equalizer circuit formed in the DSP 332.

Further, in the example of FIG. 45, a sound signal S of an object of listening is converted into a digital sound signal by an A/D conversion circuit 25 and then supplied to the DSP 332 of the FF filter circuit 33. Though not shown in FIG. 45, the DSP 332 includes not only a digital filter for generating a noise reduction sound signal of the feedforward system but also an equalizer circuit for adjusting the sound characteristic of the sound signal S of the listening object and an addition circuit. An output signal of the equalizer circuit and the noise reduction sound signal generated by the digital filter are added by the addition circuit and outputted from the DSP 332.

In the present fifth embodiment, the noise reduction apparatus section 20 of the feedback type and the noise reduction apparatus section 30 of the feedforward type perform the above-described noise reduction process independently of each other. It is to be noted, however, that the noise cancel points Pc in both systems are set to the same position.

Accordingly, according to the fifth embodiment, the noise reduction processes of the feedback type and the feedforward type operate complementarily to each other. Consequently, a noise reduction system which can achieve the advantages of both systems can be implemented.

It is to be noted that, while, in FIG. 45, the filter coefficients of the digital filters in both of the feedback system and the feedforward system are altered, the noise reduction system may be configured otherwise such that the filter coefficients are selectively altered only for the digital filter of one of the systems, for example, only for the digital filter of the feedforward system.

Further, while, in the example of FIG. 45, the FB filter circuit 23 and the FF filter circuit 33 are formed in the DSPs separate from each other, they may otherwise be formed in one DSP so as to simplify the entire circuit configuration. Further, while, in the example of FIG. 45, also the power amplifiers and the drivers are provided separately in the noise reduction apparatus section 20 of the feedback type and the noise reduction apparatus section 30 of the feedforward type, also it is possible to form them as a single power amplifier 13 and a single driver 11 similarly as in the embodiments described hereinabove. An example where the configuration just described is shown in FIG. 46.

Figure 46:
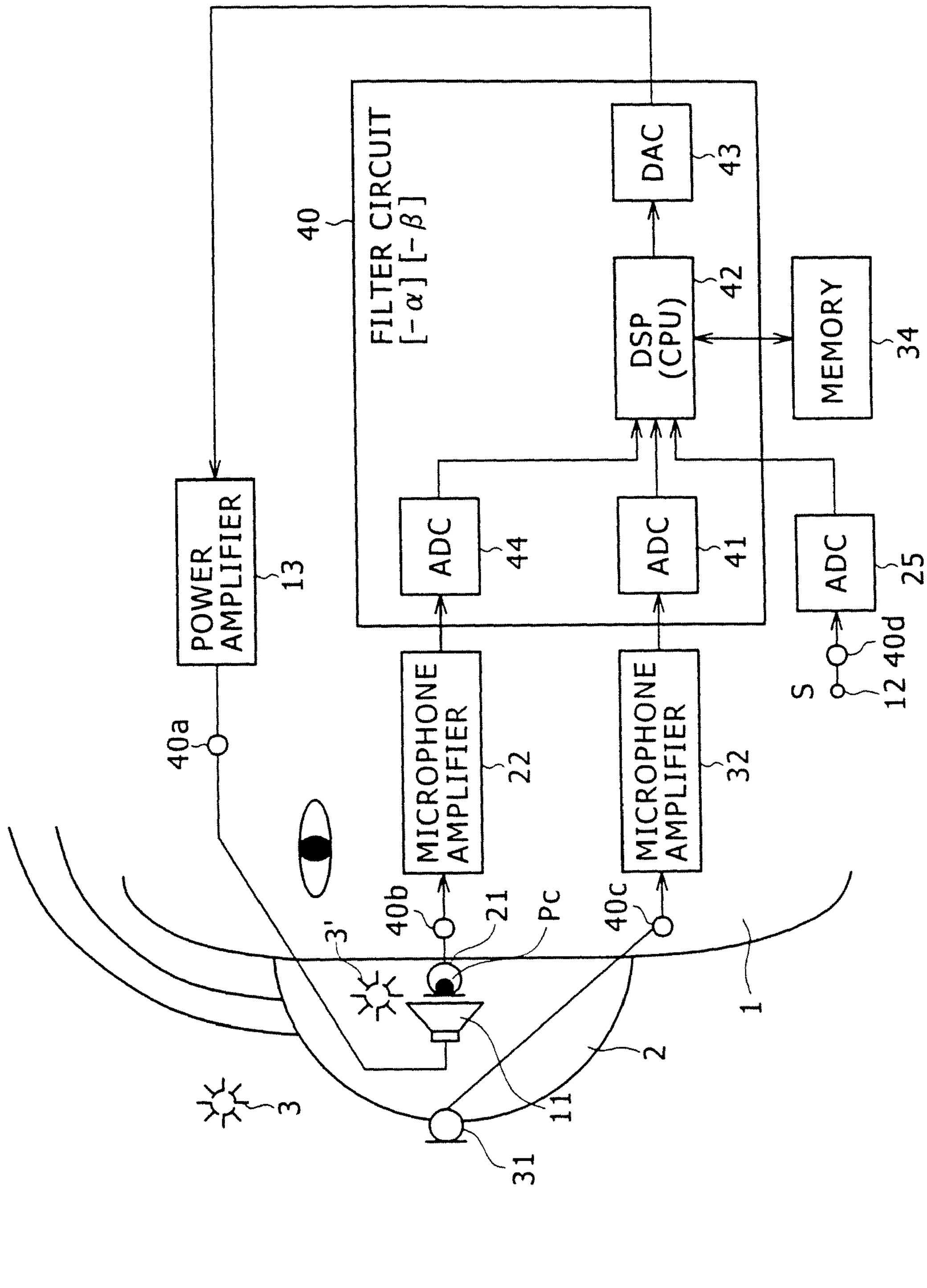
FIG. 46 is a block diagram showing another example of the headphone apparatus to which the fifth embodiment of the present invention is applied.

Referring to FIG. 46, the noise reduction system shown includes a filter circuit 40 which in turn includes an A/D conversion circuit 41, a DSP 42 and a D/A conversion circuit 43. An analog sound signal from the microphone amplifier 22 is converted into a digital sound signal by an A/D conversion circuit 44 and supplied to the DSP 42. Meanwhile, a sound signal S of an object of listening inputted through the input terminal 12 is converted into a digital sound signal by the A/D conversion circuit 25 and supplied to the DSP 42.

Figure 47:
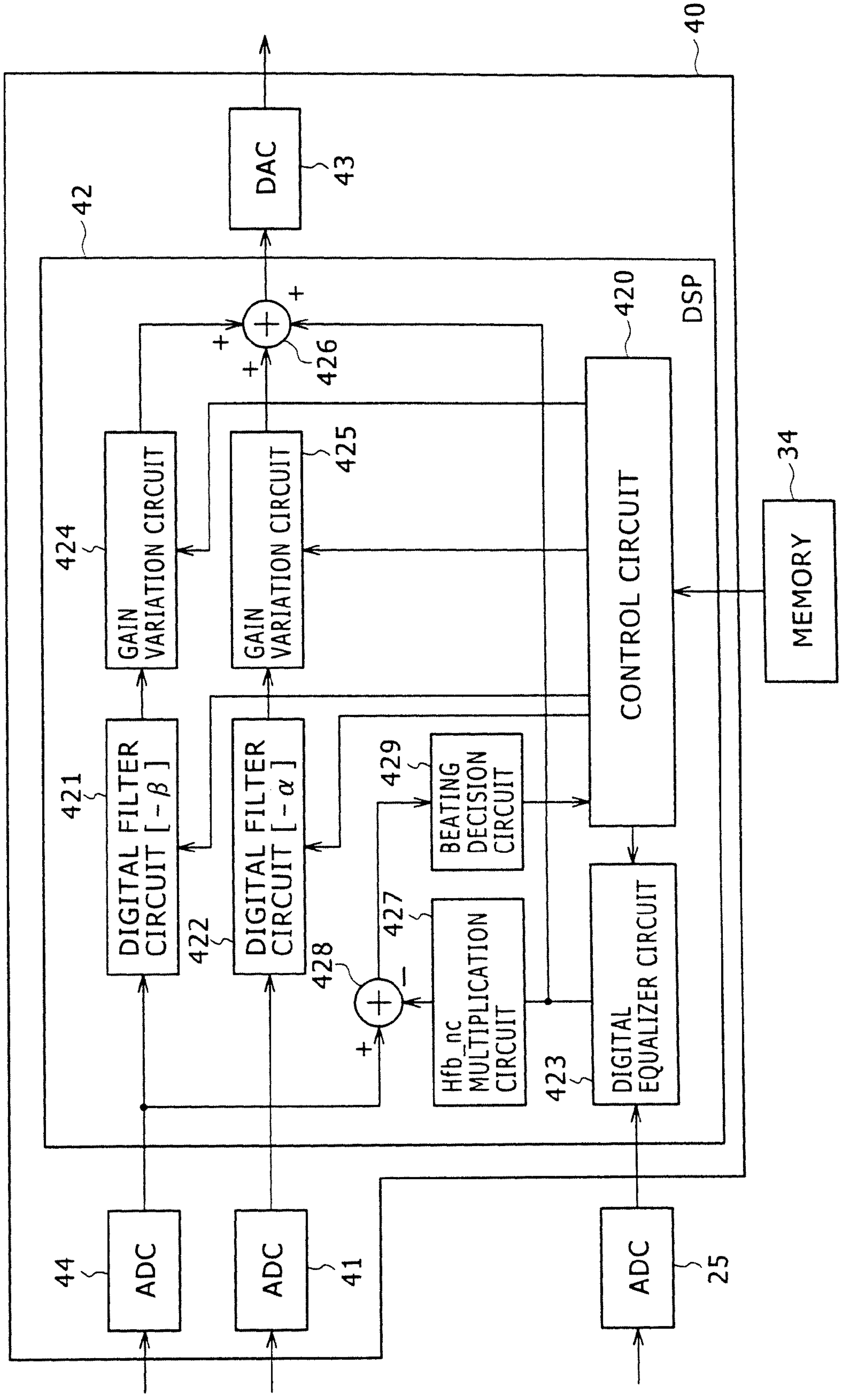
FIG. 47 is a block diagram showing an example of a detailed configuration of a filter circuit shown in FIG. 46.

Referring to FIG. 47, the DSP 42 in the present example includes a digital filter circuit 421 for generating a noise reduction sound signal of the feedback system, and another digital filter circuit 422 for generating a noise reduction sound signal of the feedforward system. The DSP 42 further includes a digital equalizer circuit 423, a pair of gain variation circuits 424 and 425, an addition circuit 426, an Hfb_nc multiplication circuit 427, a subtraction circuit 428, a beating decision circuit 429 and a control circuit 420.

A digital sound signal from the A/D conversion circuit 44, that is, a digital signal of sound collected by the microphone 21, is supplied to the digital filter circuit 421 while another digital signal from the A/D conversion circuit 41, that is a digital signal of sound collected by the microphone 31, is supplied to the digital filter circuit 422. Further, a digital sound signal from the A/D conversion circuit 25, that is, a digital signal of sound of an object of listening, is supplied to the digital equalizer circuit 423.

Further, in the present example, a plurality of filter coefficients or a plurality of sets of filter coefficients for the digital filter circuit 421, a plurality of filter coefficients or a plurality of sets of filter coefficients for the digital filter circuit 422, parameters for equalizer characteristic alteration of the digital equalizer circuit 423 and beating waveform data for being used for the first example of the beating decision method described hereinabove are stored in the memory 34.

The control circuit 420 selects filter coefficients for the digital filter circuit 421 and the digital filter circuit 422 from within the memory 34 in response to a decision result of one beating operation from the beating decision circuit 429 and supplies the selected filter coefficients to the digital filter circuit 421 and the digital filter circuit 422.

Also parameters with which the equalizer characteristics of the digital equalizer circuit 423 are made correspond to a plurality of filter coefficients or a plurality of sets of filter coefficients for the digital filter circuit 422 are stored in the memory 34. The control circuit 420 selectively reads out a parameter for an equalizer characteristic from the memory 34 in response to selection of filter coefficients for the digital filter circuit 422 in response to a user operation through an operation section 35 in accordance with a decision result of one beating operation from the beating decision circuit 429. Then, the control circuit 420 supplies the selectively read out parameter to the digital equalizer circuit 423.

The gain variation circuits 424 and 425 are provided on the output side of the digital filter circuits 421 and 422, respectively, similarly as in the embodiments described hereinabove. The gain variation circuits 424 and 425 control such a noise reduction effect upon alteration of the noise mode as described above under the control of the control circuit 420.

Then, noise reduction sound signals generated by the digital filter circuits 421 and 422 and obtained through the gain variation circuits 424 and 425 and a digital sound signal from the digital equalizer circuit 423 are supplied to and added by the addition circuit 426. Then, an addition result is supplied to the D/A conversion circuit 43, by which it is converted into an analog sound signal. The analog sound signal from the D/A conversion circuit 43 is supplied to the driver 11 through the power amplifier 13. Consequently, noise 3' is reduced or canceled at the cancel point Pc.

Further, the control circuit 420 selectively reads out parameters for alteration of the equalizer characteristic from the memory 34 in response to a result of decision of two beating operations from the beating decision circuit 429 and supplies the parameters to the digital equalizer circuit 423.

Then, the beating decision method according to the present example uses the first example of the first embodiment described hereinabove and involves beating decision from a collected sound signal from the microphone 21. In particular, the Hfb_nc multiplication circuit 427 multiplies the sound signal from the digital equalizer circuit 423 by the transfer function Hfh_nc, and the subtraction circuit 428 subtracts a result of the multiplication from the collected sound signal of the microphone 21 from the A/D conversion circuit 44.

Then, an output signal of the subtraction circuit 428 is supplied to the beating decision circuit 429, by which the first example of the beating decision in the first embodiment described hereinabove is executed. Then, a result of the beating decision is supplied to the control circuit 420. The control circuit 420 performs noise mode changeover alteration control and equalizer characteristic alteration control based on the beating decision result as described hereinabove.

It is to be noted that the noise reduction apparatus section is connected to the driver 11, microphone 21, microphone 31 and input terminal 12 (headphone plug) through connection terminal portions 40*a*, 40*b*, 40*c* and 40*d* by connection cables, respectively, as seen in FIG. 46.

Also in the present fifth embodiment, upon changeover alteration of the noise mode, such control operation as in the example described hereinabove is performed under the control of the control circuit 420 in a quite similar manner as in the first and second embodiments.

Sixth Embodiment

The sixth embodiment of the present invention improves, taking that the fifth embodiment involves only digital processing and has a problem of delay in an A/D conversion circuit and a D/A conversion circuit into consideration, the fifth embodiment in terms of the problem of delay similarly as in the third and fourth embodiments described hereinabove.

Figure 48:
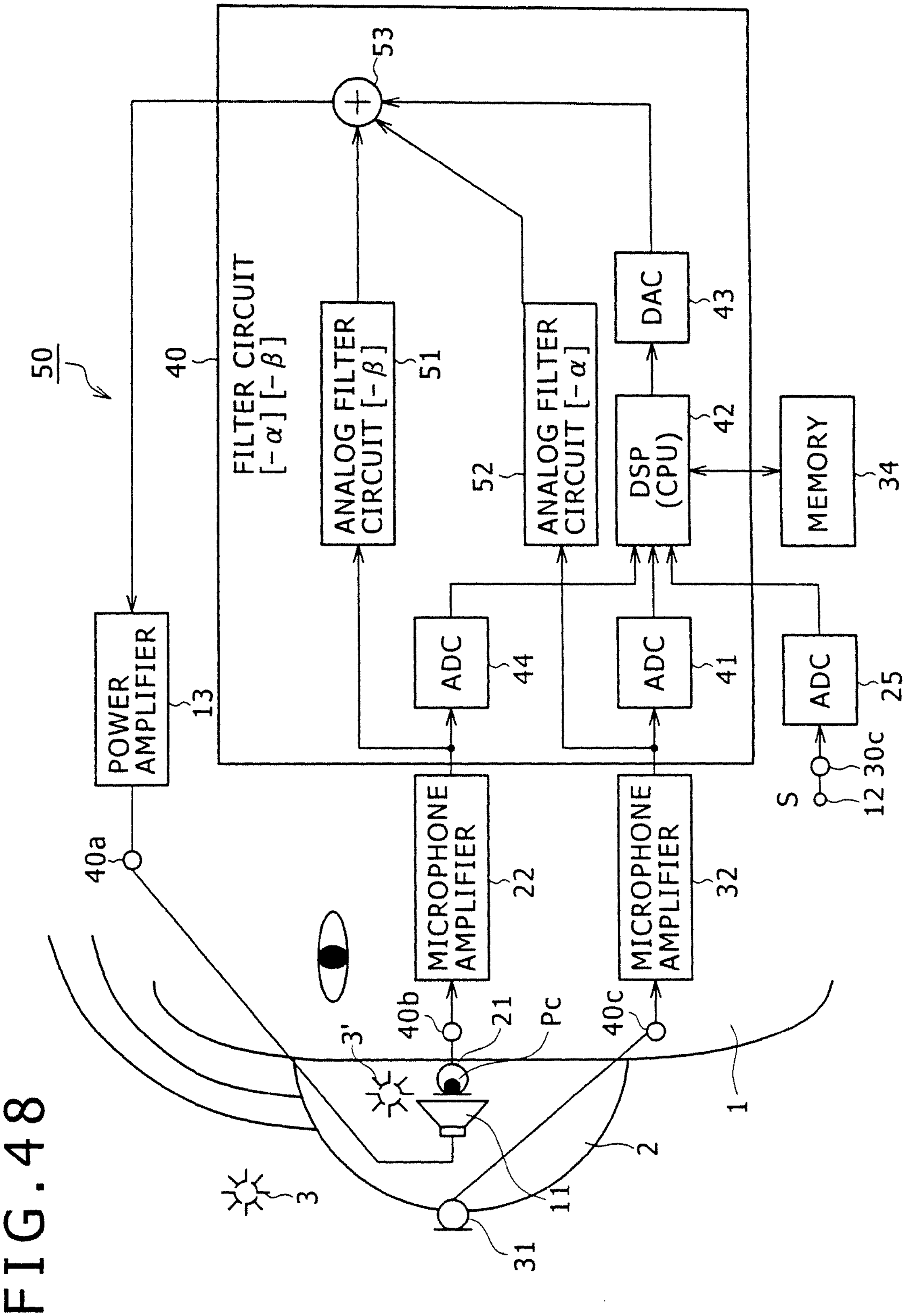
FIG. 48 is a block diagram showing an example of a headphone apparatus to which a sixth embodiment of the present invention is applied.

In particular, in the present sixth embodiment, an analog filter system is provided in parallel to a digital filter system similarly as in the third and fourth embodiments shown in FIGS. 42 and 44. FIG. 48 shows an example of a noise reduction apparatus section 50 in the sixth embodiment.

Referring to FIG. 48, the noise reduction apparatus section 50 of the sixth embodiment includes an analog filter circuit 51 for generating a noise reduction sound signal of the feedback type, another analog filter circuit 52 for generating an analog noise reduction sound signal of the feedforward type, and an addition circuit 53 in addition to the components shown in FIG. 47.

An analog sound signal from the microphone amplifier 22 is supplied to the A/D conversion circuit 44 and also to the analog filter circuit 51 for generating an analog noise reduction sound signal of the feedback type. The analog noise reduction sound signal from the analog filter circuit 51 is supplied to the addition circuit 53.

Meanwhile, an analog sound signal from the microphone amplifier 32 is supplied to the A/D conversion circuit 41 and also to the analog filter circuit 52 for generating an analog noise reduction sound signal of the feedforward type. Then, an analog noise reduction sound signal from the analog filter circuit 52 is supplied to the addition circuit 53.

Further, an addition signal of the noise reduction sound signal and the listening object sound signal from the D/A conversion circuit 43 is supplied to the addition circuit 53. Then, the sound signal from the addition circuit 53 is supplied to the driver 11 through a power amplifier 13. Consequently, according to the present embodiment, the problem of a case wherein both of the noise reduction process of the feedback type and the noise reduction process of the feedforward type are used and a noise reduction sound signal is generated only by means of a digital filter can be solved. Consequently, a noise reduction apparatus and a headphone apparatus which can be implemented for general consumers can be provided.

Also in the present sixth embodiment, upon changeover alteration of the noise mode, such control operation as in the embodiments described above is performed under the control of the control circuit 420 in a quite similar manner as in the fifth embodiment.

Other Embodiments Regarding the Beating Decision Method

Decision or detection of beating of the headphone housing 2 can be performed by a more simplified method where the microphone 21 or 31 is configured in the following manner.

Figure 49:
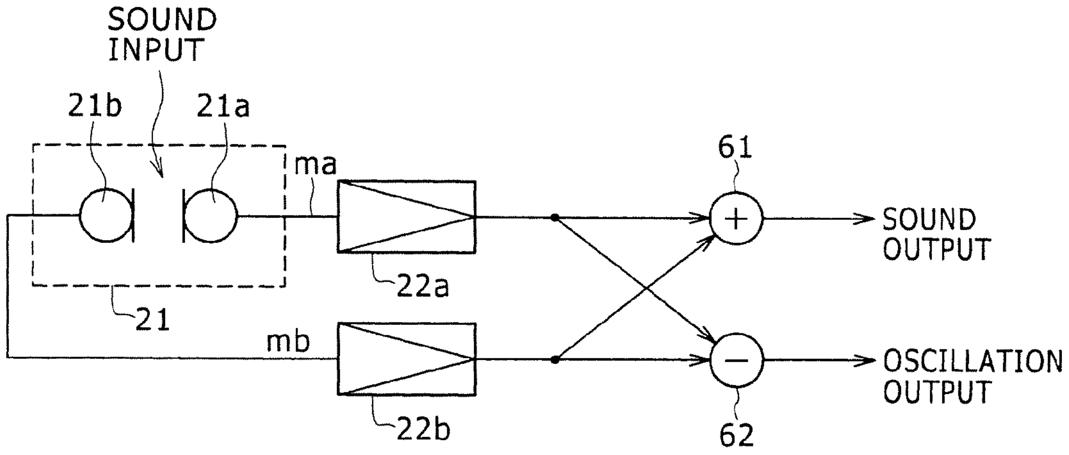
FIGS. 49 to 50B are views illustrating another beating decision method for the sound outputting apparatus according to the first to sixth embodiments of the present invention.
Figure 50A:
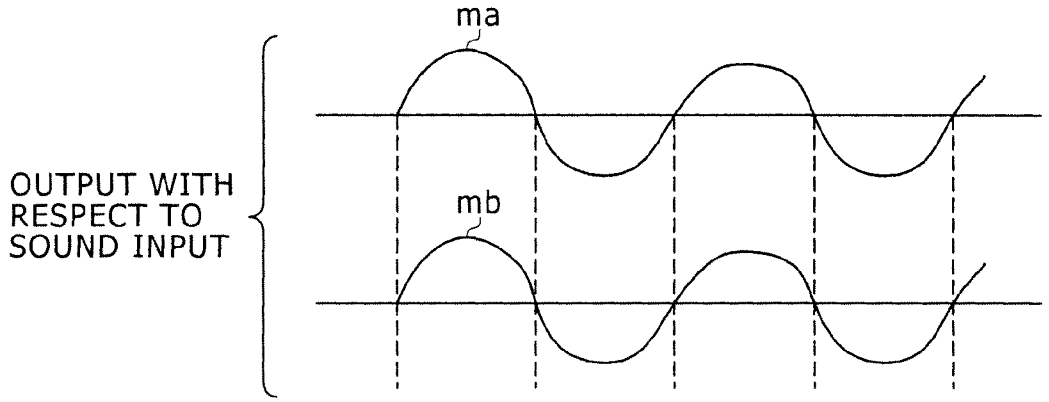

In particular, FIG. 49 shows an example wherein the present embodiment is applied to a microphone 21. Referring to FIG. 49, in the example illustrated, the microphone 21 includes two microphone elements 21*a* and 21*b* provided such that diaphragms thereof are opposed to each other. Then, sound (reproduction input) to be collected is inputted between the opposing diaphragms of the microphone elements 21*a* and 21*b*.

Where the structure just described is used, a convex direction oscillation and a concave direction oscillation of the diaphragms of the microphone elements 21*a* and 21*b* responsive to collected sound have the same phase. Therefore, an output signal ma of the microphone element 21*a* and an output signal mb of the microphone element 21*b* have the same phase as seen in FIG. 50A. Accordingly, if the output signals ma and mb from the microphone elements 21*a* and 21*b* are added through microphone amplifiers 22*a* and 22*b* by an addition circuit 61, then an output signal of the collected sound signal can be obtained.

Figure 50B:
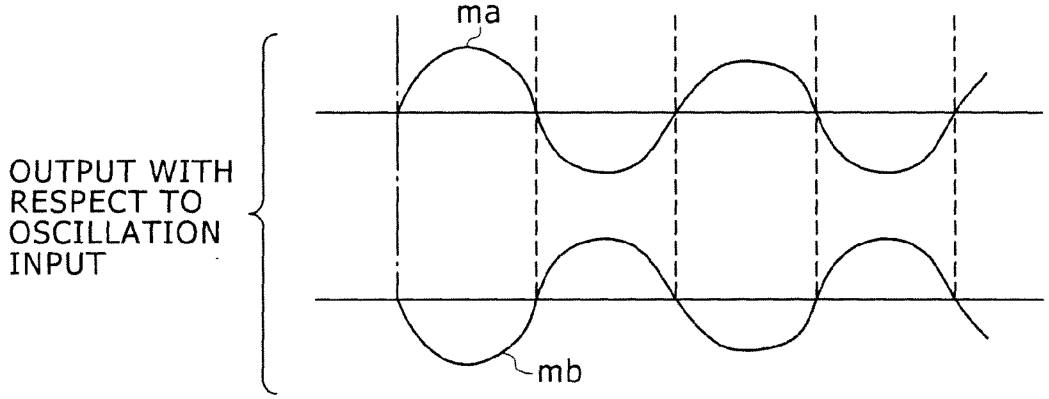

On the other hand, oscillations caused by beating of the headphone housing 2 are applied to the entire microphone 21. Therefore, a convex direction oscillation and a concave direction oscillation of the diaphragms of the microphone elements 21*a* and 21*b* have the opposite phases. Therefore, the output signal ma of the microphone element 21*a* and the output signal mb of the microphone element 21*b* have the opposite phase as seen in FIG. 50B. Accordingly, a component of oscillations caused by beating of the headphone housing 2 is removed by the addition circuit 61.

On the other hand, if an output signal of the microphone amplifier 22*a* and an output signal of the microphone amplifier 22*b* are subtracted by a subtraction circuit 62, then although collected sound signal components of the same phase cancel each other, oscillation components produced by beating of the headphone housing 2 and having the opposite phases to each other remain.

Then, if a beating component which exceeds a predetermined threshold value is detected from within the oscillation components, then it can be detected that the headphone housing 2 is beaten by the user.

Other Embodiments and Modifications

In the first to sixth embodiments described above, every time the headphone housing 2 is beaten once, the NC filter to be formed in the digital filter circuit and hence the noise mode are altered. However, the present invention can be applied also where it is detected with which noise reduction amount it is suitable to use the NC filter of the same noise mode.

Figure 51:
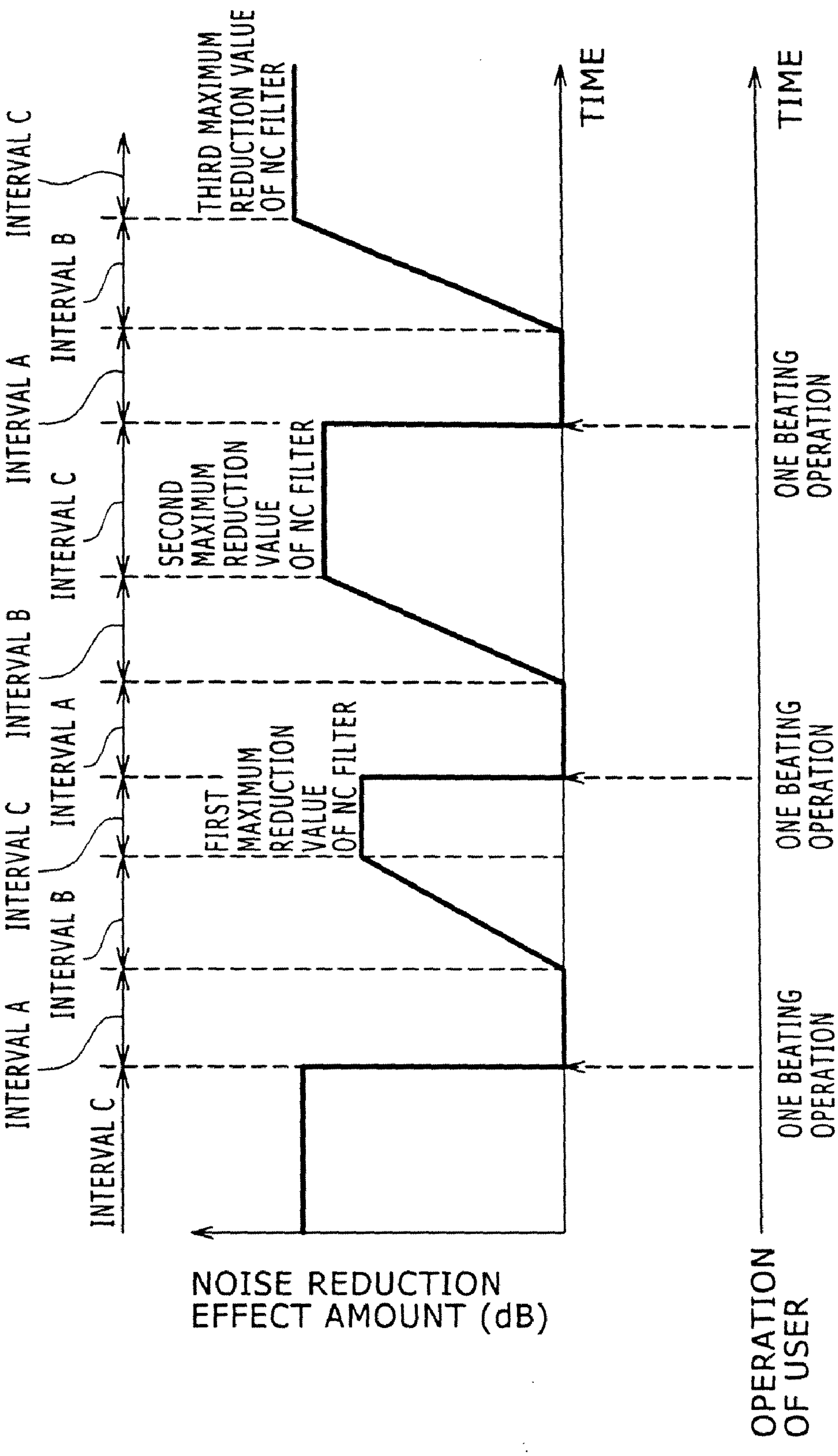
FIG. 51 is a waveform diagram illustrating a different example of operation of the sound outputting apparatus according to the first to sixth embodiments of the present invention.

In particular, in this instance, every time one beating operation of the headphone housing 2 is detected, the maximum reduction amount within the noise reduction effect gradually increasing interval B is successively altered to a first maximum reduction amount, a second maximum reduction amount, a third maximum reduction amount or the like as seen in FIG. 51 using one NC filter. The user can decide which maximum reduction amount is effective as the maximum reduction amount of the NC filter.

Further, in the first to sixth embodiments described hereinabove, every time the headphone housing 2 is beaten once, notification where the noise mode is altered to a noise mode corresponding to a different noise environment is performed using sound. However, the notification is not restricted to sound. For example, a display section may be provided in the apparatus such that the name ("Platform of a railway station", "Airport", "In an electric train" or the like) of each noise environment (noise mode) may be displayed so as to notify the user.

Further, in the embodiments described above, every time the headphone housing 2 is beaten once, the noise mode is altered. The control circuit of the DSP may be configured such that, if one user operation is performed, then a plurality of NC filters of different noise modes are successively set to the digital filter circuit for each fixed period determined in advance from the memory 24 or memory 34 such that the listener may experience the noise reduction effect for each fixed period of time. In this instance, a noise reduction effect off interval A, a noise reduction effect gradually increasing period B, a noise reduction effect maximum interval C, a notification interval D and a noise reduction effect gradually decreasing interval E may be provided within the fixed period of time so that delimiting of the experience interval of the noise reduction effects of the individual NC filters is made definite.

It is to be noted that, where a plurality of noise modes are presented successively to the user in this manner, after listening of the noise reduction effect regarding the NC filters of all noise modes is completed, an input representing what numbered noise mode is optimum is received from the listener, or at a point of time during selection of a noise mode decided as an optimum noise mode by the user, the user performs a predetermined user operation, so that the user may determine a noise mode. In the latter case, an operation of successively selecting a plurality of noise modes so that the listener may listen for each predetermined period of time is repeated several times for the plural filter coefficients.

It is to be noted that, where, when the user decides whether or not the current noise mode is optimum, a sound signal S of an object of listening is being reproduced and the decision is difficult, when a user operation for filter coefficient alteration such as beating of the headphone housing 2 is performed, the sound signal S should be muted compulsorily for a predetermined period of time within which the user can decide a noise reduction effect.

In the embodiments described above, the digital filter circuit in the FB filter circuit and the FF filter circuit is formed using a DSP. However, the DSP may be replaced by a microcomputer or a microprocessor to perform the processing of the digital filter circuit in accordance with a software program.

Where a microcomputer or a microprocessor is used in place of a DSP, also the part of the memory controller may be formed from the software program. Also it is possible to conversely form the part of the memory controller in a DSP.

Further, in the embodiments described above, the sound outputting apparatus of the embodiments of the present invention is a headphone apparatus. However, the present invention can be applied also to an earphone apparatus or a headset apparatus which includes a microphone or also to a communication terminal such as a portable telephone terminal.

Further, the sound outputting apparatus of the embodiments of the present invention can be applied also to a portable music reproduction apparatus combined with a headphone, an earphone or a headset.

In this instance, the electro-acoustic conversion section is not limited to a headphone driver but may be an earphone driver. Meanwhile, the acousto-electric may have any structure as long as it can convert oscillations by sound waves into an electric signal.

Further, the noise reduction apparatus section which includes a DSP including a beating decision circuit or a digital filter circuit and so forth is provided, in the embodiments described hereinabove, on the headphone side apparatus. However, the noise reduction apparatus section may otherwise be provided on a portable music reproduction apparatus side on which the headphone apparatus is mounted or on the portable music reproduction apparatus side compatible with an earphone or a headset which includes a microphone.

Further, in the embodiments described above, the filter coefficient of the digital filter is altered. However, the present invention can be applied also where hardware of the analog filter is changed over to change over the noise reduction characteristic in response to a noise environment.

Further, the present invention can be applied not only to a system which uses a headphone apparatus or an earphone apparatus but also to a system wherein a housing of a portable music reproduction apparatus or a like apparatus is beaten by the user.

Further, the object of utilization of a result of beating decision can be applied not only to changeover alteration of the noise mode or alteration control of the equalizer characteristic in such a noise reduction apparatus section as described above but also, for example, to various applications such as changeover of the reproduction speed, changeover between fast feeding and rewinding in a portable music reproduction apparatus. Further, the utilization object described above can be applied also where, in a sound outputting apparatus wherein a plurality of processes including an acoustic effect process and other processes for a sound signal can be used switchably, such acoustic effect process and other processes are successively changed over to confirm effects of them.

It is to be noted that, while, in the foregoing description, beating is described as an operation of the user for a housing of a particular object, the present invention can be applied also for decision or detection of a user operation when a headphone housing is rubbed or the like.

While preferred embodiments of the present invention have been described using specific terms, such description is for illustrative purposes only, and it is to be understood that changes and variations may be made without departing from the spirit or scope of the following claims.

What is claimed is:

1. A sound outputting apparatus, comprising:

a housing;

an electro-acoustic conversion section provided in said housing and configured to acoustically reproduce and output a sound signal;

an acousto-electric conversion section provided at a position of said housing at which sound acoustically reproduced by said electro-acoustic conversion section can be collected;

a removing section configured to remove a component of the sound signal from an output signal to be outputted from said acousto-electric conversion section based on an acoustic transfer function between said electro-acoustic conversion section and said acousto-electric conversion section;

a decision section configured to decide whether or not a predetermined operation is performed for said housing based on an output signal from said removing section; and a control section configured to control so that a predetermined process determined in advance is performed based on a result of the decision by said decision section.

2. The sound outputting apparatus according to claim 1, wherein the predetermined operation for said housing is beating of said housing, and said decision section decides whether or not the predetermined operation is performed for said housing based on a correlation between a basic waveform, stored in a storage section, of a signal outputted from said acousto-electric conversion section when said housing is beaten and a waveform of the output signal from said removing section.

3. The sound outputting apparatus according to claim 2, wherein said control section causes said storage section to store a waveform of the output signal outputted from said acousto-electric conversion section when said housing is beaten as the basic waveform.

4. The sound outputting apparatus according to claim 1, wherein the predetermined operation for said housing is beating of said housing, and said decision section checks the maximum amplitude value of the output signal outputted from said removing section and decides whether or not the predetermined operation is performed for said housing based on an attenuation ratio from the maximum amplitude value.

5. The sound outputting apparatus according to claim 1, wherein the predetermined operation for said housing is beating of said housing, and said decision section decides whether or not predetermined operation is performed for said housing based on whether or not the maximum amplitude value of the signal from said removing section is equal to or higher than a predetermined value set in advance.

6. The sound outputting apparatus according to claim 5, further comprising a selection section configured to selectively set the predetermined value.

7. The sound outputting apparatus according to claim 1, wherein the predetermined operation for said housing is beating of said housing;

said housing is structured such that resonance occurs at a specific resonance frequency when said housing is beaten; and said decision section includes a filter section configured to extract signal components centered at the resonance frequency from the signal from said removing section and decides whether or not said housing is beaten based on a signal from said filter section.

8. The sound outputting apparatus according to claim 1, further comprising a noise reduction processing system configured to generate a noise reduction sound signal for reducing noise based on the signal of noise outputted from said acousto-electric conversion section and acoustically reproduce the noise reduction sound signal by said electro-acoustic conversion section.

9. The sound outputting apparatus according to claim 1, wherein the predetermined operation for said housing is beating of said housing;

said decision section further decides the number of times by which said housing is beaten; and said control section performs a different process based on the number of times of beating of said housing.

10. The sound outputting apparatus according to claim 1, wherein the predetermined process performed by said control section is a volume adjustment process of sound to be acoustically reproduced by said electro-acoustic conversion section.

11. The sound outputting apparatus according to claim 1, wherein the predetermined process performed by said control section is at least one of alteration processes of an amplitude frequency characteristic and a phase frequency characteristic regarding the sound signal to be acoustically reproduced by said electro-acoustic conversion section.

12. The sound outputting apparatus according to claim 8, wherein the predetermined process performed by said control section is a process of altering a noise reduction characteristic for generating the noise reduction sound signal.

13. The sound outputting apparatus according to claim 1, wherein said sound outputting apparatus is a headphone apparatus.

14. The sound outputting apparatus according to claim 1, wherein said sound outputting apparatus is a portable telephone terminal.

15. The sound outputting apparatus according to claim 1, wherein said acousto-electric conversion section includes a pair of acousto-electric conversion elements whose diaphragm are disposed in an opposing relationship to each other such that an opposing space therebetween functions as an inputting space for sound waves to be collected, and said decision section decides whether or not the predetermined operation is performed for said housing based on a subtraction output signal between output signals outputted from said acousto-electric conversion elements of said acousto-electric conversion section.

* * * * *

UNITED STATES PATENT AND TRADEMARK OFFICE

CERTIFICATE OF CORRECTION

PATENT NO. : 8,204,241 B2
APPLICATION NO. : 11/952468
DATED : June 19, 2012
INVENTOR(S) : Kohei Asada et al.

It is certified that error appears in the above-identified patent and that said Letters Patent is hereby corrected as shown below:

In the Claims

Column 48, line 58, please add

" 16. A sound outputting method, comprising steps of:

acoustically reproducing and outputting a sound signal by means of an electro-acoustic conversion section provided in a housing;

collecting sound and outputting an output signal by means of an acousto-electric conversion section provided at a position of the housing at which sound acoustically reproduced by the electro-acoustic conversion section can be collected;

removing a component of the sound signal from the output signal outputted from the acousto-electric conversion section based on an acoustic transfer function between the electro-acoustic conversion section and the acousto-electric conversion section;

deciding whether or not a predetermined operation is performed for the housing based on the output signal from which the sound signal component is removed; and controlling so that a predetermined process determined in advance is performed based on a result of the decision at the decision step.

17. A computer-readable recording medium on which a program is recorded, the program causing a computer to execute steps of:

acoustically reproducing and outputting a sound signal by means of an electro-acoustic conversion section provided in a housing;

collecting sound and outputting an output signal by means of an acousto-electric conversion section provided at a position of the housing at which sound acoustically reproduced by the electro-acoustic conversion section can be collected;

removing a component of the sound signal from the output signal outputted from the acousto-electric conversion section based on an acoustic transfer function between the electro-acoustic conversion section and the acousto-electric conversion section;

deciding whether or not a predetermined operation is performed for the housing based on the output signal from which the sound signal component is removed; and controlling so that a predetermined process determined in advance is performed based on a result of the decision at the decision step.

Signed and Sealed this
Twenty-seventh Day of August, 2013

Teresa Stanek Rea
*Acting Director of the United States Patent and Trademark Office*

In the Claims (continued)

18. A sound outputting system, comprising:
a headphone apparatus; and
a sound outputting apparatus to which said headphone apparatus is connected;
said headphone apparatus including:
a housing;
an electro-acoustic conversion section provided in said housing and configured to acoustically reproduce and output a sound signal from said sound outputting apparatus; and
an acousto-electric conversion section provided at a position at which sound acoustically reproduced by the electro-acoustic conversion section can be collected;
said sound outputting apparatus including:
a removing section configured to remove a component of the sound signal from an output signal outputted from the acousto-electric conversion section based on an acoustic transfer function between the electro-acoustic conversion section and the acousto-electric conversion section;
a decision section configured to decide whether or not a predetermined operation is performed for the housing based on an output signal outputted from the removing section; and
a control section configured to control so that a predetermined process is performed based on a result of the decision by the decision section.

19. A sound outputting apparatus, comprising:
a housing;
electro-acoustic conversion means provided in said housing and configured for acoustically reproducing and outputting a sound signal;
acousto-electric conversion means provided at a position of said housing at which sound acoustically reproduced by said electro-acoustic conversion means can be collected;
removing means configured for removing a component of the sound signal from an output signal to be outputted from said acousto-electric conversion means based on an acoustic transfer function between said electro-acoustic conversion means and said acousto-electric conversion means;
decision means configured for deciding whether or not a predetermined operation is performed for said housing based on an output signal from said removing means; and
control means configured for controlling so that a predetermined process determined in advance is performed based on a result of the decision by said decision means.

20. A sound outputting system, comprising:
a headphone apparatus; and
a sound outputting apparatus to which said headphone apparatus is connected;
said headphone apparatus including:
a housing;
electro-acoustic conversion means provided in said housing and configured for acoustically reproducing and outputting a sound signal from said sound outputting apparatus; and
acousto-electric conversion means provided at a position at which sound acoustically reproduced by the electro-acoustic conversion means can be collected;
said sound outputting apparatus including:

In the Claims (continued)

removing means configured for removing a component of the sound signal from an output signal outputted from the acousto-electric conversion means based on an acoustic transfer function between the electro-acoustic conversion means and the acousto-electric conversion means;

decision means configured for deciding whether or not a predetermined operation is performed for the housing based on an output signal outputted from the removing means; and control means configured for controlling so that a predetermined process is performed based on a result of the decision by the decision means."

CERTIFICATE OF CORRECTION

PATENT NO. : 8,204,241 B2
APPLICATION NO. : 11/952468
DATED : June 19, 2012
INVENTOR(S) : Kohei Asada et al.

It is certified that error appears in the above-identified patent and that said Letters Patent is hereby corrected as shown below:

Delete the title page and substitute therefore with the attached title page showing the corrected number of claims in patent.

In the Claims

Column 48, line 58, please add
"

16. A sound outputting method, comprising steps of:
acoustically reproducing and outputting a sound signal by means of an electro-acoustic conversion section provided in a housing;
collecting sound and outputting an output signal by means of an acousto-electric conversion section provided at a position of the housing at which sound acoustically reproduced by the electro-acoustic conversion section can be collected;
removing a component of the sound signal from the output signal outputted from the acousto-electric conversion section based on an acoustic transfer function between the electro-acoustic conversion section and the acousto-electric conversion section;
deciding whether or not a predetermined operation is performed for the housing based on the output signal from which the sound signal component is removed; and
controlling so that a predetermined process determined in advance is performed based on a result of the decision at the decision step.

This certificate supersedes the Certificate of Correction issued August 27, 2013.

Signed and Sealed this
Seventeenth Day of September, 2013

Teresa Stanek Rea
*Deputy Director of the United States Patent and Trademark Office*

17. A computer-readable recording medium on which a program is recorded, the program causing a computer to execute steps of:

acoustically reproducing and outputting a sound signal by means of an electro-acoustic conversion section provided in a housing;

collecting sound and outputting an output signal by means of an acousto-electric conversion section provided at a position of the housing at which sound acoustically reproduced by the electro-acoustic conversion section can be collected;

removing a component of the sound signal from the output signal outputted from the acousto-electric conversion section based on an acoustic transfer function between the electro-acoustic conversion section and the acousto-electric conversion section;

deciding whether or not a predetermined operation is performed for the housing based on the output signal from which the sound signal component is removed; and controlling so that a predetermined process determined in advance is performed based on a result of the decision at the decision step.

18. A sound outputting system, comprising:

a headphone apparatus; and a sound outputting apparatus to which said headphone apparatus is connected;

said headphone apparatus including:

a housing;

an electro-acoustic conversion section provided in said housing and configured to acoustically reproduce and output a sound signal from said sound outputting apparatus; and an acousto-electric conversion section provided at a position at which sound acoustically reproduced by the electro-acoustic conversion section can be collected;

said sound outputting apparatus including:

a removing section configured to remove a component of the sound signal from an output signal outputted from the acousto-electric conversion section based on an acoustic transfer function between the electro-acoustic conversion section and the acousto-electric conversion section;

a decision section configured to decide whether or not a predetermined operation is performed for the housing based on an output signal outputted from the removing section; and a control section configured to control so that a predetermined process is performed based on a result of the decision by the decision section.

19. A sound outputting apparatus, comprising:

a housing;

electro-acoustic conversion means provided in said housing and configured for acoustically reproducing and outputting a sound signal;

acousto-electric conversion means provided at a position of said housing at which sound acoustically reproduced by said electro-acoustic conversion means can be collected;

removing means configured for removing a component of the sound signal from an output signal to be outputted from said acousto-electric conversion means based on an acoustic transfer function between said electro-acoustic conversion means and said acousto-electric conversion means;

decision means configured for deciding whether or not a predetermined operation is performed for said housing based on an output signal from said removing means; and control means configured for controlling so that a predetermined process determined in advance is performed based on a result of the decision by said decision means.

20. A sound outputting system, comprising:

a headphone apparatus; and a sound outputting apparatus to which said headphone apparatus is connected;

said headphone apparatus including:

a housing;

electro-acoustic conversion means provided in said housing and configured for acoustically reproducing and outputting a sound signal from said sound outputting apparatus; and acousto-electric conversion means provided at a position at which sound acoustically reproduced by the electro-acoustic conversion means can be collected;

said sound outputting apparatus including:

removing means configured for removing a component of the sound signal from an output signal outputted from the acousto-electric conversion means based on an acoustic transfer function between the electro-acoustic conversion means and the acousto-electric conversion means;

decision means configured for deciding whether or not a predetermined operation is performed for the housing based on an output signal outputted from the removing means; and control means configured for controlling so that a predetermined process is performed based on a result of the decision by the decision means."

(12) United States Patent
Asada et al.

(10) Patent No.: US 8,204,241 B2
(45) Date of Patent: Jun. 19, 2012

(54) SOUND OUTPUTTING APPARATUS, SOUND OUTPUTTING METHOD, SOUND OUTPUT PROCESSING PROGRAM AND SOUND OUTPUTTING SYSTEM

(75) Inventors: Kohei Asada, Kanagawa (JP); Goro Shiraishi, Tokyo (JP)

(73) Assignee: Sony Corporation, Tokyo (JP)

( * ) Notice: Subject to any disclaimer, the term of this patent is extended or adjusted under 35 U.S.C. 154(b) by 1170 days.

(21) Appl. No.: 11/952,468

(22) Filed: Dec. 7, 2007

(65) Prior Publication Data

US 2008/0159568 A1 Jul. 3, 2008

(30) Foreign Application Priority Data

Dec. 27, 2006 (JP) ................................ 2006-350962

(51) Int. Cl.
*A61F 11/06* (2006.01)
*G10K 11/16* (2006.01)
*H03B 29/00* (2006.01)

(52) U.S. Cl. .................. 381/71.1; 381/71.6; 381/71.11; 381/150

(58) Field of Classification Search ................ 381/71.1, 381/71.6, 71.11, 150, 370
See application file for complete search history.

(56) References Cited

U.S. PATENT DOCUMENTS

| | | | | |
|---|---|---|---|---|
| 5,452,361 A * | 9/1995 | Jones | ........................ | 381/71.6 |
| 2003/0228019 A1 * | 12/2003 | Eichler et al. | ............... | 381/71.8 |
| 2006/0013408 A1 * | 1/2006 | Lee | ........................... | 381/71.6 |
| 2007/0036367 A1 * | 2/2007 | Ko | ............................ | 381/71.1 |
| 2009/0034748 A1 * | 2/2009 | Sibbald | ...................... | 381/71.6 |

FOREIGN PATENT DOCUMENTS

| | | |
|---|---|---|
| JP | 2-231900 | 9/1990 |
| JP | 6-70391 | 3/1994 |
| JP | 8-79873 | 3/1996 |
| JP | 2003-143683 | 5/2003 |
| JP | 3114245 | 9/2005 |

OTHER PUBLICATIONS

U.S. Appl. No. 11/936,894, filed Nov. 8, 2007, Asada, et al.
U.S. Appl. No. 11/865,419, filed Oct. 1, 2007, Asada, et al.
U.S. Appl. No. 11/865,354, filed Oct. 1, 2007, Asada.
U.S. Appl. No. 11/868,815, filed Oct. 8, 2007, Itabashi, et al.
U.S. Appl. No. 11/875,374, filed Oct. 19, 2007, Asada.
U.S. Appl. No. 11/936,882, filed Nov. 8, 2007, Asada, et al.
U.S. Appl. No. 11/936,876, filed Nov. 8, 2007, Asada, et al.
U.S. Appl. No. 11/966,168, filed Dec. 28, 2007, Ohkuri, et al.
U.S. Appl. No. 11/966,452, filed Dec. 28, 2007, Itabashi, et al.
U.S. Appl. No. 12/015,824, filed Jan. 17, 2008, Asada, et al.
Japanese Office Action dated Jan. 24, 2012 in corresponding Japanese application No. 2006-350962, filed on Dec. 27, 2006.

* cited by examiner

*Primary Examiner* — Phat X Cao
(74) *Attorney, Agent, or Firm* — Oblon, Spivak, McClelland, Maier & Neustadt, L.L.P.

(57) ABSTRACT

The present invention provides a sound outputting apparatus, including: a housing; an electro-acoustic conversion section provided in the housing and configured to acoustically reproduce and output a sound signal; an acousto-electric conversion section provided at a position of the housing at which sound acoustically reproduced by the electro-acoustic conversion section can be collected; a removing section configured to remove a component of the sound signal from an output signal to be outputted from the acousto-electric conversion section based on an acoustic transfer function between the electro-acoustic conversion section and the acousto-electric conversion section; a decision section configured to decide whether or not a predetermined operation is performed for the housing based on an output signal from the removing section; and a control section configured to control so that a predetermined process is performed based on a result of the decision by the decision section.

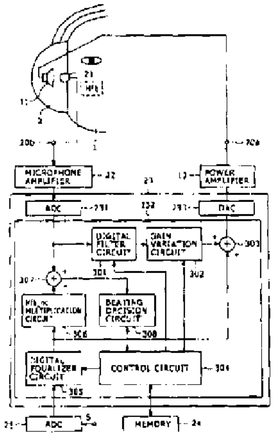

20 Claims, 45 Drawing Sheets